United States Patent
Thum et al.

(10) Patent No.: US 9,388,411 B2
(45) Date of Patent: Jul. 12, 2016

(54) MIRNA-212/132 FAMILY AS A THERAPEUTIC TARGET

(75) Inventors: Thomas Thum, Hannover (DE); Kamal Chowdhury, Goettingen (DE); Ahmet Ucar, Heidelberg (DE); Shashi Kumar Gupta, Hannover (DE)

(73) Assignees: Max-Planck-Gesellschaft zur Foerderung der Wissenschaften e.V., Munich (DE); Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/342,867

(22) PCT Filed: Sep. 6, 2012

(86) PCT No.: PCT/EP2012/067443
§ 371 (c)(1),
(2), (4) Date: May 30, 2014

(87) PCT Pub. No.: WO2013/034653
PCT Pub. Date: Mar. 14, 2013

(65) Prior Publication Data
US 2014/0275220 A1    Sep. 18, 2014

Related U.S. Application Data

(60) Provisional application No. 61/531,156, filed on Sep. 6, 2011.

(51) Int. Cl.
| | | |
|---|---|---|
| *C07H 21/04* | (2006.01) | |
| *C12N 15/113* | (2010.01) | |
| *A61K 31/712* | (2006.01) | |
| *A61K 45/06* | (2006.01) | |
| *C12Q 1/68* | (2006.01) | |

(52) U.S. Cl.
CPC ............ *C12N 15/113* (2013.01); *A61K 31/712* (2013.01); *A61K 45/06* (2013.01); *C12Q 1/68* (2013.01); *C12N 2310/113* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 7,601,495 | B2 * | 10/2009 | Chen et al. | 435/6.12 |
| 7,683,036 | B2 * | 3/2010 | Esau et al. | 514/44 R |
| 2010/0010073 | A1 * | 1/2010 | Thum et al. | 514/44 R |

FOREIGN PATENT DOCUMENTS

| | | |
|---|---|---|
| WO | 2008/016924 A2 | 2/2008 |
| WO | 2009/106367 A1 | 9/2009 |
| WO | 2010/105096 A2 | 9/2010 |

OTHER PUBLICATIONS

Anker et al. (The Lancet et al. 1997, Vo. 349; 1050-1053).*
Park et al. (Biochemical and Biophysical Research Communications 406 (2011) 518-523).*
Claudia Jentzsch et al: "A phenotypic screen to identify hypertrophy-modulating microRNAs in primary cardiomyocytes", Journal of Molecular and Cellular Cardiology, Academic Press, GB, vol. 52, No. 1, Jul. 23, 2011, pp. 13-20, XP028346748, ISSN: 0022-2828, DOI: 10.1016/J.YJMCC.2011.07.010 [retrieved on Jul. 23, 2011] cited in the application p. 18; figures 2,3d.
Lakshmi Pulakat et al: "Cardiac Insulin Resistance and MicroRNA Modulators", Experimental Diabetes Research, vol. 2012, Jul. 31, 2011, pp. 1-12, XP55044767, ISSN: 1687-5214, DOI: 10.1155/2012/654904 the whole document.
R. Katare et al: "Transplantation of human Pericyte Progenitor Cells Improves the Repair of Infarcted Heart Through Activation of an Angiogenic Program Involving Micro-RNA-132", Circulation Research, vol. 109, No. 8, Aug. 25, 2011, pp. 894-906, XP55044864, ISSN: 0009-7330, DOI: 10.1161/ CIRCRESAHA.111.251546 the whole document.
International Search Report cited in International Application No. PCT/EP2012/067443, dated Nov. 28, 2012.

* cited by examiner

*Primary Examiner* — Kimberly Chong
(74) *Attorney, Agent, or Firm* — Rothwell, Figg, Ernst & Manbeck, P.C.

(57) ABSTRACT

The present invention refers to inhibitors of microRNAs, particularly of microRNAs miR-212 and/or miR-132 for use in medicine, particularly in the diagnosis, treatment or prevention of cardiac disorders, e.g. cardiac hypertrophy-associated or autophagic disorders, and further refers to isolated nucleic acid molecules, particularly microRNAs miR-212 and/or miR-132 and related sequences, for use in medicine, particularly human medicine, more particularly in the diagnosis, treatment or prevention of disorders involving cardiac atrophy and/or dysfunctional autophagy, e.g. cardiac cachexia.

23 Claims, 37 Drawing Sheets

SEQUENCE LISTING

```
<160> NUMBER OF SEQ ID NOS: 47

<210> SEQ ID NO 1
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miR-132

<400> SEQUENCE: 1
uaacagucua cagccauggu cg                                                  22

<210> SEQ ID NO 2
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: miR-212

<400> SEQUENCE: 2
uaacagucuc cagucacggc c                                                   21

<210> SEQ ID NO 3
<211> LENGTH: 22
<212> TYPE: RNA
<213> ORGANISM: Mus musculus
<220> FEATURE:
<221> NAME/KEY: misc_feature
<222> LOCATION: (1)..(22)
<223> OTHER INFORMATION: miR-132

<400> SEQUENCE: 3
uaacagucua cagccauggu cg                                                  22
```

```
<210> SEQ ID NO 4
<211> LENGTH: 22
<212> TYPE: RNA
<213> ORGANISM: Mus musculus
<220> FEATURE:
<221> NAME/KEY: misc_feature
<222> LOCATION: (1)..(22)
<223> OTHER INFORMATION: miR-212

<400> SEQUENCE: 4
uaacagucuc cagucacggc ca                                              22

<210> SEQ ID NO 5
<211> LENGTH: 110
<212> TYPE: RNA
<213> ORGANISM: Homo sapiens
<220> FEATURE:
<221> NAME/KEY: misc_feature
<222> LOCATION: (1)..(110)
<223> OTHER INFORMATION: Homo sapiens miR-212 stem-loop

<400> SEQUENCE: 5
cggggcaccc cgcccggaca gcgcgccggc accuuggcuc uagacugcuu acugcccggg     60
ccgcccucag uaacagucuc cagucacggc caccgacgcc uggccccgcc               110

<210> SEQ ID NO 6
<211> LENGTH: 101
<212> TYPE: RNA
<213> ORGANISM: Homo sapiens
<220> FEATURE:
<221> NAME/KEY: misc_feature
<222> LOCATION: (1)..(101)
<223> OTHER INFORMATION: Homo sapiens miR-132 stem-loop

<400> SEQUENCE: 6 ccgccccgc gucuccaggg caaccguggc uuucgauugu acuguggga acuggaggua       60 acagcuaca gccauggucg ccccgcagca cgcccacgcg c                        101

<210> SEQ ID NO 7
<211> LENGTH: 66
<212> TYPE: RNA
<213> ORGANISM: Mus musculus
<220> FEATURE:
<221> NAME/KEY: misc_feature
<222> LOCATION: (1)..(66)
<223> OTHER INFORMATION: Mus musculus miR-132 stem-loop

<400> SEQUENCE: 7
gggcaaccgu ggcuuucgau uguuacugug ggaaccggag guaacagucu acagccaugg     60
ucgccc                                                               66

<210> SEQ ID NO 8
<211> LENGTH: 91
<212> TYPE: RNA
<213> ORGANISM: Mus musculus
<220> FEATURE:
<221> NAME/KEY: misc_feature
<222> LOCATION: (1)..(91)
<223> OTHER INFORMATION: Mus musculus miR-212 stem-loop

<400> SEQUENCE: 8
gggcagcgcg ccggcaccuu ggcucuagac ugcuuacugc ccgggccgcc uucaguaaca     60
gucuccaguc acggccaccg acgccuggcc c                                   91
```

```
<210> SEQ ID NO 9
<211> LENGTH: 22
<212> TYPE: RNA
<213> ORGANISM: Artificial
<220> FEATURE:
<223> OTHER INFORMATION: antagomir against miR-132
<220> FEATURE:
<221> NAME/KEY: misc_feature
<222> LOCATION: (22)..(22)
<223> OTHER INFORMATION: n = A-chol (chol = cholesterol)

<400> SEQUENCE: 9
cgaccauggc uguagacugu un                                              22

<210> SEQ ID NO 10
<211> LENGTH: 20
<212> TYPE: DNA
<213> ORGANISM: Artificial
<220> FEATURE:
<223> OTHER INFORMATION: mouse anp forward primer

<400> SEQUENCE: 10
cctgtgtaca gtgcggtgtc                                                 20

<210> SEQ ID NO 11
<211> LENGTH: 20
<212> TYPE: DNA
<213> ORGANISM: Artificial
<220> FEATURE:
<223> OTHER INFORMATION: mouse anp reverse primer

<400> SEQUENCE: 11
cctagaagca ctgccgtctc                                                 20

<210> SEQ ID NO 12
<211> LENGTH: 20
<212> TYPE: DNA
<213> ORGANISM: Artificial
<220> FEATURE:
<223> OTHER INFORMATION: mouse bnp forward primer

<400> SEQUENCE: 12
ctgaaggtgc tgtcccagat                                                 20

<210> SEQ ID NO 13
<211> LENGTH: 20
<212> TYPE: DNA
<213> ORGANISM: Artificial
<220> FEATURE:
<223> OTHER INFORMATION: mouse bnp reverse primer

<400> SEQUENCE: 13
gttcttttgt gaggccttgg                                                 20

<210> SEQ ID NO 14
<211> LENGTH: 23
<212> TYPE: DNA
<213> ORGANISM: Artificial
<220> FEATURE:
<223> OTHER INFORMATION: mouse alpha-MHC forward primer

<400> SEQUENCE: 14
ggtccacatt cttcaggatt ctc                                             23

<210> SEQ ID NO 15
<211> LENGTH: 21
```

-continued

```
<212> TYPE: DNA
<213> ORGANISM: Artificial
<220> FEATURE:
<223> OTHER INFORMATION: mouse alpha-MHC reverse primer

<400> SEQUENCE: 15
gcgttccttc tctgactttc g                                             21

<210> SEQ ID NO 16
<211> LENGTH: 24
<212> TYPE: DNA
<213> ORGANISM: Artificial
<220> FEATURE:
<223> OTHER INFORMATION: mouse beta-MHC forward primer

<400> SEQUENCE: 16
tctcctgctg tttccttact tgct                                          24

<210> SEQ ID NO 17
<211> LENGTH: 24
<212> TYPE: DNA
<213> ORGANISM: Artificial
<220> FEATURE:
<223> OTHER INFORMATION: mouse beta-MHC reverse primer

<400> SEQUENCE: 17
caggcctgta gaagagctgt actc                                          24

<210> SEQ ID NO 18
<211> LENGTH: 20
<212> TYPE: DNA
<213> ORGANISM: Artificial
<220> FEATURE:
<223> OTHER INFORMATION: mouse gapdh forward primer

<400> SEQUENCE: 18
ttcaccacca tggagaaggc                                               20

<210> SEQ ID NO 19
<211> LENGTH: 20
<212> TYPE: DNA
<213> ORGANISM: Artificial
<220> FEATURE:
<223> OTHER INFORMATION: mouse gapdh reverse primer

<400> SEQUENCE: 19
ggcatggact gtggtcatga                                               20

<210> SEQ ID NO 20
<211> LENGTH: 20
<212> TYPE: DNA
<213> ORGANISM: Artificial
<220> FEATURE:
<223> OTHER INFORMATION: mouse foxo3 forward primer

<400> SEQUENCE: 20
caaagctggg taccaggctg                                               20

<210> SEQ ID NO 21
<211> LENGTH: 20
<212> TYPE: DNA
<213> ORGANISM: Artificial
<220> FEATURE:
<223> OTHER INFORMATION: mouse foxo3 reverse primer

<400> SEQUENCE: 21
```

```
ttccacgggt aagggcttca                                               20

<210> SEQ ID NO 22
<211> LENGTH: 22
<212> TYPE: DNA
<213> ORGANISM: Artificial
<220> FEATURE:
<223> OTHER INFORMATION: rat foxo3 forward primer

<400> SEQUENCE: 22
gatggtgcgc tgtgtgccct ac                                            22

<210> SEQ ID NO 23
<211> LENGTH: 23
<212> TYPE: DNA
<213> ORGANISM: Artificial
<220> FEATURE:
<223> OTHER INFORMATION: rat foxo3 reverse primer

<400> SEQUENCE: 23
ccaagagctc ttgccagtcc ctt                                           23

<210> SEQ ID NO 24
<211> LENGTH: 21
<212> TYPE: DNA
<213> ORGANISM: Artificial
<220> FEATURE:
<223> OTHER INFORMATION: rat lc3-promoter region (ChIP) forward primer

<400> SEQUENCE: 24
ggctggactt gaattcagaa a                                             21

<210> SEQ ID NO 25
<211> LENGTH: 20
<212> TYPE: DNA
<213> ORGANISM: Artificial
<220> FEATURE:
<223> OTHER INFORMATION: rat lc3-promoter region (ChIP) reverse primer

<400> SEQUENCE: 25
acttgctgtt ccaggtggtc                                               20

<210> SEQ ID NO 26
<211> LENGTH: 22
<212> TYPE: DNA
<213> ORGANISM: Artificial
<220> FEATURE:
<223> OTHER INFORMATION: mouse atrogin1 forward primer

<400> SEQUENCE: 26
gcaaacactg ccacattctc tc                                            22

<210> SEQ ID NO 27
<211> LENGTH: 20
<212> TYPE: DNA
<213> ORGANISM: Artificial
<220> FEATURE:
<223> OTHER INFORMATION: mouse atrogin1 reverse primer

<400> SEQUENCE: 27
cttgagggga aagtgagacg                                               20

<210> SEQ ID NO 28
<211> LENGTH: 25
<212> TYPE: DNA
<213> ORGANISM: Artificial
```

```
<220> FEATURE:
<223> OTHER INFORMATION: rat atrogin1 forward primer

<400> SEQUENCE: 28
ccatcaggag aagtggatct atgtt                                              25

<210> SEQ ID NO 29
<211> LENGTH: 26
<212> TYPE: DNA
<213> ORGANISM: Artificial
<220> FEATURE:
<223> OTHER INFORMATION: rat atrogin1 reverse primer

<400> SEQUENCE: 29
gttcatgaag ttcttttggg cgatgc                                             26

<210> SEQ ID NO 30
<211> LENGTH: 17
<212> TYPE: DNA
<213> ORGANISM: Artificial
<220> FEATURE:
<223> OTHER INFORMATION: mouse mcip1 forward primer

<400> SEQUENCE: 30
ctgcacaaga ccgagtt                                                       17

<210> SEQ ID NO 31
<211> LENGTH: 16
<212> TYPE: DNA
<213> ORGANISM: Artificial
<220> FEATURE:
<223> OTHER INFORMATION: mouse mcip1 reverse primer

<400> SEQUENCE: 31
tgtttgtcgg gattgg                                                        16

<210> SEQ ID NO 32
<211> LENGTH: 20
<212> TYPE: DNA
<213> ORGANISM: Artificial
<220> FEATURE:
<223> OTHER INFORMATION: rat mcip1 forward primer

<400> SEQUENCE: 32
agctccctga ttgcctgtgt                                                    20

<210> SEQ ID NO 33
<211> LENGTH: 20
<212> TYPE: DNA
<213> ORGANISM: Artificial
<220> FEATURE:
<223> OTHER INFORMATION: rat mcip1 reverse primer

<400> SEQUENCE: 33
tttggccctg gtctcacttt                                                    20

<210> SEQ ID NO 34
<211> LENGTH: 20
<212> TYPE: DNA
<213> ORGANISM: Artificial
<220> FEATURE:
<223> OTHER INFORMATION: mouse lc3b forward primer

<400> SEQUENCE: 34
cgtcctggac aagaccaagt                                                    20
```

```
<210> SEQ ID NO 35
<211> LENGTH: 20
<212> TYPE: DNA
<213> ORGANISM: Artificial
<220> FEATURE:
<223> OTHER INFORMATION: mouse lc3b reverse primer

<400> SEQUENCE: 35
attgctgtcc cgaatgtctc                                                 20

<210> SEQ ID NO 36
<211> LENGTH: 20
<212> TYPE: DNA
<213> ORGANISM: Artificial
<220> FEATURE:
<223> OTHER INFORMATION: mouse ulk2 forward primer

<400> SEQUENCE: 36
cagccctgga tgagatgttt                                                 20

<210> SEQ ID NO 37
<211> LENGTH: 20
<212> TYPE: DNA
<213> ORGANISM: Artificial
<220> FEATURE:
<223> OTHER INFORMATION: mouse ulk2 reverse primer

<400> SEQUENCE: 37
ggatgggtga cagaaccaag                                                 20

<210> SEQ ID NO 38
<211> LENGTH: 20
<212> TYPE: DNA
<213> ORGANISM: Artificial
<220> FEATURE:
<223> OTHER INFORMATION: mouse atg12 forward primer

<400> SEQUENCE: 38
ggcctcggaa cagttgttta                                                 20

<210> SEQ ID NO 39
<211> LENGTH: 20
<212> TYPE: DNA
<213> ORGANISM: Artificial
<220> FEATURE:
<223> OTHER INFORMATION: mouse atg12 reverse primer

<400> SEQUENCE: 39
cagcaccgaa atgtctctga                                                 20

<210> SEQ ID NO 40
<211> LENGTH: 20
<212> TYPE: DNA
<213> ORGANISM: Artificial
<220> FEATURE:
<223> OTHER INFORMATION: mouse beclin1 forward primer

<400> SEQUENCE: 40
ggccaataag atgggtctga                                                 20

<210> SEQ ID NO 41
<211> LENGTH: 20
<212> TYPE: DNA
<213> ORGANISM: Artificial
<220> FEATURE:
<223> OTHER INFORMATION: mouse beclin1 reverse primer
```

```
<400> SEQUENCE: 41
cactgcctcc agtgtcttca                                              20

<210> SEQ ID NO 42
<211> LENGTH: 20
<212> TYPE: DNA
<213> ORGANISM: Artificial
<220> FEATURE:
<223> OTHER INFORMATION: mouse plk3c3 forward primer

<400> SEQUENCE: 42
tgtcagatga ggaggctgtg                                              20

<210> SEQ ID NO 43
<211> LENGTH: 20
<212> TYPE: DNA
<213> ORGANISM: Artificial
<220> FEATURE:
<223> OTHER INFORMATION: mouse plk3c3 reverse primer

<400> SEQUENCE: 43
ccaggcacga cgtaacttct                                              20

<210> SEQ ID NO 44
<211> LENGTH: 20
<212> TYPE: DNA
<213> ORGANISM: Artificial
<220> FEATURE:
<223> OTHER INFORMATION: mouse bnip3 forward primer

<400> SEQUENCE: 44
gaactgcact tcagcaatgg                                              20

<210> SEQ ID NO 45
<211> LENGTH: 20
<212> TYPE: DNA
<213> ORGANISM: Artificial
<220> FEATURE:
<223> OTHER INFORMATION: mouse bnip3 reverse primer

<400> SEQUENCE: 45
atttcagctc tgttggtatc                                              20

<210> SEQ ID NO 46
<211> LENGTH: 24
<212> TYPE: DNA
<213> ORGANISM: Artificial
<220> FEATURE:
<223> OTHER INFORMATION: mouse atg5 forward primer

<400> SEQUENCE: 46
gacaaagatg tgcttcgaga tgtg                                         24

<210> SEQ ID NO 47
<211> LENGTH: 23
<212> TYPE: DNA
<213> ORGANISM: Artificial
<220> FEATURE:
<223> OTHER INFORMATION: mouse atg5 reverse primer

<400> SEQUENCE: 47
ataatgccat ttcaggggtg tgc                                          23
```

MIRNA-212/132 FAMILY AS A THERAPEUTIC TARGET

CROSS REFERENCE TO RELATED APPLICATION

Figure 1:
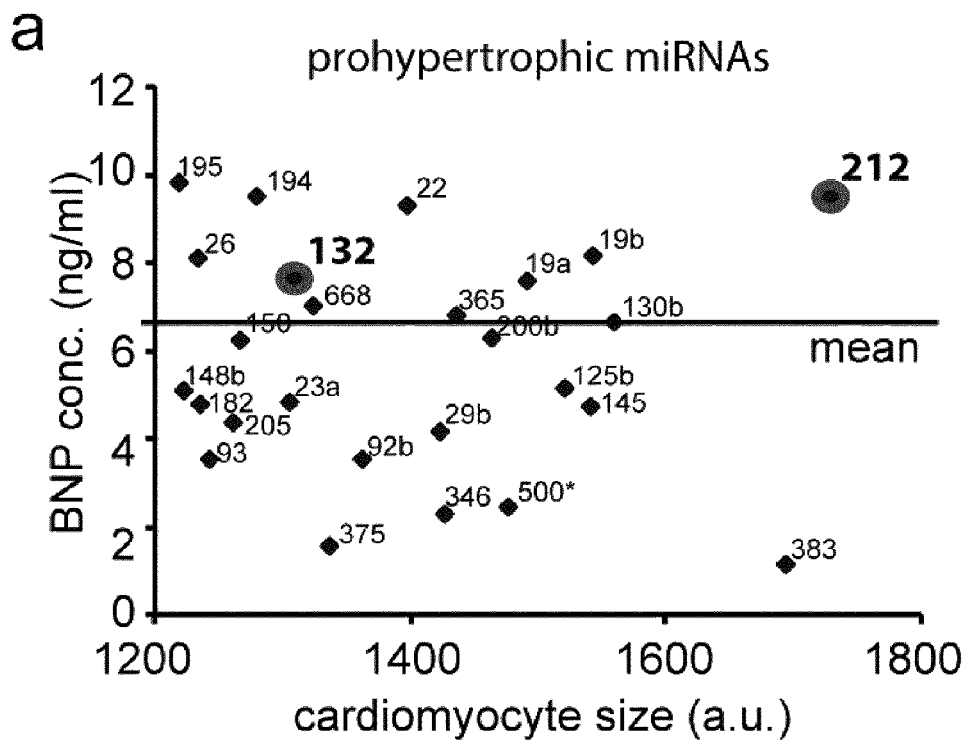
Figure 1:
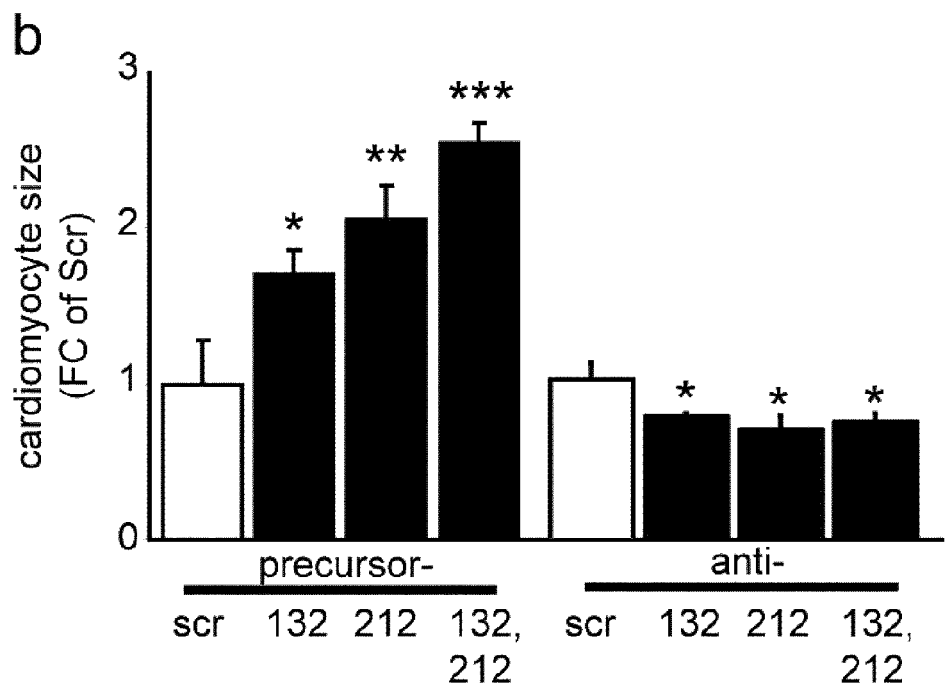
Figure 1:
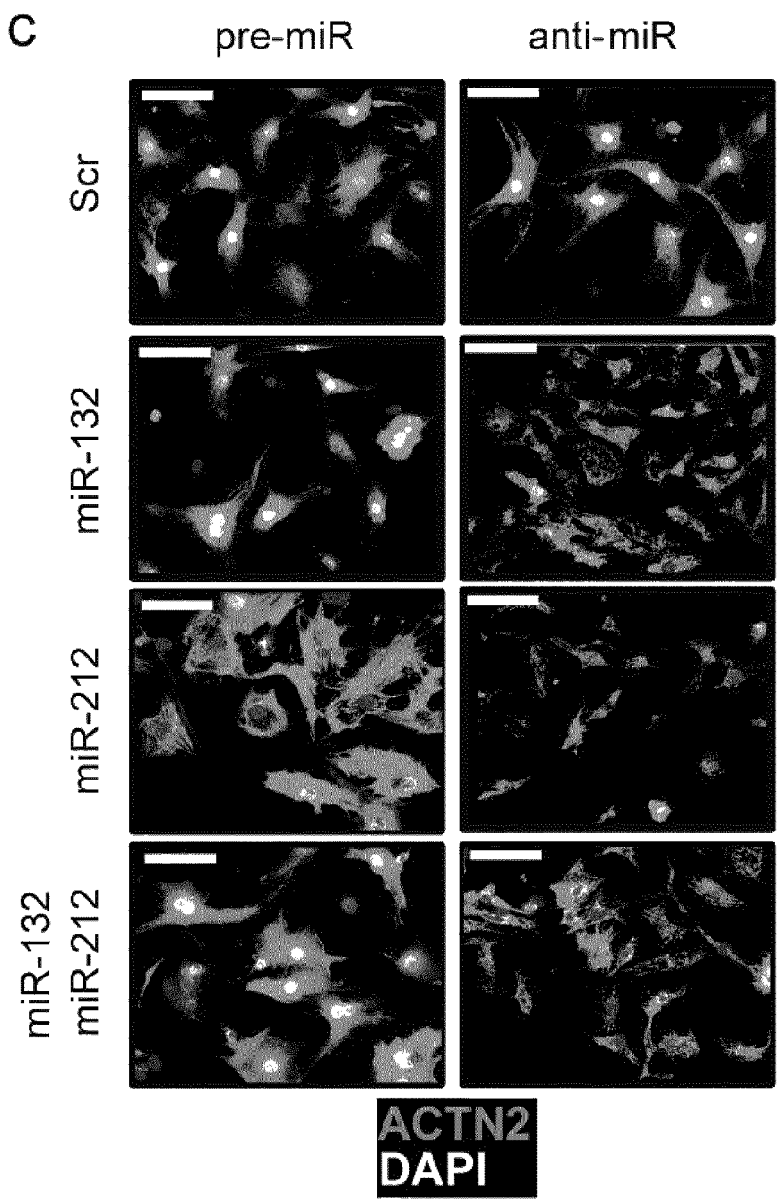
Figure 1:
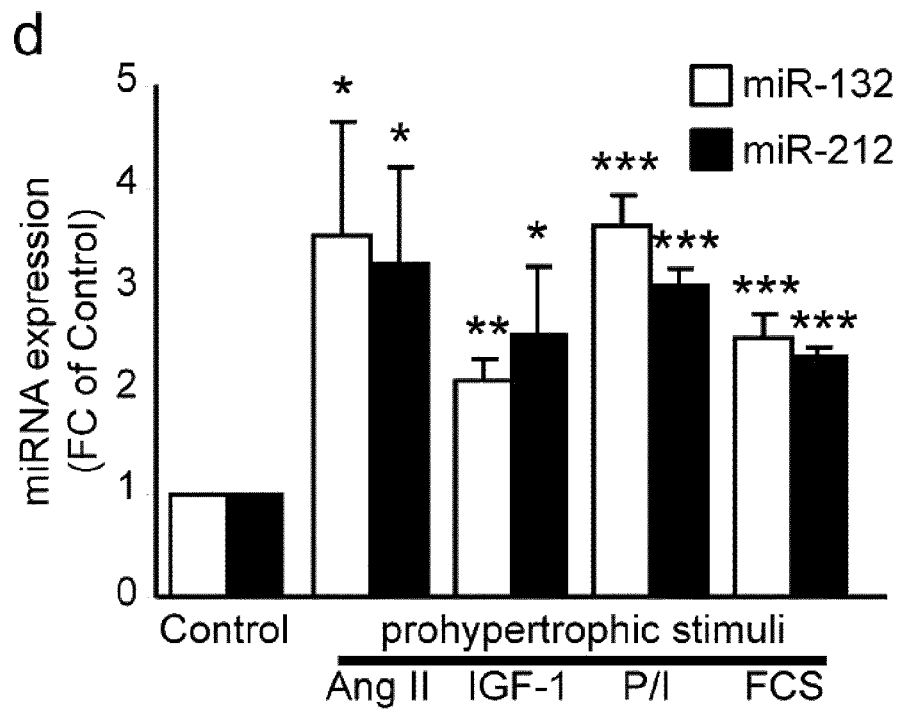
Figure 1:
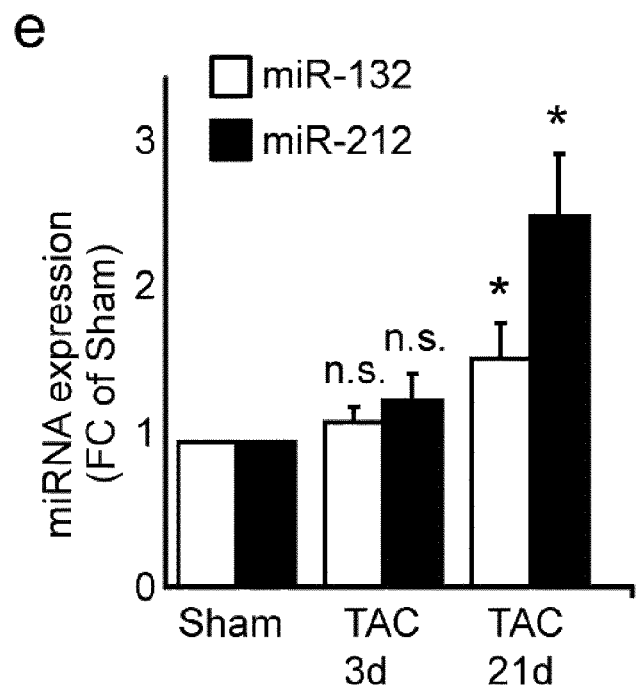
Figure 1:
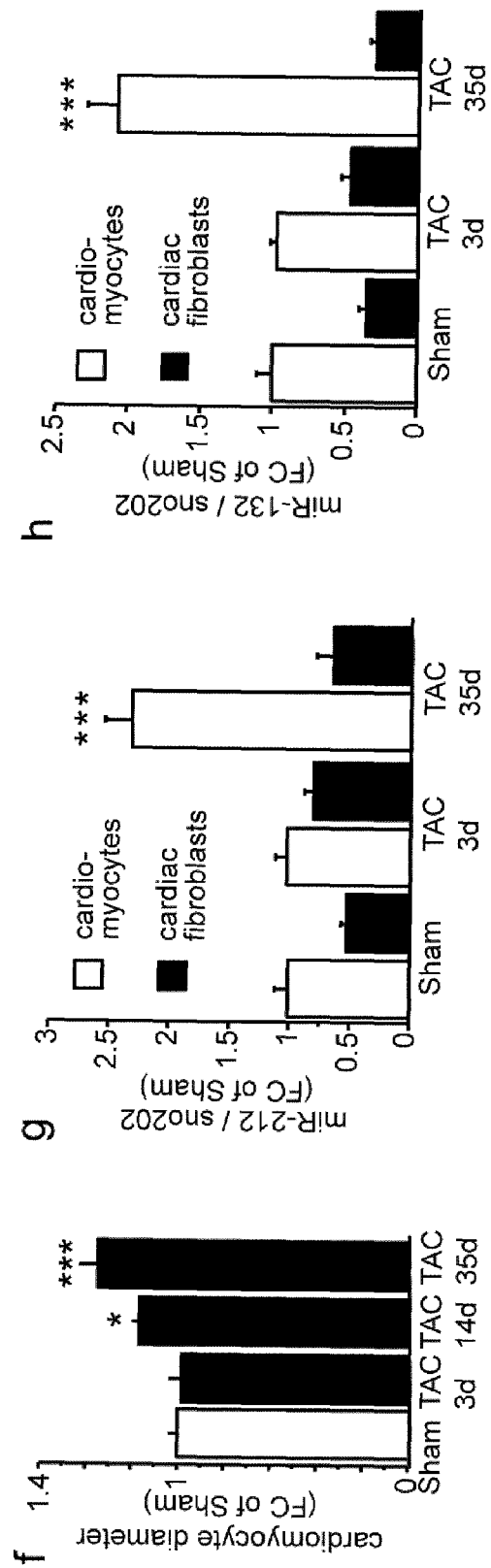

This application is a 35 U.S.C. 371 National Phase Entry Application from PCT/EP20123/067443, filed Sep. 6, 2012, which claims the benefit of U.S. Ser. No. 61/531,156 filed on Sep. 6, 2011, the disclosure of which is incorporated herein in its entirety by reference.

The present invention refers to inhibitors of microRNAs, particularly of microRNAs miR-212 and/or miR-132 for use in medicine, particularly in the treatment or prevention of cardiac disorders, e.g. cardiac hypertrophy-associated or autophagic disorders.

The invention further relates to isolated nucleic acid molecules, particularly microRNAs miR-212 and/or miR-132 and related sequences, for use in medicine, particularly human medicine, more particularly in the diagnosis, treatment or prevention of disorders involving cardiac atrophy and/or dysfunctional autophagy, e.g. cardiac cachexia.

Heart failure is one of the leading pathological causes of mortality in the world. The currently used therapeutic pharmacologic options for heart failure include angiotensin-modulating agents, β-blockers, diuretics, aldosterone antagonists, vasodilators, or ionotrophic agents. Although several clinical studies have shown significant decreases in heart failure-induced mortality rates for all these agents, the 5-year mortality rate remains unacceptably at almost 50%. Thus, there is a great urge to develop novel and more efficient therapeutic approaches for heart failure.

Pathological hypertrophic growth of cardiomyocytes can lead to the development of cardiac remodeling, heart failure and sudden cardiac death. Hypertrophic growth of cardiomyocytes is a response to increased cardiac wall stress caused by cardiac volume and/or pressure overload. Initially, cardiac hypertrophy is a compensatory mechanism aiming to decrease wall stress and to increase cardiac output. However, prolonged cardiac hypertrophy progresses to contractile dysfunction, cardiac decompensation and finally heart failure (Hill and Olson, 2008; Barry and Townsend, 2010). The transition from physiological to pathological hypertrophy can occur depending on many factors including myocyte loss through apoptosis or necrosis, defects in contractile response, deregulated calcium homeostasis, desensitization of adrenergic receptors, or cardiac fibrosis (Hill and Olson, 2008; Barry and Townsend, 2010). Hypertrophic signaling is largely mediated by the insulin signaling pathway (DeBosch and Muslin, 2008; Barry and Townsend, 2010). Both insulin and insulin-like growth factor-1 (IGF-1) activate pro-hypertrophic pathways in cardiomyocytes via the IGF-1 receptor, which activates the phosphoinositine-3-kinase (PI3K) (McMullen et al., 2004). PI3K activity leads to the activation of the serine/threonine kinase Akt via its phosphorylation and active Akt phosphorylates anti-hypertrophic FoxO transcription factors leading to their de-stabilization and prevention of nuclear localization (Datta et al., 1999; Skurk et al., 2005; Ronnebaum and Patterson, 2010). In contrast, acetylation of FoxO factors by sirtuin-1 (Sirt-1) leads to their stabilization and nuclear translocation (Frescas et al., 2005). Stabilized FoxO transcription factors are localized in the nucleus in order to regulate the expression of anti-hypertrophic genes. The anti-hypertrophic functions of FoxO proteins are largely mediated through suppression of the pro-hypertrophic calcineurin signaling pathway via the expression of anti-hypertrophic gene targets of FoxO factors, such as atrogin-1 (Ni et al., 2006; Ronnebaum and Patterson, 2010; Glas, 2010). Moreover, FoxO transcription factors also induce apoptosis and regulate autophagy in cardiomyocytes (Ronnebaum and Patterson, 2010).

Cachexia is one of the most visible and devastating consequences of human disease that is seen in several chronic human diseases, including cancer, AIDS, thyrotoxicosis, and rheumatoid arthritis (Anker & Coats, 1999). It is thought to be related to loss of appetite (anorexia), anemia, and metabolic abnormalities. The presence of general weight loss in heart failure patients has been termed cardiac cachexia. Anker & Coats (1999) suggested that "clinical cardiac cachexia" be defined as a condition wherein a weight loss of >7.5% as compared to the previous normal weight exists over a duration of at least six months in patients with chronic heart failure (CHF), who do not show signs of other primary cachectic states such as cancer, thyroid disease or severe liver disease. A further classification into severe (>15% weight loss or >7.5% weight loss and <85% of ideal body weight) and early or moderate cachexia (>7.5% to ≤15% weight loss and ≥85% of ideal body weight) has also been suggested (Anker & Coats, 1999).

The detection of cardiac cachexia, which is also referred to as body wasting, is a strong independent risk factor for mortality in patients with CHF, with a 18 month mortality rate of 50%, mainly because of the absence of specific therapy for cachectic CHF patients (Anker et al., 1997; Anker & Coats, 1999).

Autophagy is a catabolic process, which is initiated upon nutrient limitation, cellular stress, reactive oxygen species (ROS), or accumulation of damaged organelles or protein aggregates. The role of autophagy in the maintenance of cardiac homeostasis was recently evaluated (Gottlieb and Mentzer, 2010). For instance, autophagic elimination of damaged organelles, especially mitochondria, is crucial for proper heart function, whereas exaggerated autophagic activity may foster heart failure development (Gottlieb and Gustafsson, 2011). Intensified autophagic degradation may lead to autophagic cell death, which is different than apoptosis since it does not require caspase activation (Ronnebaum and Patterson, 2010). Therefore, a delicate balance of autophagy maintains cardiac homeostasis, whereas the misbalance leads to heart failure progression (Cao et al., 2011).

MicroRNAs (miRNAs) are small RNA molecules regulating the gene expression of their target genes at post-transcriptional levels. By their direct regulation on these target genes, microRNAs can regulate several biological processes and signaling pathways. The dysfunction of several microRNAs has been shown in many diseases, including cancer, neurodegenerative disorders and cardiovascular diseases. During recent years, the possible therapeutical power of microRNAs emerged by the successful applications of intravenous injections of either precursor microRNAs or inhibitors of microRNAs (antagomirs), which lead to the regulation of genes or pathways that were dysfunctional in specific disease conditions. Currently, many therapeutical approaches based on modulation of individual microRNA expression are under investigation.

MiRNAs exert their function based on the base-complementation mainly with 3' untranslated regions (UTRs) of their target mRNAs, leading to the recognition of these targeted mRNAs by the RNA-induced silencing complex (RISC) associated with the miRNAs (Valencia-Sanchez et al., 2006; Bartel, 2009). Duplex formation by base complementarity between the miRNA and mainly the 3' region of the target mRNAs, leads either to the degradation of the mRNAs or downregulation of protein translation via association with RNA-induced silencing complex (RISC) (Valencia-Sanchez et al., 2006; Bartel, 2009). The functional importance of miRNAs in the maintenance of cardiac function and homeostasis was demonstrated in mice having heart-specific genetic deletion of Dgcr8 or Dicer, which are the key enzymes in the miRNA biogenesis pathway. These mice died prematurely due to cardiomyopathy associated with myofibrial disarray, fibrosis, and ventricular dysfunction (Chen, 2008; da Costa Martins, 2008; Rao, 2009). However, to date the functional roles of only few individual miRNAs have been shown for heart development or cardiac homeostasis (van Rooij et al., 2007; Zhao et al., 2007; Ventura et al., 2008; Liu et al., 2008; Callis et al., 2009; van Rooij et al., 2009). Therefore, the generation of loss-of- and gain-of-function mutants for other individual miRNAs is necessary to gain further mechanistic insights into miRNA-dependent regulation of cardiac function and homeostasis.

After birth, many organ systems undergo substantial functional modifications, accomplished by a postnatal switch from 'fetal' to 'adult' gene programs. During heart failure due to hemodynamic or metabolic stress, the 'fetal' gene program gets reactivated in the adult heart. The re-expression of genes that are normally repressed in adult cardiomyocytes is an adaptation to altered energy demands and hypertrophic enlargements of cardiomyocytes (Barry and Townsend, 2010; Taegtmeyer et al., 2010).

MiR-212 has been described to be pro-hypertrophic and highly upregulated in failing human myocardium (Thum et al., 2007; Bauersachs and Thum, 2007; Thum et al., 2008).

The miR-212/132 gene family is highly conserved in vertebrates, including fish and mammals. We have previously shown that genetic deletion of miR-212/132 in mice leads to the impairment of pubertal mammary gland development (Ucar et al., 2010; Ucar et al., 2011). It was also recently shown that the targeted genetic deletion of miR-212/132 in the hippocampus of mice leads to impaired dendritic maturation of hippocampal neurons (Magill et al., 2010). Furthermore, transgenic overexpression of miR-132 in mouse brain, influences behavioral functions including circadian clock regulation and novel object recognition (Hansen et al., 2010; Alvarez-Saavedra et al., 2011).

An assay format was developed that allows simultaneous analysis of miRNA molecules with regard to the phenotypic effect on primary rat cardiomyocytes. In this assay, the pro-hypertrophic potential of miR-212 was confirmed. However, no correlation between endogenous miRNA expression and the pro-hypertrophic potential was found, disfavoring the presumption that strong endogenous expression correlates with activity (Jentzsch et al., 2011).

Thus, the in vivo functional roles of miR-212/132 have not yet been explored in the living organisms, particularly in pathological situations. Here, we show that hypertrophic conditions induce the expression of miR-212/132 family in cardiomyocytes and both miR-212 and miR-132 regulate cardiac hypertrophy and autophagy in cardiomyocytes. More particularly, it was shown that hypertrophic stimuli lead to the upregulation of miR-212 and miR-132 expression in cardiomyocytes. Upregulation of both miRs is necessary and sufficient to drive the hypertrophic growth of cardiomyocytes. MiR-212/132 null mice are protected from pressure-overload induced heart failure, whereas cardiomyocyte-specific overexpression of the miR-212/132 family leads to pathological cardiac hypertrophy, heart failure and lethality in mice. Both miR-212 and miR-132 directly target the anti-hypertrophic and pro-autophagic FoxO3 transcription factor. Thus, miR-212/132 overexpression in cardiomyocytes leads to the down-regulation of FoxO3 expression and consequently to a hyperactivation of pro-hypertrophic calcineurin signaling and NFAT transcriptional activity, as well as to a decrease in autophagy. Pharmacologic blockade by antagomir-injection against miR-132 rescued pressure-overload induced heart failure in mice, offering a therapeutic approach for pathological cardiac hypertrophy.

Thus, a subject-matter of the present invention is an inhibitor of miR-212 and/or miR-132 for use in medicine, e.g. in veterinary medicine or in human medicine.

A further subject-matter of the present invention is a method for the prevention or treatment of a cardiac disorder comprising administering to a subject in need thereof a therapeutically effective amount of at least one inhibitor of miR-212 and or miR-132.

In a preferred embodiment, the invention refers to an inhibitor of human miR-212 and/or miR-132 (miR-132 *Homo sapiens* UAACAGUCUACAGCCAUGGUCG, miR-212 *Homo sapiens* UAACAGUCUCCAGUCACGGCC) (SEQ ID NO: 1 and 2). Another preferred embodiment relates to an inhibitor of mouse miR-212 and/or miR-132 (miR-132 *Mus musculus* UAACAGUCUACAGCCAUGGUCG, miR-212 *Mus musculus* UAACAGUCUCCAGUCACGGCCA) (SEQ ID NO: 3; SEQ ID NO: 4). The sequences of human and mouse miR-132 are identical.

The inhibitor is preferably a nucleic acid molecule, including RNA molecules, DNA molecules and modified nucleic acid molecules comprising at least one modified nucleic acid building block. Preferably, the inhibitor is an RNA molecule having at least one modified building block. The nucleic acid inhibitor of the present invention preferably has sufficient complementarity to miR-212 and/or miR-132, particularly to human miR-212 and/or human miR-132 to form a hybrid under physiological conditions, thereby reducing and/or abolishing the pro-hypertrophic and/or anti-autophagic effect of miR-212 and/or miR-132.

The inhibitor may be a single-stranded or double-stranded nucleic acid molecule or a nucleic acid molecule comprising single-stranded and double-stranded portions. The nucleic acid molecule may be conjugated to heterologous molecules, e.g. non-nucleic acid molecules such as fatty acids, lipids, saccharides, peptides, proteins, antibodies, nanoparticles, peptide nucleic acids (PNAs), locked nucleotide analogues (LNAs).

In a preferred embodiment, the nucleic acid inhibitor may comprise at least one modified nucleotide building block. Modified nucleotide building blocks may be selected from nucleobase-, sugar- and backbone-modified building blocks and combinations thereof, i.e. building blocks having several modifications, e.g. a sugar and a backbone modification.

Nucleobase-modified building blocks comprise a non-standard nucleobase instead of a standard nucleobase (e.g. adenine, guanine, cytosine, thymine or uracil) such as a uracil or cytosines modified at the 5-position, e.g 5-methylcytosine, 5-(2-amino)propyluracil, 5-bromouracil, adenines or guanines modified at the 8-position, e.g. 8-bromoguanine, deazapurine nucleobases, e.g. 7-deaza-adenine and O— or N-alkylated nucleobases, e.g. N6 alkyl-adenine.

Further, the invention encompasses sugar-modified building blocks, particularly sugar-modified ribonucleotide building blocks, wherein the 2'OH group is replaced by a group selected from H, OR, R, halo, SH, SR, NH, NHR, NR$_2$ or CN, wherein R is $C_1$-$C_6$ alkyl, $C_2$-$C_6$ alkenyl or $C_2$-$C_6$ alkynyl and halo is F, Cl, Br or I. Further preferred sugar-modified nucleotides are selected from LNA or morpholino nucleotides.

In preferred backbone-modified building blocks, the phosphoester group connecting to adjacent building blocks is replaced by a modified group, e.g. by replacing one or more O atoms of the phosphoester group by S, Se, NR or $CR_2$, wherein R is as defined above. It should be noted that the above modifications may be combined.

In one embodiment, the inhibitor may be a double-stranded RNA molecule capable of RNA interference which is directed against a transcript comprising miR-212 and/or miR-132 or precursors thereof, e.g. an siRNA molecule which is a double-stranded RNA molecule, wherein each strand has a length of 15-30, preferably 19-25 nucleotides, which optionally has at least one 3'-overhang having a length of 1-5 or 1-3 nucleotides. Typical siRNA molecules are for example described in WO 02/044321, the content of which is incorporated herein by reference.

In another preferred embodiment, the nucleic acid inhibitor is an antagomir, which is a single-stranded RNA molecule having a length of from 10 to 30 nucleotides, preferably from 12 to 25 nucleotides and even more preferably from 15 to 22 nucleotides. The antagomir may be perfectly complementary to its specific miRNA target with mispairing at the cleavage side of Ago2 and/or the presence of at least one modified building block to inhibit Ago2 cleavage. Antagomirs are for example disclosed in Krützfeldt et al., 2005, Czech, 2006 or Fiedler et al., 2011, the contents of which are incorporated herein by reference.

Preferred antagomirs are cholesterol-conjugated, LNA-conjugated or FMOE-conjugated. In a particular preferred embodiment those antagomirs are directed against miR-212 and/or miR-132 as described above.

Preferably, a nucleic acid inhibitor molecule has a sufficient sequence complementarity to miR-212 and/or miR-132 and/or a precursor thereof in order to mediate target-specific inhibition, e.g. by forming a double-stranded hybrid with the target. Preferably, the sequence has a complementarity of at least 50%, at least 70%, at least 80%, at least 85%, at least 90%, at least 95% or up to 100% in the portion which corresponds to the target.

The nucleic acid inhibitors of the invention may be prepared by conventional methods, e.g. by chemical synthesis methods usually involving solid-phase synthesis according to standard protocols. The inhibitors can also be prepared by enzymatic transcription from synthetic DNA templates or from DNA plasmids, e.g. isolated from recombinant bacteria. Typically, phage RNA polymerases are used, such as T7, T3 or SP6 RNA polymerase.

The inhibitor of the present invention is useful in the prevention or treatment of cardiac disorders, particularly of cardiac hypertrophy-associated or autophagic disorders.

More particularly, the inhibitor is useful in the prevention or treatment of contractile dysfunction, cardiac decompensation, heart failure or for preventing cardiac remodeling after myocardial infarction, myocarditis, valvular heart diseases such as aortic stenosis or mitral valve insufficiency, genetic cardiac disorders with cardiac hypertrophy, e.g. hypertrophic non-obstructive and obstructive cardiomyopathy, Fabry disease.

With regard to autophagic disorders, this term encompasses disorders in which patients show dysfunctional autophagy, in particular reduced or absent autophagy. Diseases and conditions that may be treated by administering the inhibitor according to the invention include neurodegenerative diseases such as Huntington's Disease, Parkinson's Disease, Alzheimer's Disease, and spinocerebellar ataxia; liver diseases; muscle diseases such as Danon disease, Pompe disease, sporadic inclusion body myositis, limb girdle muscular dystrophy, in particular of type 2B, and Miyoshi myopathy; cancer, including breast, colon, ovarian, and prostate cancer, follicular lymphoma, epithelial cancers as a consequence of Peutz-Jeghers syndrome; autoimmune disorders, e.g. Crohn's disease; infectious diseases; cardiac disorders including skeletal and cardiac muscle degeneration and further disorders including aging, Paget disease, motor neuron disease with spinal and bulbar muscular atrophy, Batten disease, and tuberous sclerosis complex.

In preferred embodiments, administration of the inhibitor pharmacologically activates autophagy in the patient.

The inhibitor is administered to a subject in need thereof, particularly to a human patient suffering from the above-indicated diseases.

In some embodiments, the inhibitor is useful for administration to patients selected from patients having an increased risk of heart failure, patients suffering from (congestive) heart failure, post-myocardial infarction patients or patients with congenital heart diseases associated to cardiac hypertrophy, such as pulmonal vein stenosis, atrial or ventricular septum defects.

Preferably, the invention encompasses diagnosing and/or monitoring the amount and/or activity of miR-212 and/or miR-132 before, during and/or after administration of the inhibitor.

The inhibitor may be administered as a pharmaceutical composition comprising a pharmacologically acceptable carrier and diluent. Administration may be carried out by known methods, wherein the inhibitor is introduced into the desired target cell in vitro or in vivo. Suitable administration methods include injection, viral transfer, use of liposomes, e.g. cationic liposomes, oral intake and/or dermal application.

For pharmaceutical applications, the composition may be in the form of a solution, e.g. an injectable solution, emulsion, suspension or the like. The composition may be administered in any suitable way, e.g. by injection, infusion, oral intake and/or by dermal application. The carrier may be any suitable pharmaceutical carrier. Preferably, a carrier is used which is capable of increasing the efficacy of the RNA molecules to enter the target cells. Suitable examples of such carriers are liposomes.

The inhibitor is administered in a pharmaceutically effective dosage, which may be in the range of 0.001 µg/kg body weight to 1 mg/kg body weight depending on the route of administration and the type or severity of the disease.

The inhibitor of the present invention may comprise a single type of inhibitor molecule or a plurality of different inhibitor molecules, e.g. a plurality of different siRNA molecules and/or antagomirs. For example, an inhibitor of miR-212, e.g. an antagomir, may be combined with an inhibitor of miR-132, e.g. an antagomir.

The inhibitor may be administered as a monotherapy or in combination with a further different medicament, particularly a medicament suitable for the prevention or treatment of cardiac disorders as described above. Examples of further medicaments are angiotensin-modulating agents, β-blockers, diuretics, aldosterone antagonists, vasodilators, ionotrophic agents, statins or combinations thereof.

In a still further aspect, the present invention relates to an isolated nucleic acid molecule comprising (a) a nucleotide sequence as shown in SEQ ID NO.: 1, SEQ ID NO.: 2, SEQ ID NO.: 3 and/or SEQ ID NO: 4, or a precursor of SEQ ID NO.: 1, SEQ ID NO.: 2, SEQ ID NO.: 3 and/or SEQ ID NO: 4, and/or (b) a nucleotide sequence which is the complement of (a), and/or (c) a nucleotide sequence which has an identity of at least 80% to a sequence of (a) or (b), and/or (d) a nucleotide sequence which hybridizes under stringent conditions to a sequence of (a), (b) and/or (c), for use in medicine, particularly in human medicine.

In a preferred embodiment, the isolated nucleic acid molecule has a sequence identity of at least 90%, particularly at least 95%, to a nucleotide sequence as shown in SEQ ID NO.: 1, SEQ ID NO.: 2, SEQ ID NO.: 3 and/or SEQ ID NO: 4, or to a precursor of SEQ ID NO.: 1, SEQ ID NO.: 2, SEQ ID NO.: 3 and/or SEQ ID NO: 4, or to a nucleotide sequence which is the complement of any one of SEQ ID NOs.: 1, 2, 3 and/or 4 or a precursor thereof. In particular, a precursor of SEQ ID NO: 1, 2, 3, or 4 may have the sequence as shown in one of SEQ ID NOs.: 5, 6, 7, and/or 8.

The percent sequence identity may be determined according to the following formula as follows:

$$I = n:L$$

wherein I is the identity in percent, n is the number of identical nucleotides between a given sequence and a comparative sequence as shown in SEQ ID NOs.: 1-4 or their precursors, or a complement of any one of SEQ ID NOs.: 1, 2, 3, and/or 4 or a precursor thereof, and L is the length of the comparative sequence. Importantly, when calculating the percent sequence identity according to this formula, an alignment of the two sequences shall be carried out without gaps between complementary portions. The nucleic acid of the present invention preferably has a sufficient sequence identity and/or sequence complementarity to miR-212 and/or miR-132, particularly to human miR-212 and/or human miR-132 to be able to compensate for or inhibit miR-212 and/or miR-132 function under physiological conditions, thereby providing, restoring, enhancing and/or inhibiting the pro-hypertrophic and/or anti-autophagic effect of miR-212 and/or miR-132.

Stringent hybridization conditions comprise washing for 1 h in 1×SSC and 0.1% SDS at 45° C., preferably at 48° C. and more preferably at 50° C., particularly for 1 h in 0.2×SSC and 0.1% SDS.

The isolated nucleic acid molecule according to the invention may be a single-stranded or double-stranded nucleic acid molecule or a nucleic acid molecule comprising single-stranded and double-stranded portions. The nucleic acid molecule may be conjugated to heterologous molecules, e.g. non-nucleic acid molecules such as fatty acids, lipids, saccharides, peptides, proteins, antibodies, nanoparticles, peptide nucleic acids (PNAs), locked nucleotide analogues (LNAs).

In a preferred embodiment, the isolated nucleic acid molecule is a microRNA (miRNA, miR) molecule or a precursor or an analog thereof. miRNA molecules as such are usually single-stranded molecules, while a miRNA-precursor is usually an at least partially self-complementary molecule capable of forming distinct single-stranded and double-stranded portions, e.g. stem- and loop-structures. DNA molecules encoding the miRNAs and miRNA precursor molecules are also usually present as double-stranded molecules, e.g. in the form of a PCR product or on a plasmid.

The isolated nucleic acid molecule according to the invention preferably has a length of from 15 to 150 nucleotides (nt). Primary transcripts, from which miRNA precursors may be generated, can also have a length of >150 nt and up to 5000 nt. In particular, mature miRNA molecules have a length of from 18-25 nucleotides, preferably 19-24 nt, more preferably 21, 22 or 23 nt, and miRNA precursor molecules have a length of 50-120 nucleotides, preferably 60-110 nt.

Most preferably, an miRNA molecule for use according to the invention has a length of 21 or 22 nucleotides.

In a further preferred embodiment, the isolated nucleic acid molecule for use according to the invention is an RNA molecule, which may comprise at least one modified building block. Modified nucleotide building blocks may be selected from nucleobase-, sugar- and backbone-modified building blocks and combinations thereof, i.e. building blocks having several modifications, e.g. a sugar and a backbone modification.

Nucleobase-modified building blocks comprise a non-standard nucleobase instead of a standard nucleobase (e.g. adenine, guanine, cytosine, thymine or uracil) such as a uracil or cytosines modified at the 5-position, e.g 5-methylcytosine, 5-(2-amino)propyluracil, 5-bromouracil, adenines or guanines modified at the 8-position, e.g. 8-bromoguanine, deazapurine nucleobases, e.g. 7-deaza-adenine and O— or N-alkylated nucleobases, e.g. N6 alkyl-adenine.

Further, the invention encompasses sugar-modified building blocks, particularly sugar-modified ribonucleotide building blocks, wherein the 2'OH group is replaced by a group selected from H, OR, R, halo, SH, SR, NH, NHR, $NR_2$ or CN, wherein R is $C_1$-$C_6$ alkyl, $C_2$-$C_6$ alkenyl or $C_2$-$C_6$ alkynyl and halo is F, Cl, Br or I. Further preferred sugar-modified nucleotides are selected from LNA or morpholino nucleotides.

In preferred backbone-modified building blocks, the phosphoester group connecting to adjacent building blocks is replaced by a modified group, e.g. by replacing one or more O atoms of the phosphoester group by S, Se, NR or $CR_2$, wherein R is as defined above. It should be noted that the above modifications may be combined.

The nucleic acid molecules for use according to the invention may be chemically synthesized. Methods for chemical synthesis of nucleic acids are known to the person skilled in the art of nucleic acid biochemistry.

Alternatively, the nucleic acid molecules may be obtained e.g. by recombinant methods, such as enzymatic transcription from synthetic DNA-templates (e.g. PCR products) or from plasmids isolated from recombinant organisms, e.g. bacteria or yeast strains. For transcription, phage RNA-polymerases are typically used, e.g. T7, T3 or SP6 RNA-polymerases.

The nucleic acid molecules may also be obtained via a recombinant expression vector comprising a recombinant nucleic acid operatively linked to an expression control sequence, wherein expression, i.e. transcription and optionally further processing results in a miRNA-molecule or miRNA precursor molecule as described above. The vector is preferably a DNA-vector, e.g. a viral vector or a plasmid, particularly an expression vector suitable for nucleic acid expression in eukaryotic, more particularly mammalian cells. The recombinant nucleic acid contained in said vector may be a sequence which results in the transcription of the miRNA-molecule as such, a precursor or a primary transcript thereof, which may be further processed to give the miRNA-molecule.

The isolated nucleic acid molecules are useful in the diagnosis, treatment or prevention of disorders, in particular cardiac disorders, which involve dysfunctional autophagy, cardiac atrophy, and/or cardiac hypertrophy.

More particularly, the isolated nucleic acid molecules are useful in the diagnosis, treatment or prevention of disorders involving cardiac atrophy and/or exaggerated autophagy. Examples for such disorders are cancer, body wasting associated with cancer, anorexia, and/or bulimia.

In a preferred embodiment, the isolated nucleic acid molecule according to the invention is for use in the diagnosis, treatment or prevention of cardiac cachexia.

The isolated nucleic acid molecules are administered to a subject in need thereof, particularly to a human patient suffering from one or more of the above-indicated diseases.

In some embodiments, the nucleic acid molecules are for administration to patients selected from: (i) patients having an increased risk for or suffering from autophagic disorders, (ii) patients having an increased risk for or suffering from cardiac cachexia, (iii) patients having an increased risk for or suffering from cardiac atrophy.

Preferably, the invention encompasses diagnosing and/or monitoring the amount and/or activity of miR-212 and/or miR-132 before, during and/or after administration of the nucleic acid molecules.

The inhibitor may be administered alone or as a pharmaceutical composition comprising a pharmacologically acceptable carrier and/or diluent and optionally further excipients. Administration may be carried out by known methods, wherein the nucleic acid molecule, e.g. a miRNA, is introduced into the desired target cell in vitro or in vivo. Suitable administration methods include injection, viral transfer, use of liposomes, e.g. cationic liposomes, oral intake and/or dermal application.

For pharmaceutical applications, the composition may be in the form of a solution, e.g. an injectable solution, emulsion, suspension or the like. The composition may be administered in any suitable way, e.g. by injection, infusion, oral intake and/or by dermal application. The carrier may be any suitable pharmaceutical carrier. Preferably, a carrier is used which is capable of increasing the efficacy of the RNA molecules to enter the target cells. Suitable examples of such carriers are liposomes.

The inhibitor is administered in a pharmaceutically effective dosage, which may be in the range of 0.001 µg/kg body weight to 1 mg/kg body weight depending on the route of administration and the type or severity of the disease.

In further preferred embodiments, the nucleic acid molecule is administered in combination with a further medicament; in particular, the further medicament may be useful in the treatment of the same disease. Examples of further medicaments are angiotensin-modulating agents, β-blockers, diuretics, aldosterone antagonists, vasodilators, ionotrophic agents, statins or combinations thereof.

Still further, the invention relates to a method for the prevention or treatment of a cardiac disorder comprising administering to a subject in need thereof a therapeutically effective amount of at least one isolated nucleic acid molecule as described herein.

Further, the present invention shall be described in more detail by the following Figures and Examples.

FIGURE LEGENDS

FIG. 1. MicroRNAs miR-212 and miR-132 are induced during hypertrophic conditions and promote cardiomyocyte hypertrophy.

(a) Overexpression of miRNA precursors from a library identified miRNAs enhancing cardiomyocyte growth and brain natriuretic peptide (BNP) secretion. The miRNA family miR-212/132 is highlighted by gray circles.

(b, c) Effects of miR-212 and miR-132 precursors and inhibitors (anti) on cardiomyocyte cell size as compared to the effects of scrambled (Scr) controls. (n=5-13).

Representative images used for quantification of cardiomyocyte cell size are shown in c.

(d) Effects of various pro-hypertrophic stimuli on miR-212 and miR-132 expression in neonatal cardiomyocytes. (n=6-10).

(e) miR-212 and miR-132 expression levels during pressure-induced left ventricular hypertrophy 3 and 21 days after transaortic constriction (TAC) surgery of mice. (n=4).

(f) Cardiomyocyte diameters after Sham operation or 3, 14 and 35 days after transaortic constriction (TAC) (n=4 per group).

(g,h) miR-212 and miR-132 expression (normalized to sno-202 levels) in fractionated cardiomyocytes and cardiac fibroblasts derived from adult mice after 3 and 35 days of transaortic constriction (TAC).

All values represent mean±SEM.

*p<0.05; p<0.01; *p<0.005 FC: fold change, ACTN2: alpha cardiac actinin, n.s: no significant difference, a.u: arbitrary unit. Scale bar in c represents 50 µm.

Figure 2:
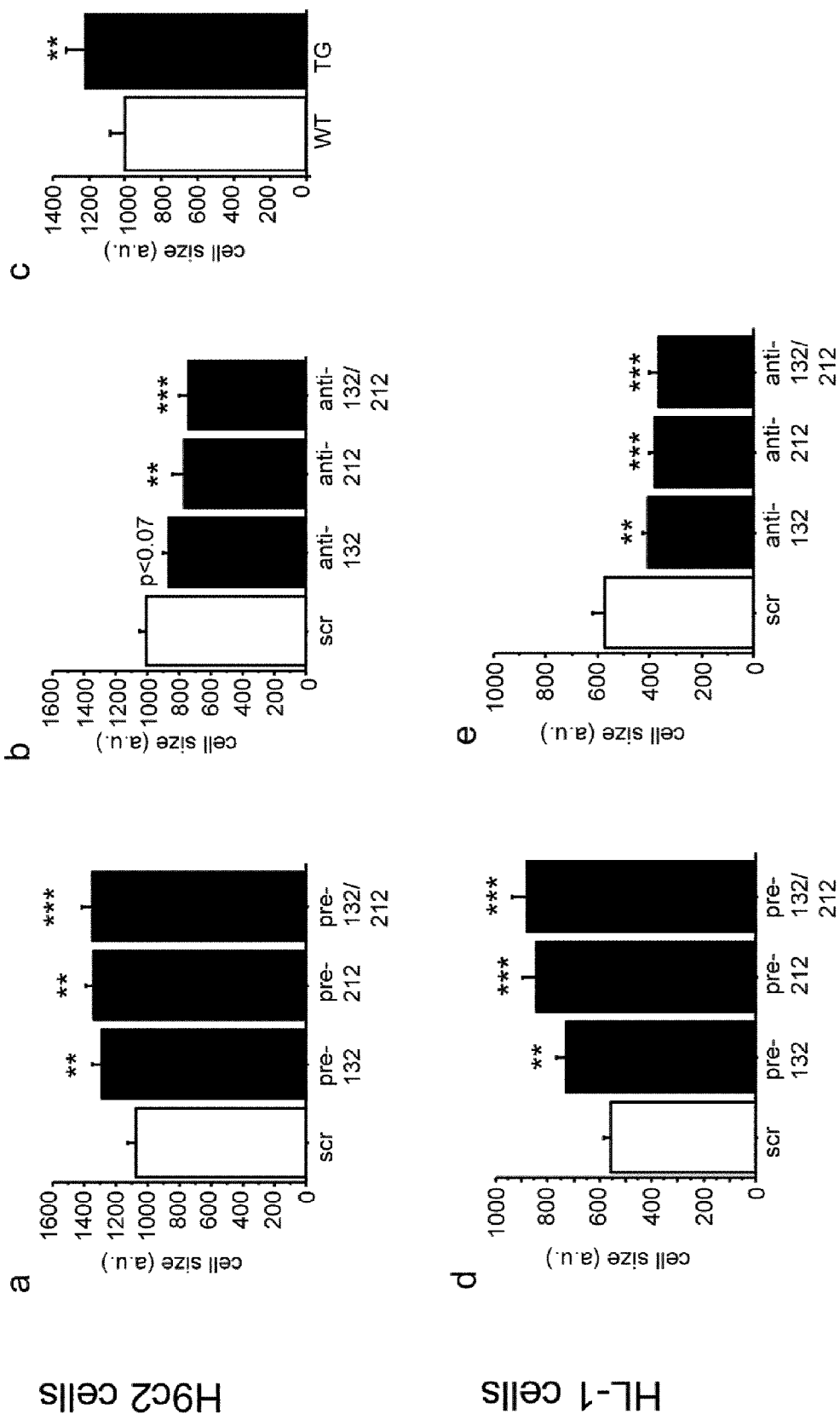

FIG. 2. MicroRNAs miR-212 and miR-132 induce hypertrophy in cardiomyocyte cell lines.

Effects of overexpression of miR-212 and/or miR-132 precursors (pre-) (a, d) and silencing by inhibitors (anti-) (b, e) on size of H9c2 (a, b) and HL-1 (d, e) cells as compared to the effects of scrambled (scr) controls. (c) Cell size of wild-type (WT) and miR-212/132-overexpressing transgenic (TG) H9c2 cells. Values represent mean±SEM. (n=5-14) p<0.01, *p<0.005; a.u.=arbitrary unit.

Figure 3:
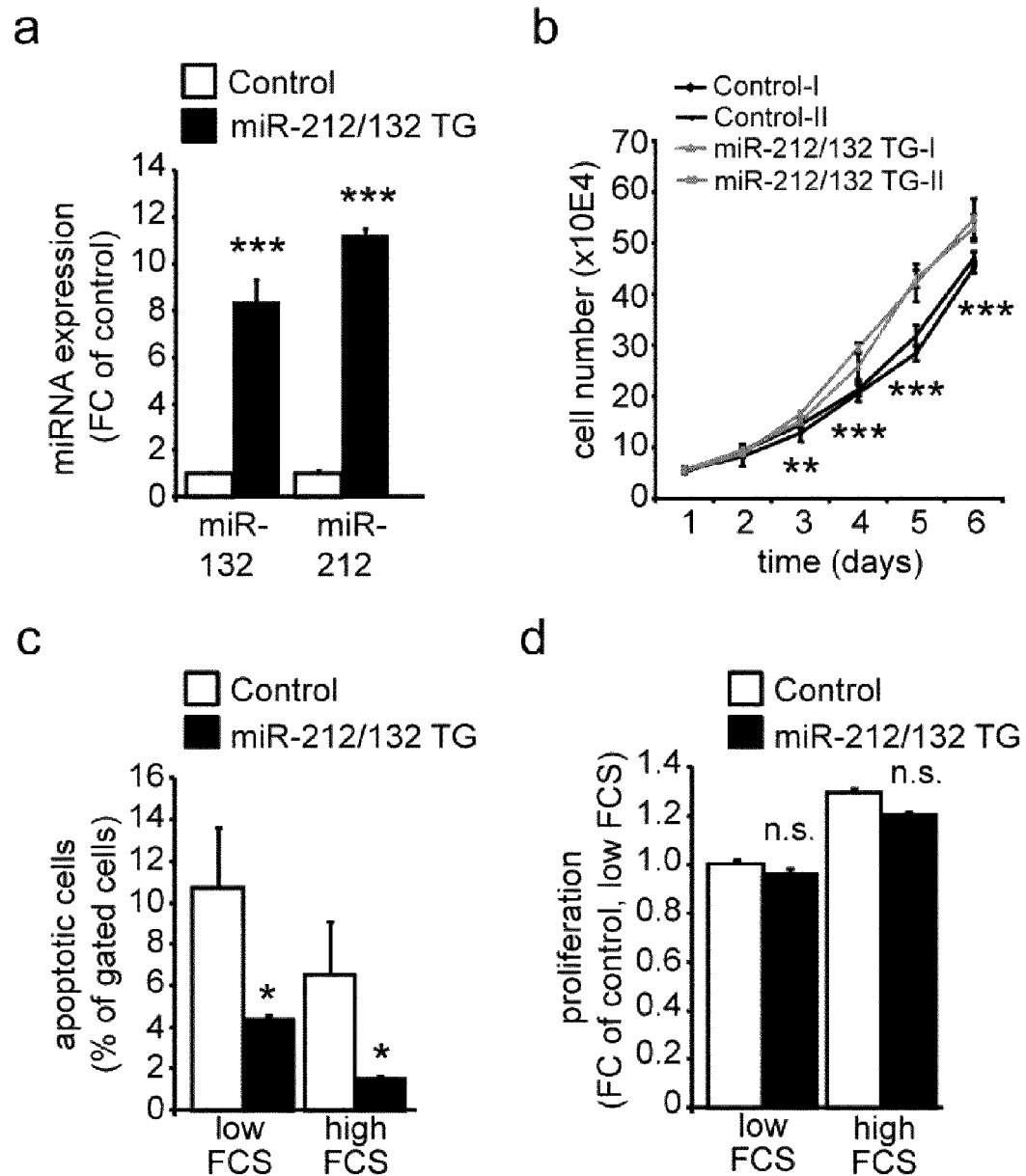

FIG. 3. MiRNA family miR-212/132 reduces apoptosis in H9c2 cells.

(a) Expression levels of miR-132 and miR-212 in miR-212/132 overexpressing (miR-212/132 TG) and control H9c2 cell lines. (n=3).

(b) Time-dependent increase of cell number in miR-212/132 overexpressing (TG-I, TG-II) and control (I, II) H9c2 cell lines. (n=6).

(c, d) Number of apoptotic cells assessed by Annexin-V FACS analysis (c) and proliferation rate measured by WST assay (d) in the presence of high (10%) and low (1%) FCS in miR-212/132 overexpressing and control H9c2 cell lines. (n=6). All values represent mean±SEM in a, c and d; and mean±SD in b. *p<0.05; p<0.01; *p<0.005; n.s., no significant difference.

Figure 4:
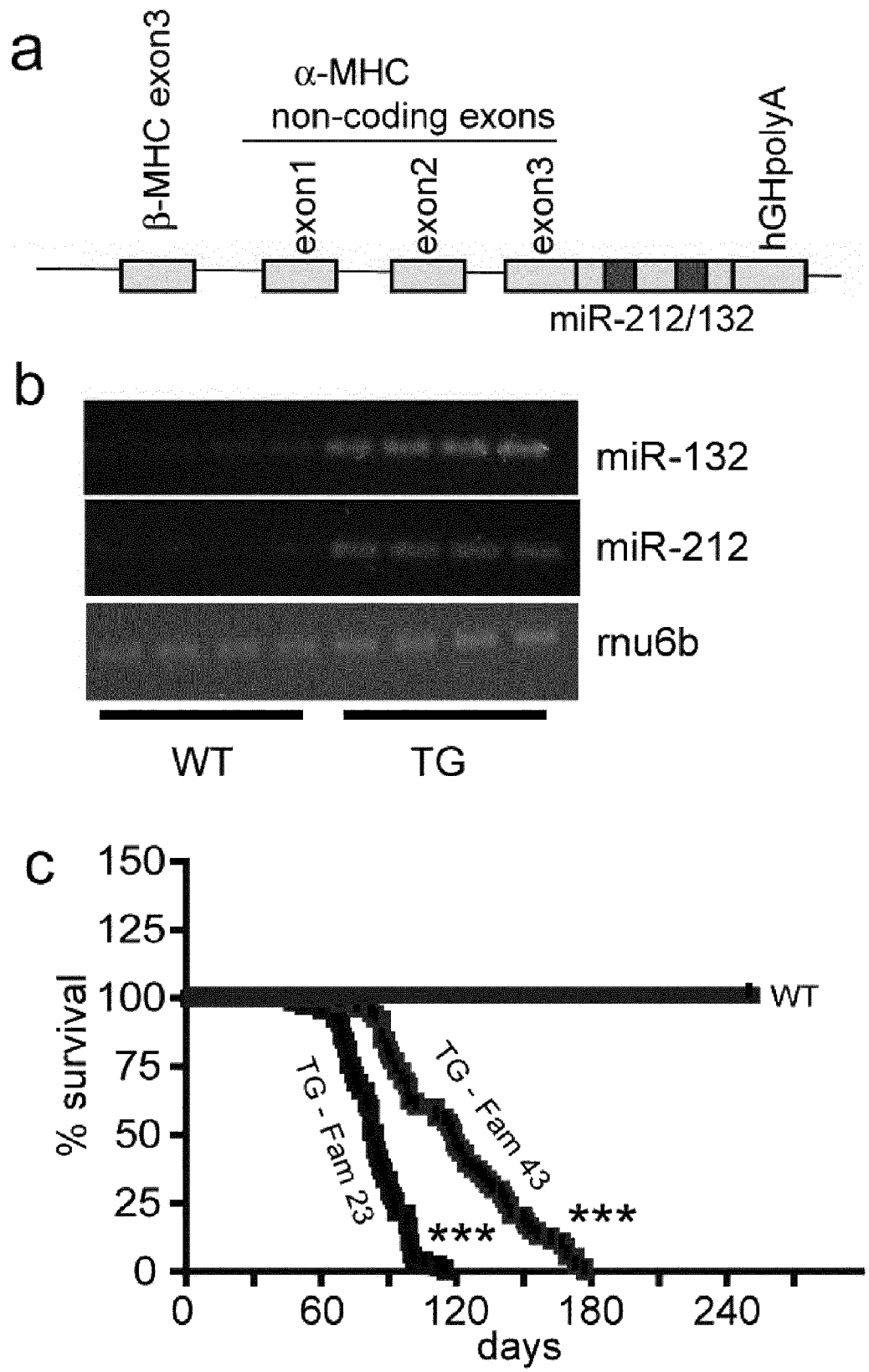
Figure 4:
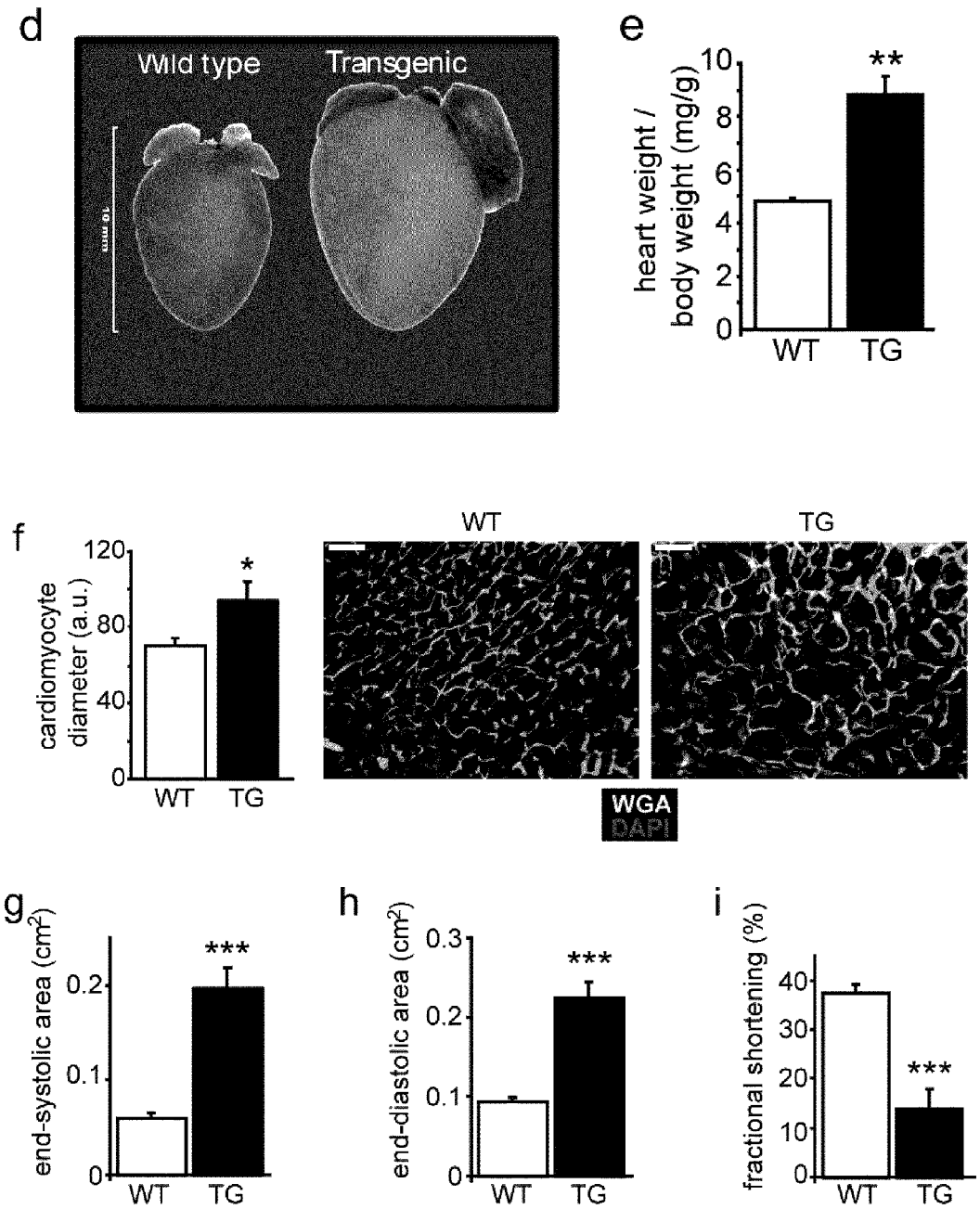

FIG. 4. Cardiomyocyte-specific overexpression of the miR-212/132 family leads to pathological cardiac hypertrophy and heart failure in mice.

(a) Overexpression construct of miR-212/132 under the control of the alpha-MHC promoter.

(b) Expression levels of miR-212 and miR-132 in heart samples of individual wild-type (WT) and miR-212/132 transgenic (TG) mice as assayed by standard RT-PCR analysis.

Rnu6b was used as housekeeping control.

(c) Survival rate of two different miR-212/132 transgenic mouse families (TG-Fam23, TG-Fam43) versus wild-type controls was analyzed by Kaplan-Meier survival assay. (n=87, 65, and 53 for WT, TG-Fam23, and TG-Fam43, respectively).

(d) Morphology of explanted hearts from TG and WT mice at 10 weeks after birth.

(e-f) Heart to body weight ratios (e) and cardiomyocyte diameter (f) in 8-weeks-old alpha-MHC-miR-212/132 transgenic mice compared to their wild-type littermates. (n=5-7).

Scale bar represents 50 µm.

(g-i) Echocardiographic analysis of cardiac dimensions and function for alpha-MHC-miR-212/132 transgenic mice and wild-type controls (n-16-18). (g) end-systolic area, (h) end-diastolic area, (i) fractional shorting). All values in e-i represent mean±SEM. *p<0.05; p<0.01; *p<0.005; WGA: wheat germ agglutinin (membrane stain).

Figure 5:
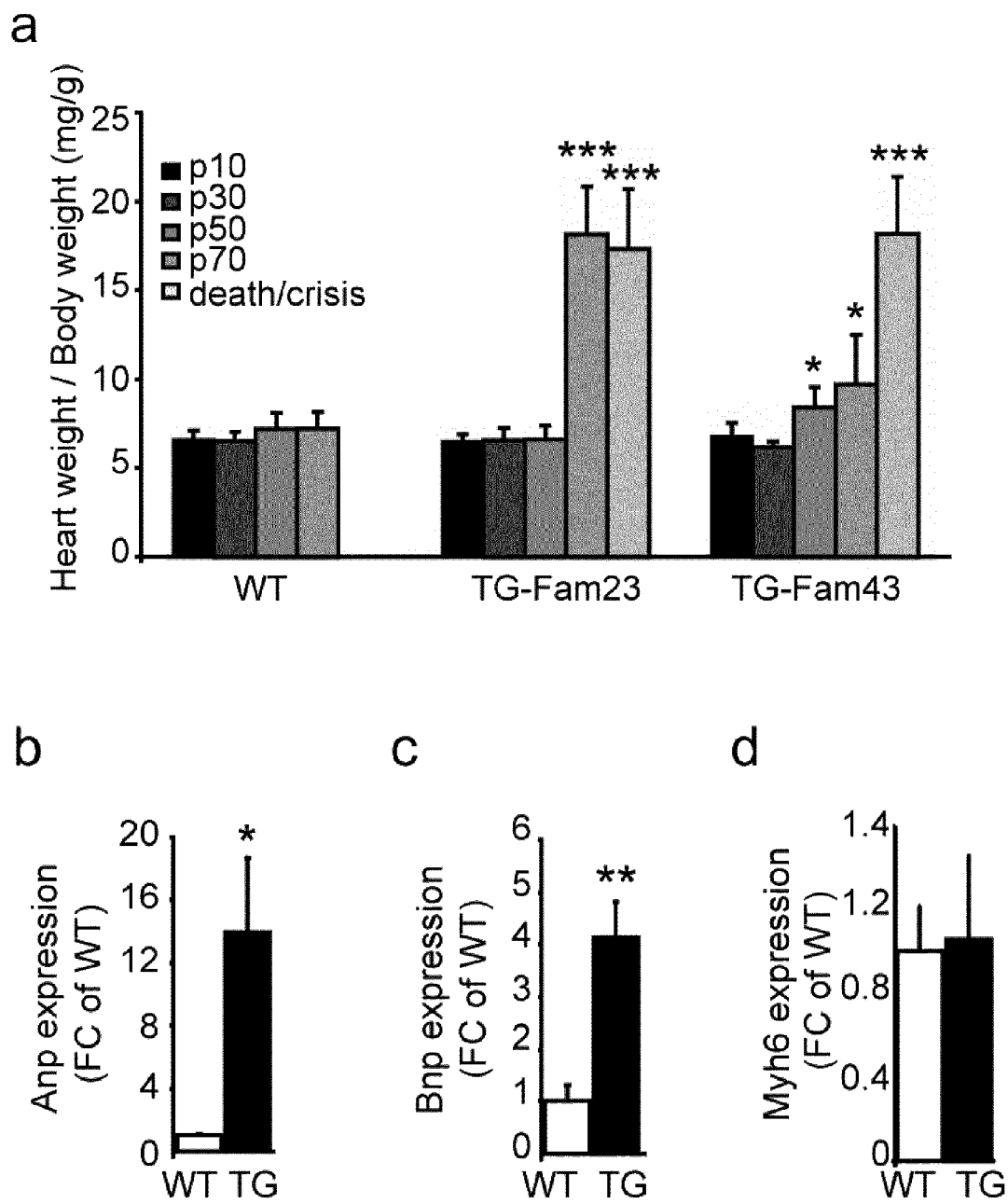
Figure 5:
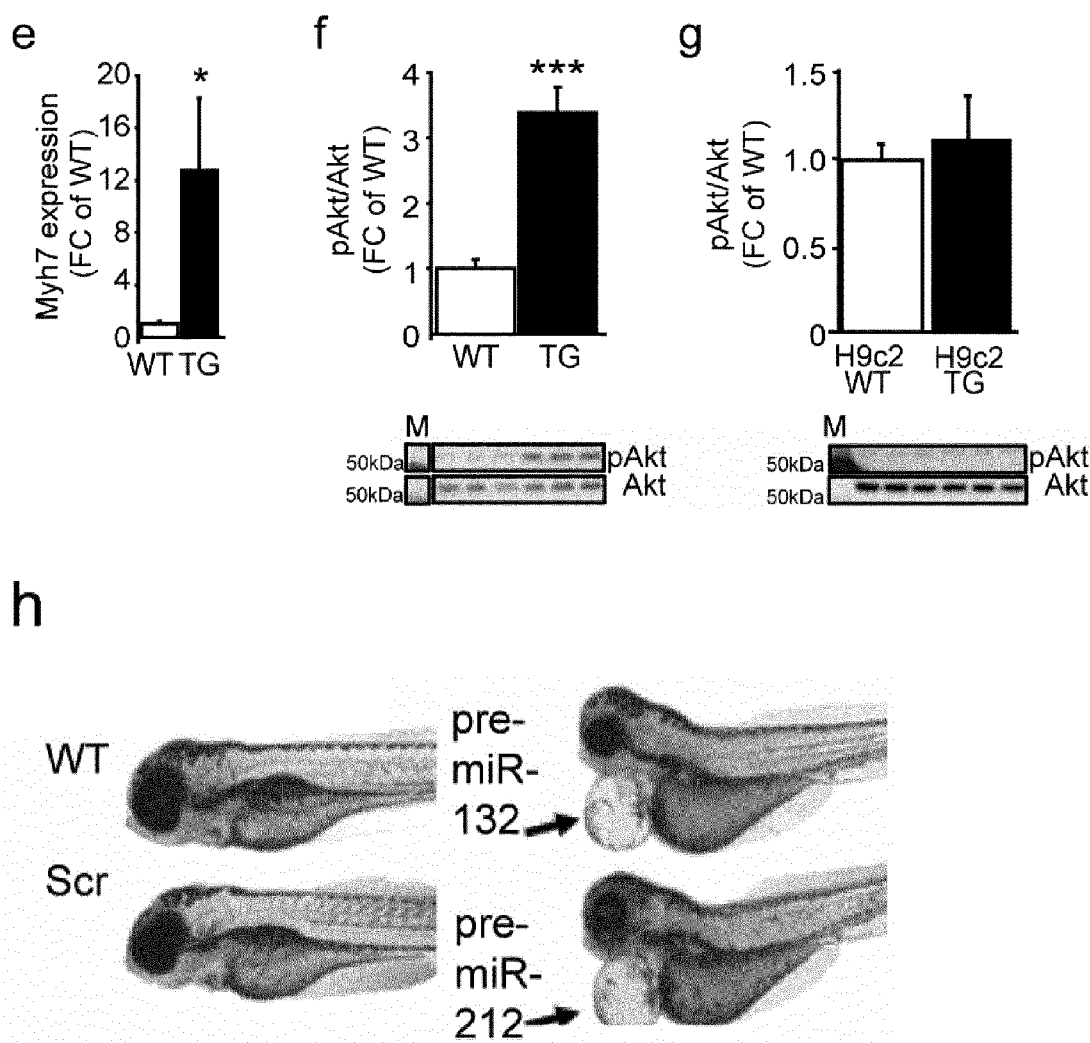

FIG. 5. Overexpression of miR-212/132 family in the heart leads to cardiac hypertrophy.

(a) Heart-to-body weight ratios in wild-type (WT) and two independent cardiomyocyte-specific miR-212/132-overexpressing transgenic mouse lines (TG-Fam23 and TG-Fam43)

between postnatal (p) day 10 and 70 as well as during death/crisis. Values represent mean±SEM. *:p<0.05 versus p30 levels; ***:p<0.005 versus p30 levels; (n=3-13).

(b-f) Cardiac mRNA expression levels of Anp (b), Bnp (c), alpha-myosin heavy chain (Myh6; d), beta-myosin heavy chain (Myh7; e) and cardiac protein expression levels of p-Akt (relative to Akt; f) in cardiomyocyte-specific miR-212/132-overexpressing transgenic (TG) mice and their wild-type (WT) littermates. Values represent mean±SEM. *p<0.05, p<0.01, *p<0.005; (n=5-10).

(g) pAkt/Akt ratios in wild-type (WT) and miR-212/132-overexpressing (TG) H9c2 cell lines (n=9).

(h) Phenotype of wild type non-injected (WT), and scrambled miR (scr), pre-miR-132 or pre-miR-212 injected zebrafish embryos 48 hrs post fertilization. The pre-miR-132 and pre-miR-212 injected embryos display a severe pericardial effusion, compared to scrambled injected or wild type control embryos (black arrows). M: Western blot marker; FC: Fold change.

Figure 6:
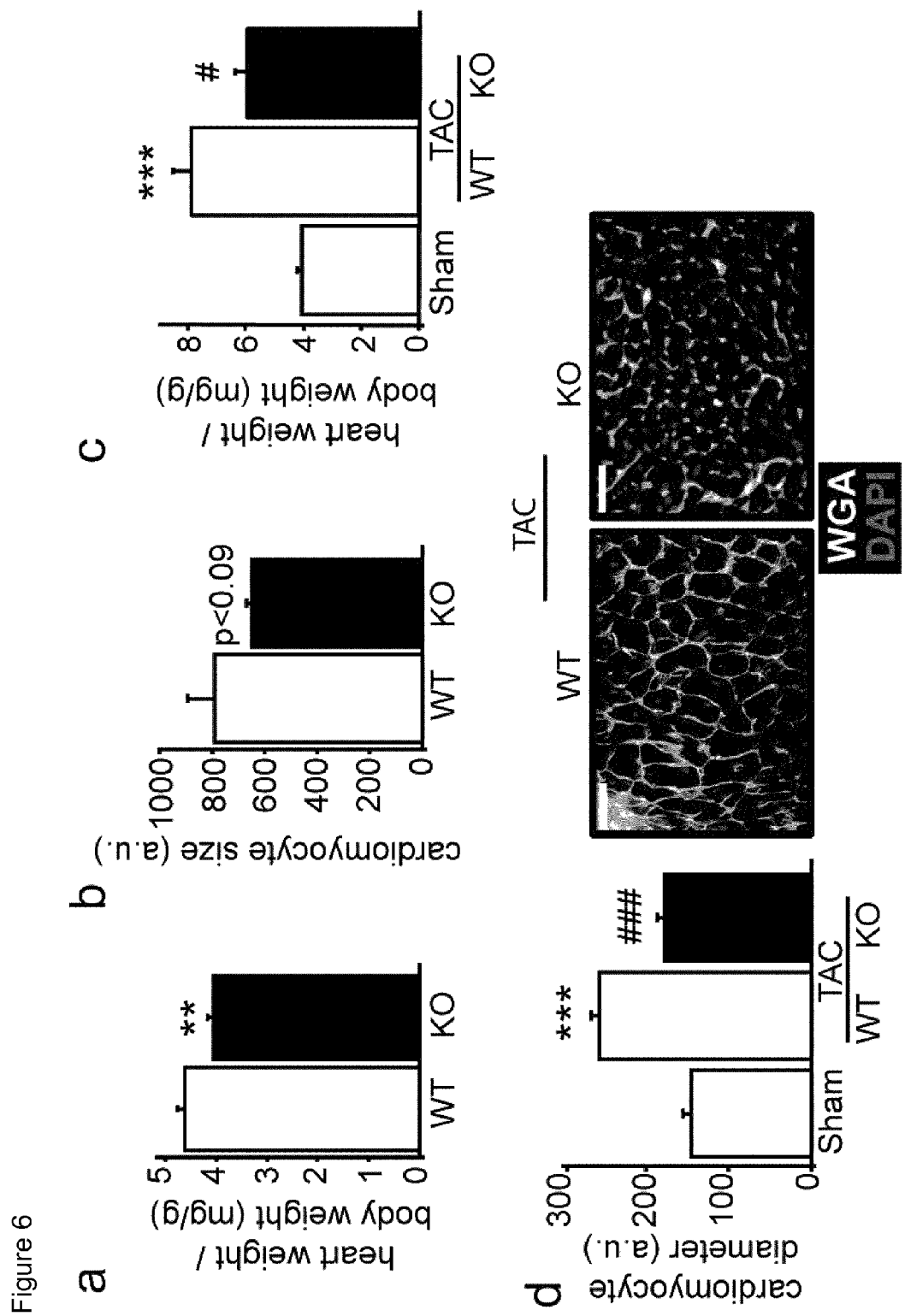
Figure 6:
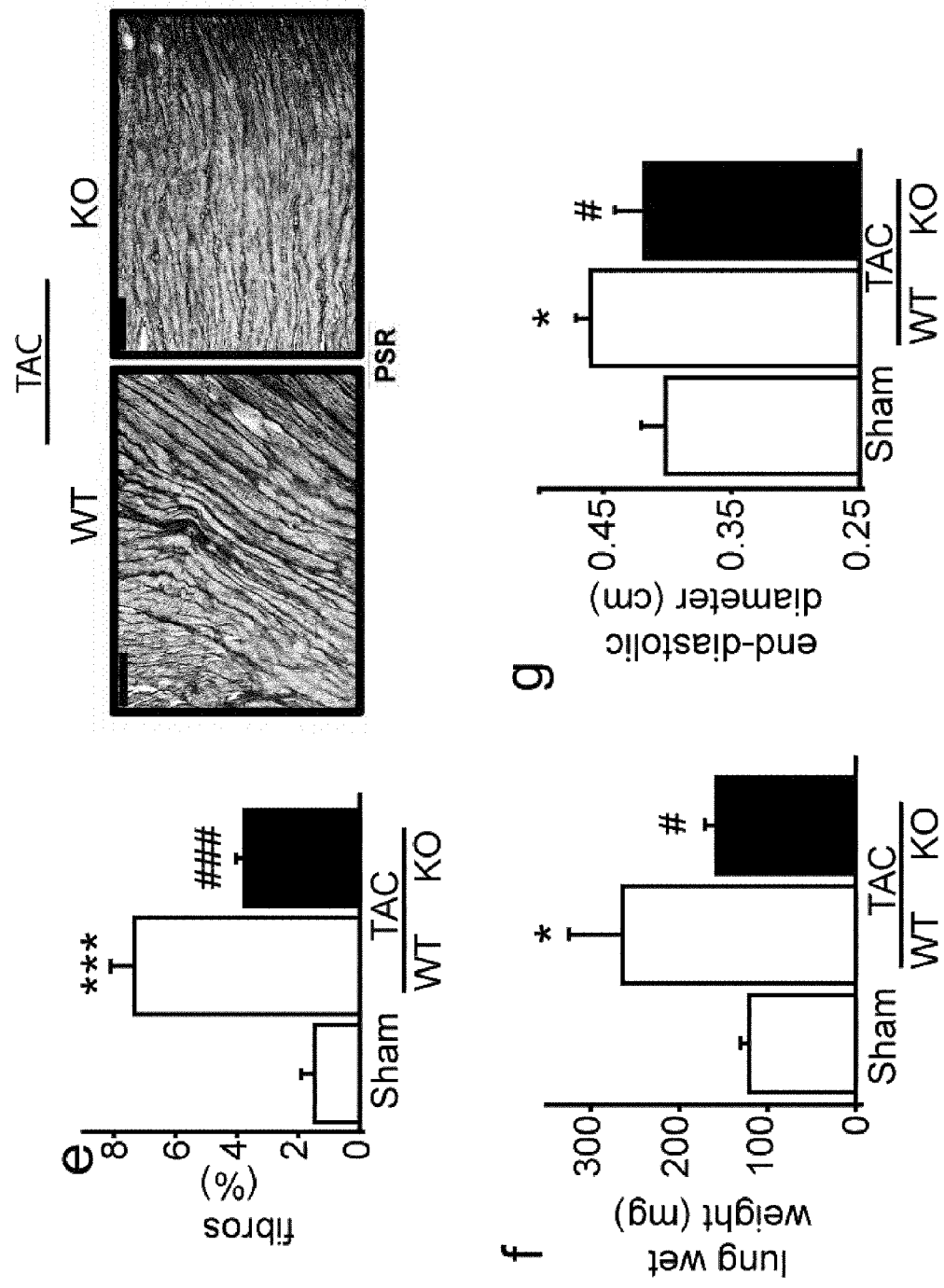
Figure 6:
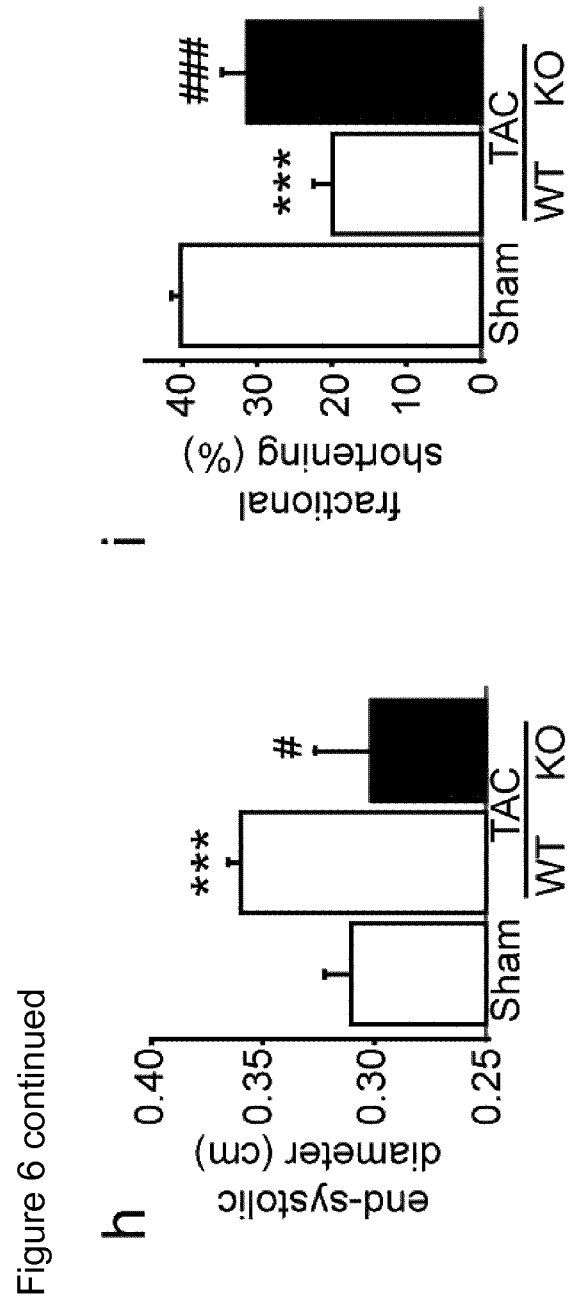

FIG. 6. MiR-212/132-null mice are protected from cardiac pressure-overload-mediated hypertrophy, fibrosis and heart failure.

(a) Heart to body weight ratios for 12-weeks-old miR-212/132-null (KO) and wild-type (WT) mice. (n=5-6).

(b) Cardiomyocyte cell size of neonatal miR-212/132-null and wild-type mice. (n=5-6 isolations).

(c-f) Heart to body weight ratios (c), cardiomyocyte diameter (d), cardiac fibrosis (e), and lung wet weight (f) in Sham-operated wild-type mice and miR-212/132-null and wild-type mice 3 weeks after transaortic constriction (TAC) surgery. (n=4-7).

Scale bar represents 50 μm.

(g-i) Echocardiographic analysis of cardiac dimensions and function in Sham-operated wild-type mice and miR-212/-132-null and wild-type mice 3 weeks after TAC. (n=4-11). (g) end-diastolic area, (h) end-systolic area, (i) fractional shorting). All values represent mean±SEM. *p<0.05; p<0.01; *p<0.005; #p<0.05 compared to WT TAC; ###p<0.005 compared to WT TAC; PSR: picrosirius red (collagen stain).

Figure 7:
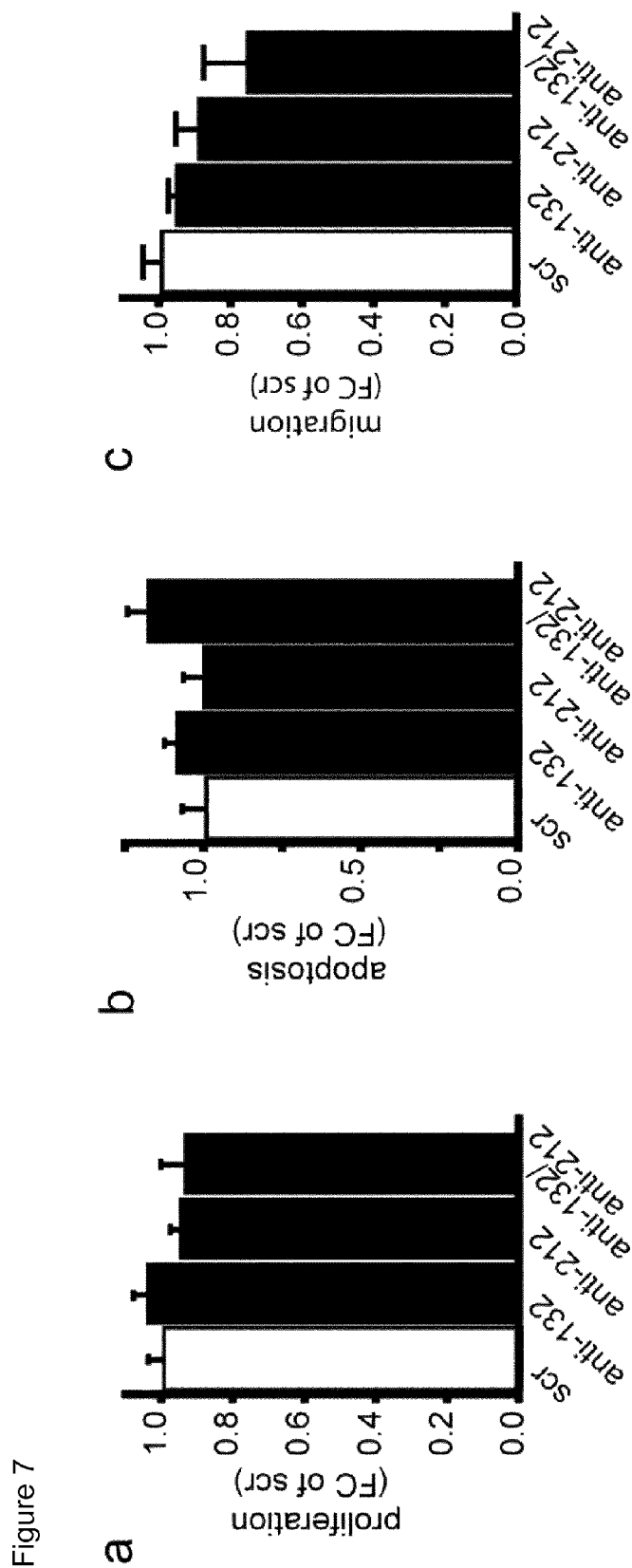

FIG. 7. miR-212 and miR-132 repression does not effect proliferation, apoptosis or migratory behaviors of human cardiac fibroblasts.

Proliferation (a), apoptosis (b) and migration (c) of human cardiac fibroblasts 72 h post-transfection with scrambled control (Scr) and anti-miR-212 and anti-miR-132. (n=6). All values represent mean±SEM.

Figure 8:
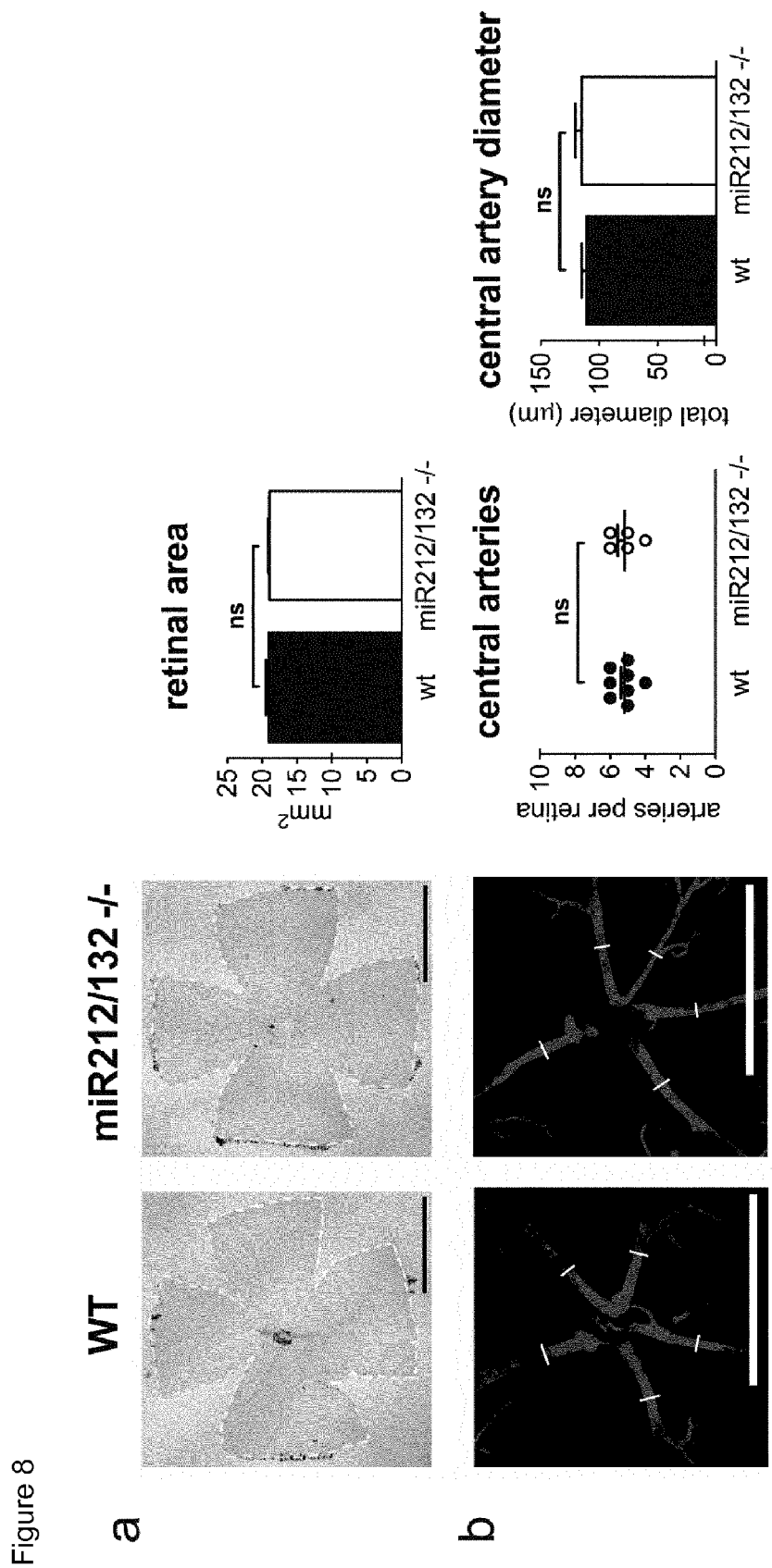
Figure 8:
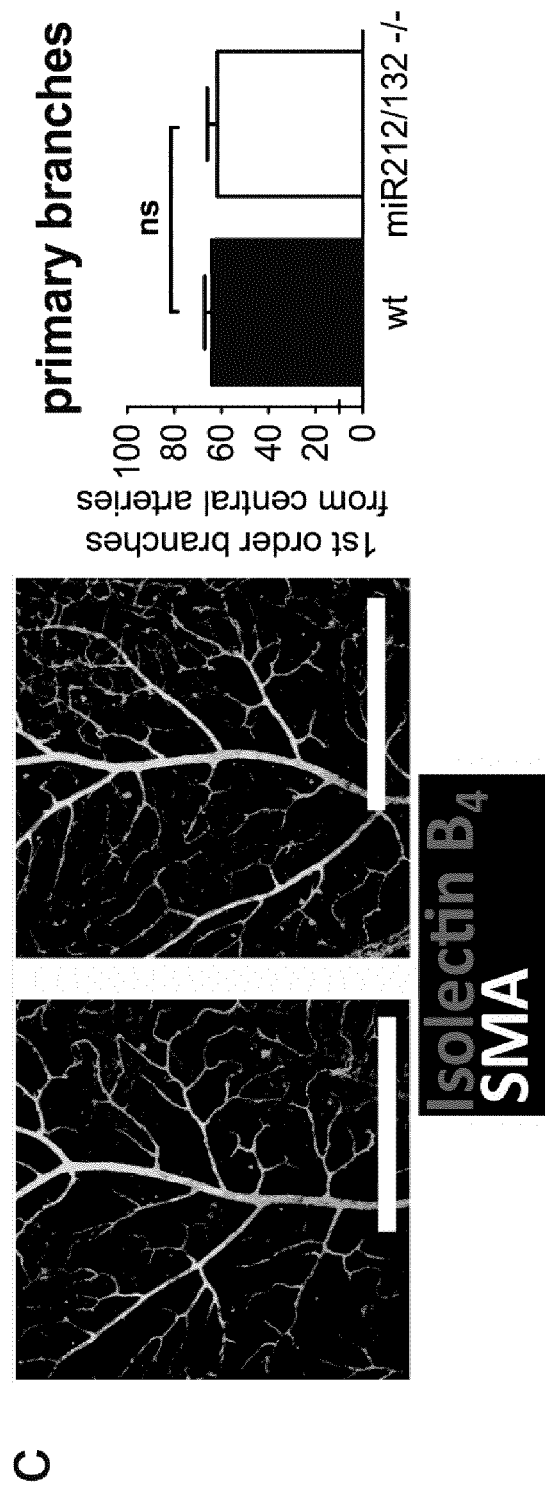
Figure 8:
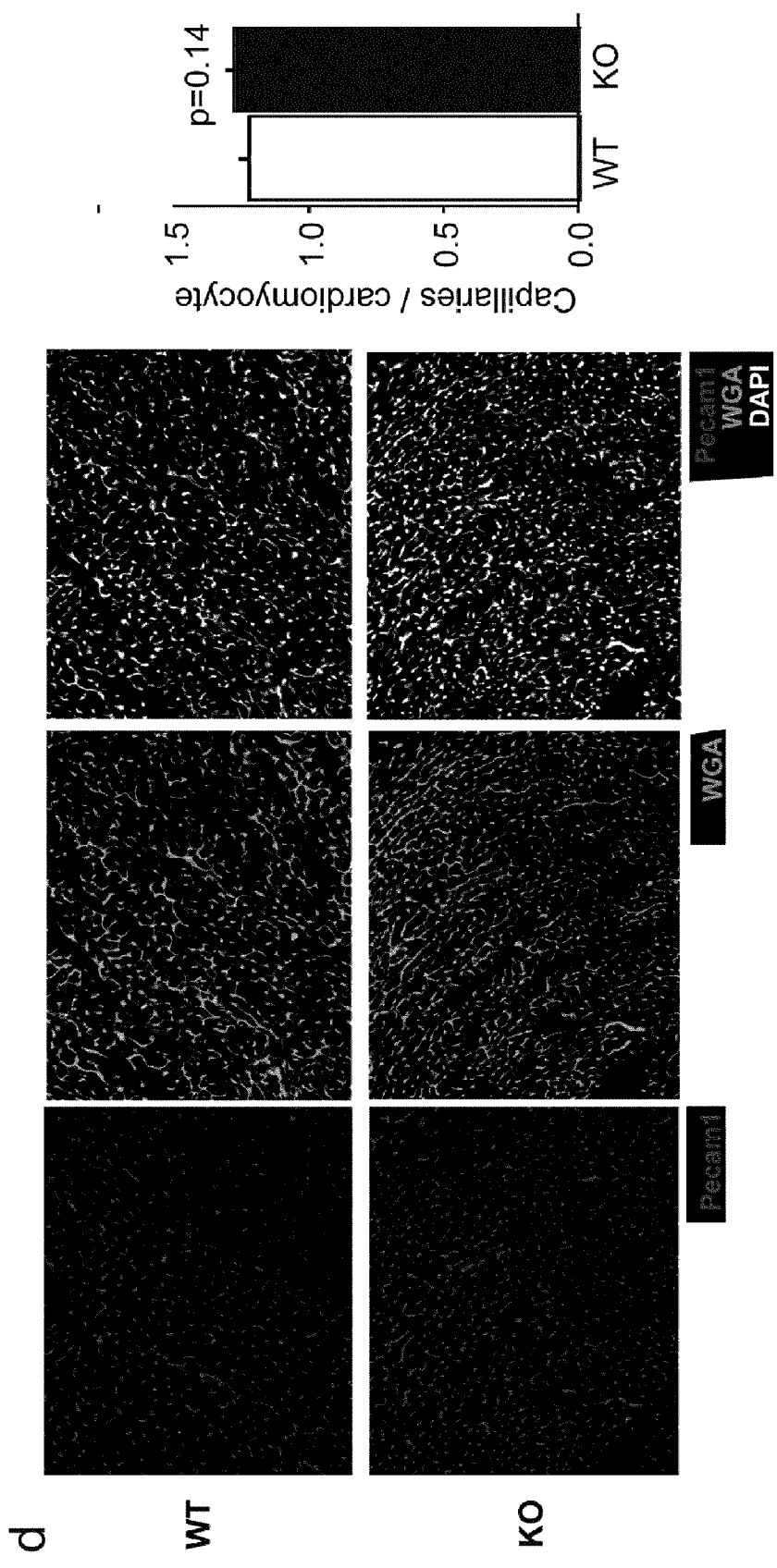

FIG. 8. Absence of an overt vascular phenotype in miR-212/132 null mice.

The vascular system was studied in retinas of adult miR-212/132$^{-/-}$ mice compared to wild-type (WT) littermates.

Retinal area (a), number and total diameter of central retinal arteries originating from the optic nerve (b, measured at 200 μm distance from the optic nerve), and number of 1$^{st}$ order branches originating from central arteries (c, number per retina) were similar in miR-212/132$^{-/-}$ mice and wild-type littermates. (n=5-8 retinas from at least 3 mice).

(d) Staining of cardiac sections of wild-type (WT) and miR-212/132$^{-/-}$ (KO) mice for Pecam1, wheat germ agglutinin and DAPI. Graph represents the number of capillaries per cardiomyocytes. (n=5). All values represent mean±SEM. Scale bars represent 2 mm in a, 500 μm in b and c. ns: not significant.

Figure 9:
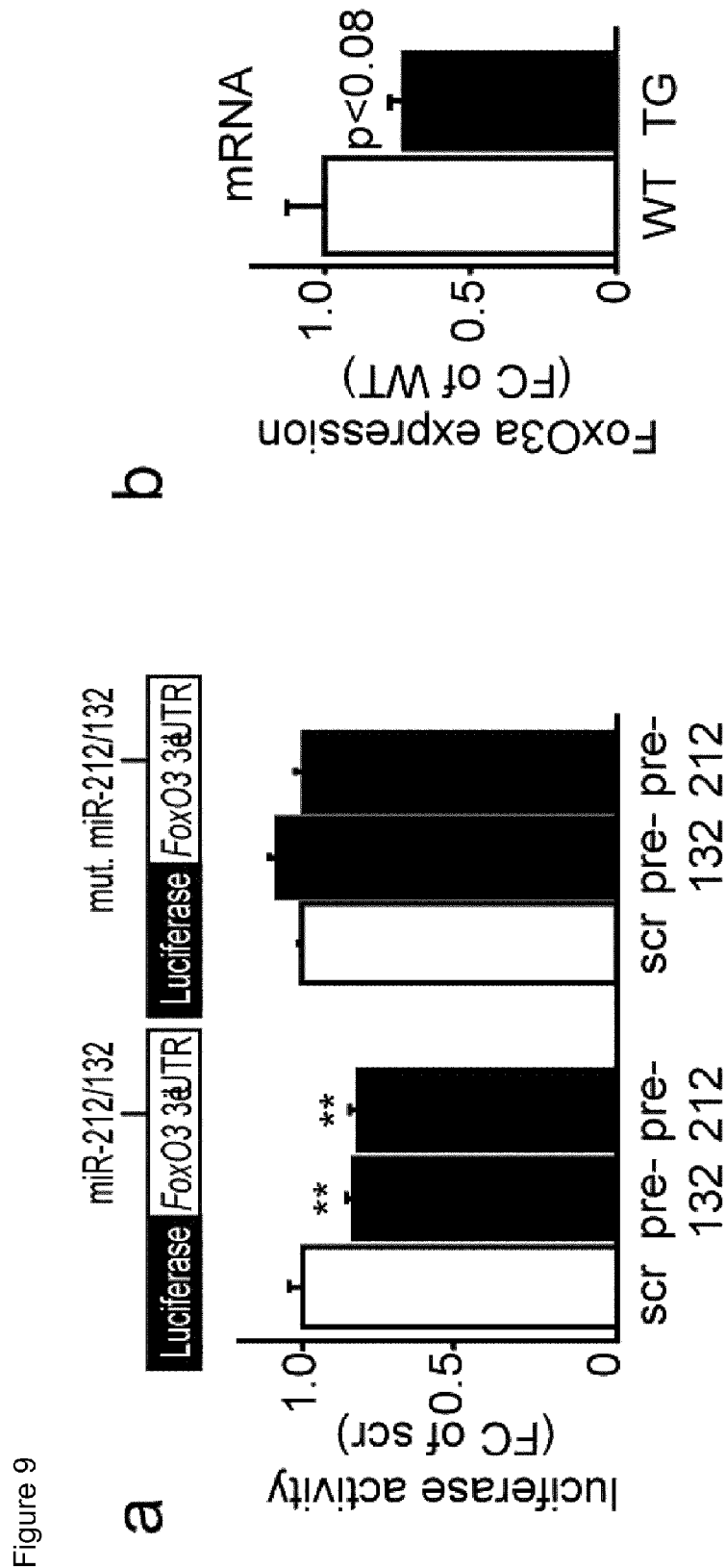
Figure 9:
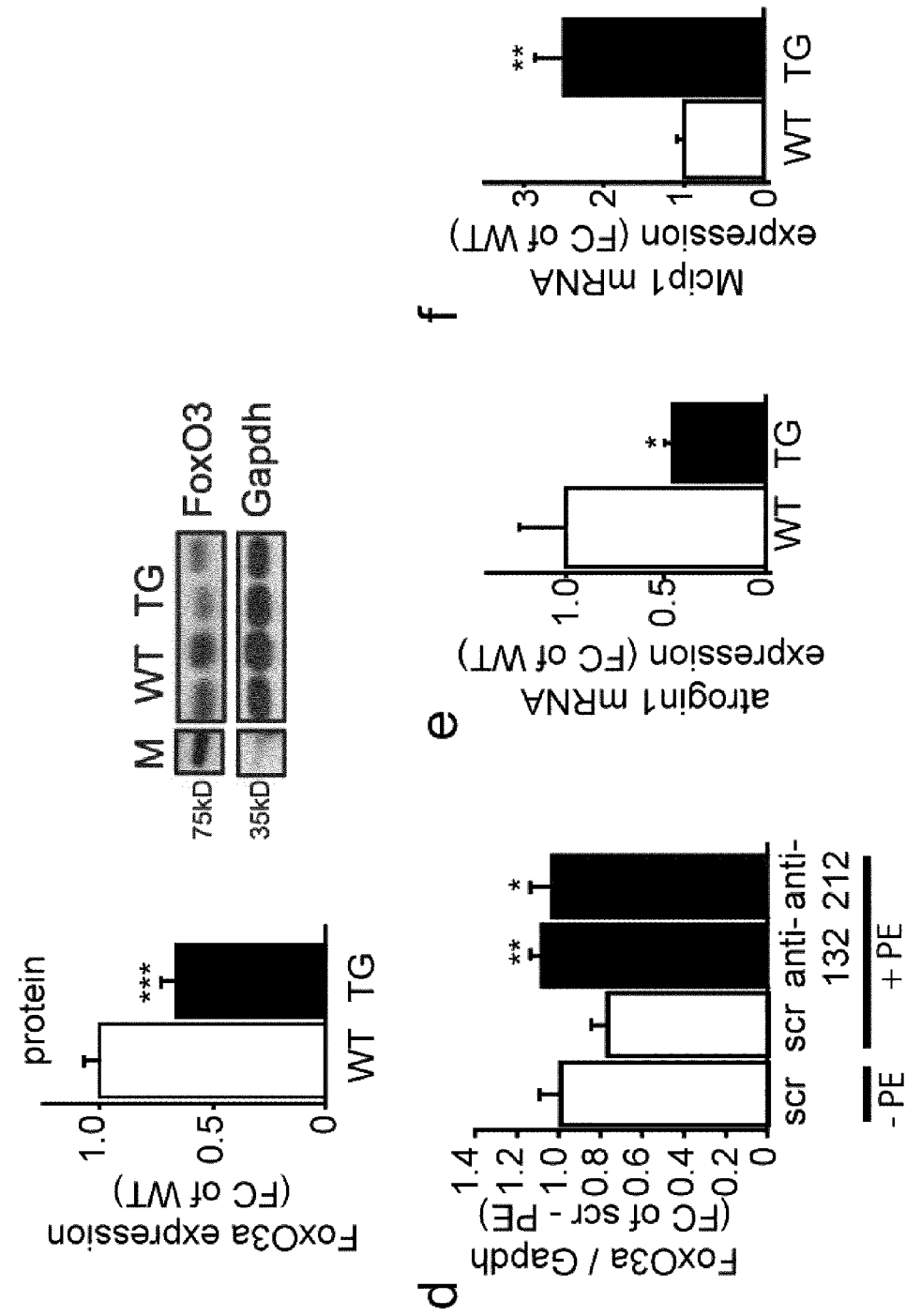
Figure 9:
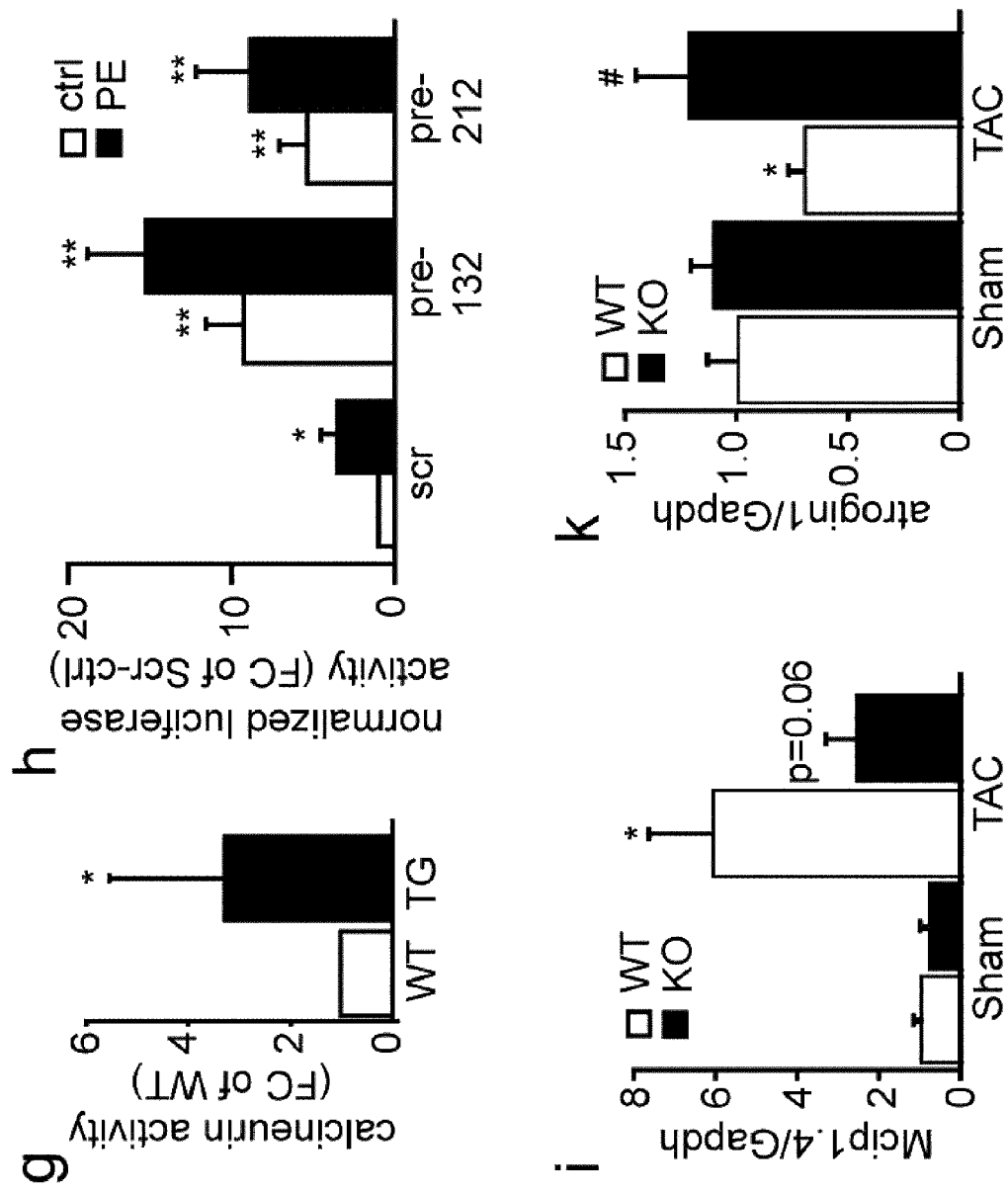

FIG. 9. MiR-212/132 family directly regulates expression of FoxO3 and consequently activates pro-hypertrophic calcineurin/NFAT signalling.

(a) Luciferase activity levels upon cotransfection of a luciferase construct containing wild-type or mutated 3'UTR of FoxO3 with either scrambled control (scr), pre-miR-132, or pre-miR-212. (n=9).

(b, c) Expression levels of FoxO3 on mRNA (b) and protein levels (c) in hearts of wild-type (WT) and alpha-MHC-miR-212/-132 transgenic (TG) mice. (n=9-13).

(d) FoxO3 mRNA levels in neonatal rat cardiomyocytes transfected with scrambled control (scr), anti-miR-212 and anti-miR-132 after phenylephrine (PE, 10 μM) treatment (n=6-9; p-values against scr+PE).

(e-g) Expression levels of atrogin-1 (e) and Mcip1.4 (f) and calcineurin phosphatase activity levels (g) in hearts of wild-type and alpha-MHC-miR-212/132 transgenic mice. (n=5-9).

(h) Luciferase activity levels showing the NFAT transcriptional activity in cardiomyocytes transfected with either scrambled control (scr), pre-miR-132, or pre-miR-212. (n=5).

(i,k) Mcip1.4 (i) and atrogin-1 (k) mRNA levels in wild-type (WT) and miR-212/132 null (KO) mice 3 weeks after transaortic constriction (TAC) or Sham operation (n=5-7 per group).

All values represent mean±SEM. *p<0.05; p<0.01; *p<0.005. #p<0.05 compared to WT TAC.

Figure 10:
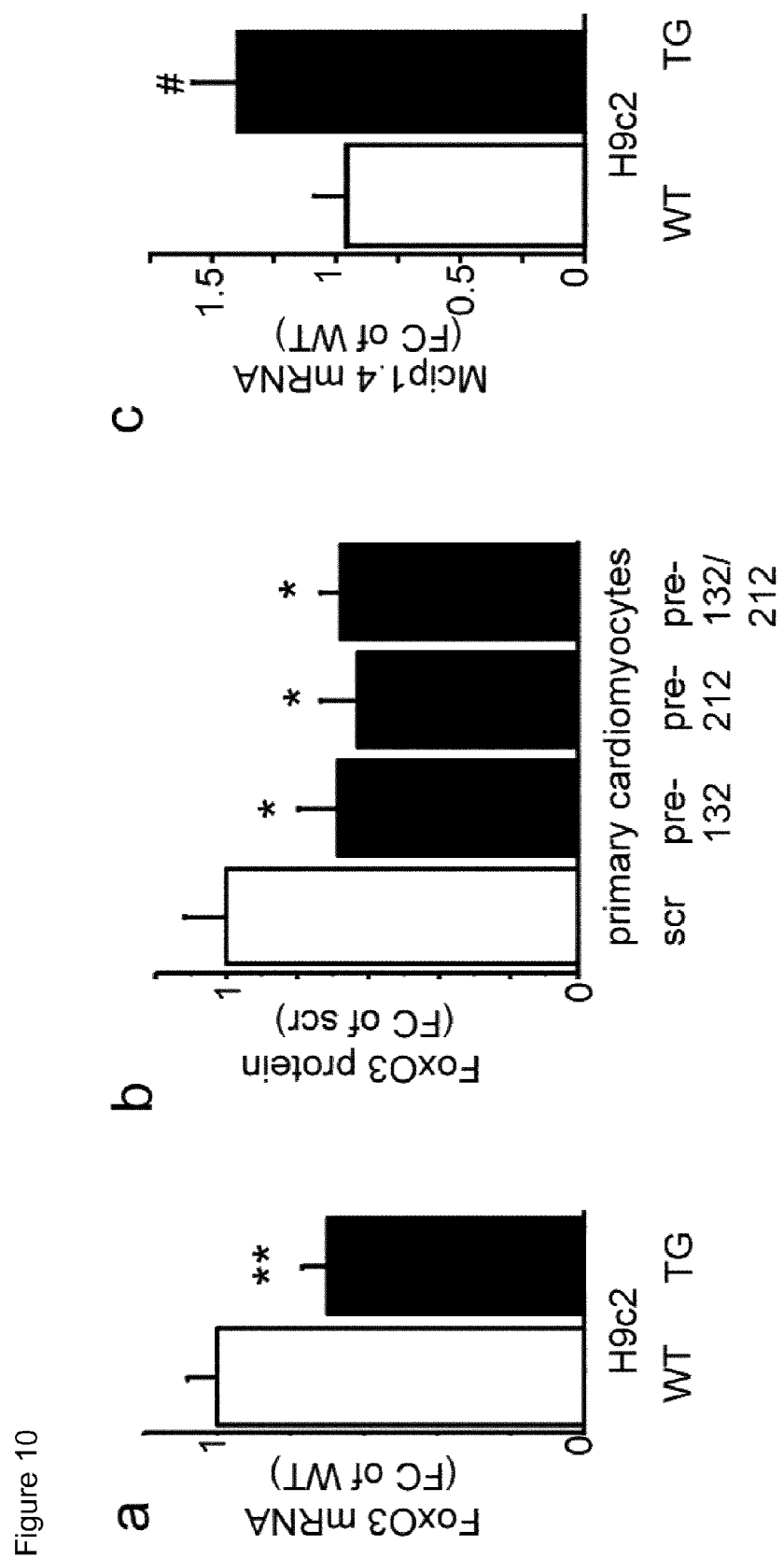

FIG. 10. MiR-212/132 overexpression leads to FoxO3 downregulation and Mcip1.4 upregulation in cardiomyocytes.

(a) Expression of FoxO3 mRNA in wild-type (WT) and miR-212/132-overexpressing transgenic (TG) H9c2 cells.

(b) FoxO3 protein levels in neonatal cardiomyocytes three days after transfection with scrambled controls (scr), miR-132, miR-212 or miR-132 and miR-212 precursor molecules.

(c) Mcip1.4 mRNA levels in wild-type (WT) and miR-212/132-overexpressing transgenic (TG) H9c2 cells.

FC: fold change. Values represent mean±SEM. *p<0.05; **p<0.01; #p=0.052 (n=4-7).

Figure 11:
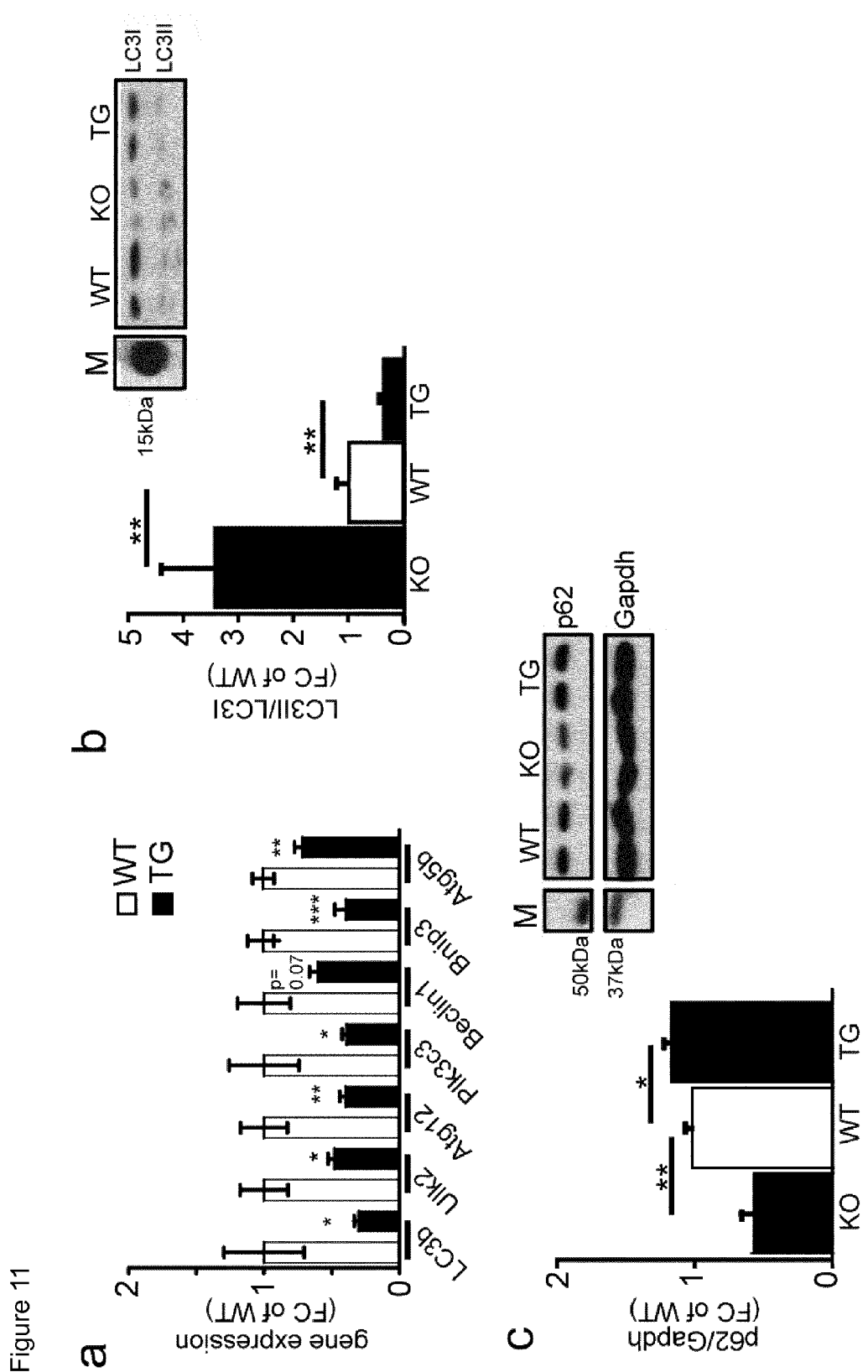
Figure 11:
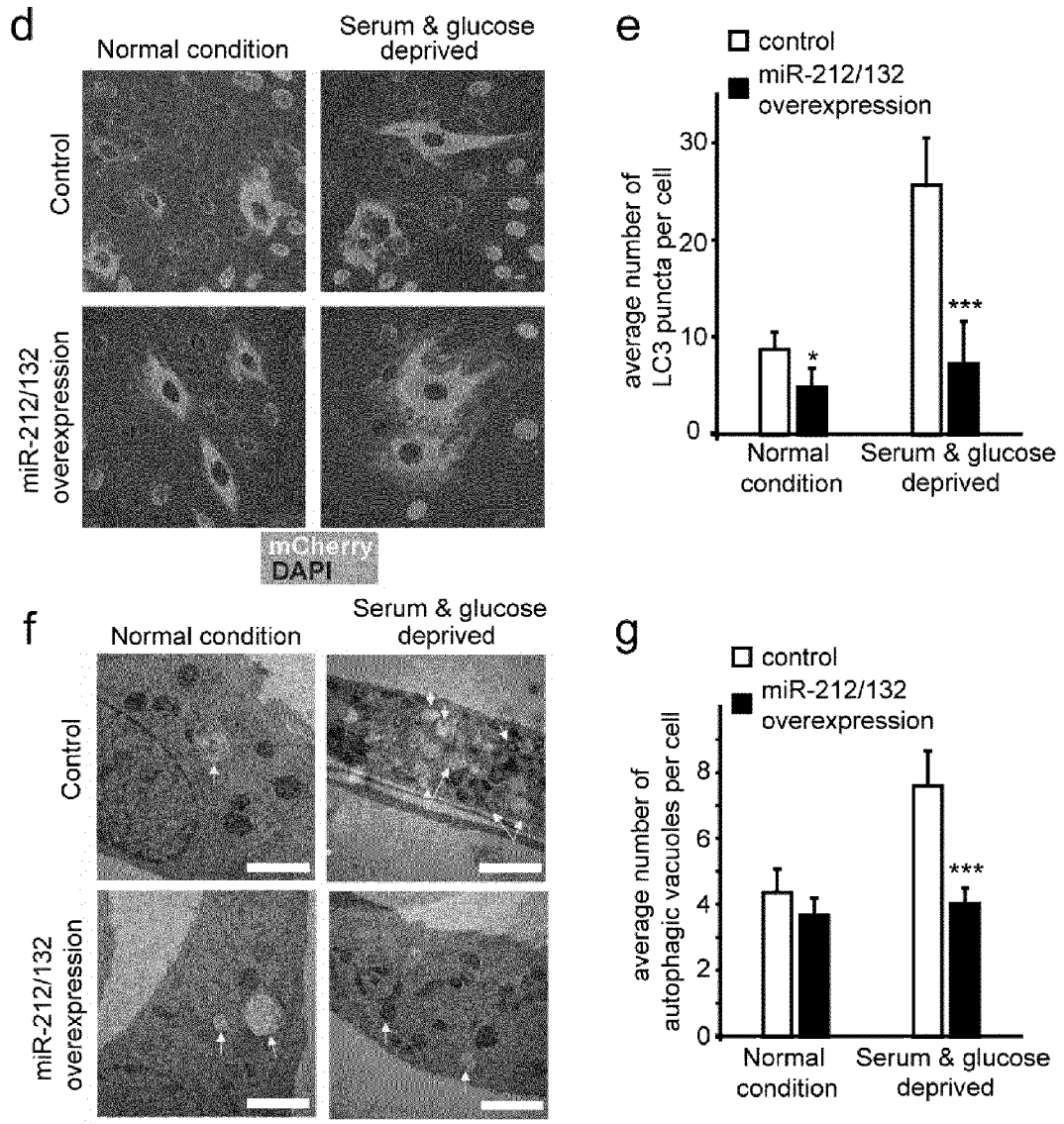
Figure 11:
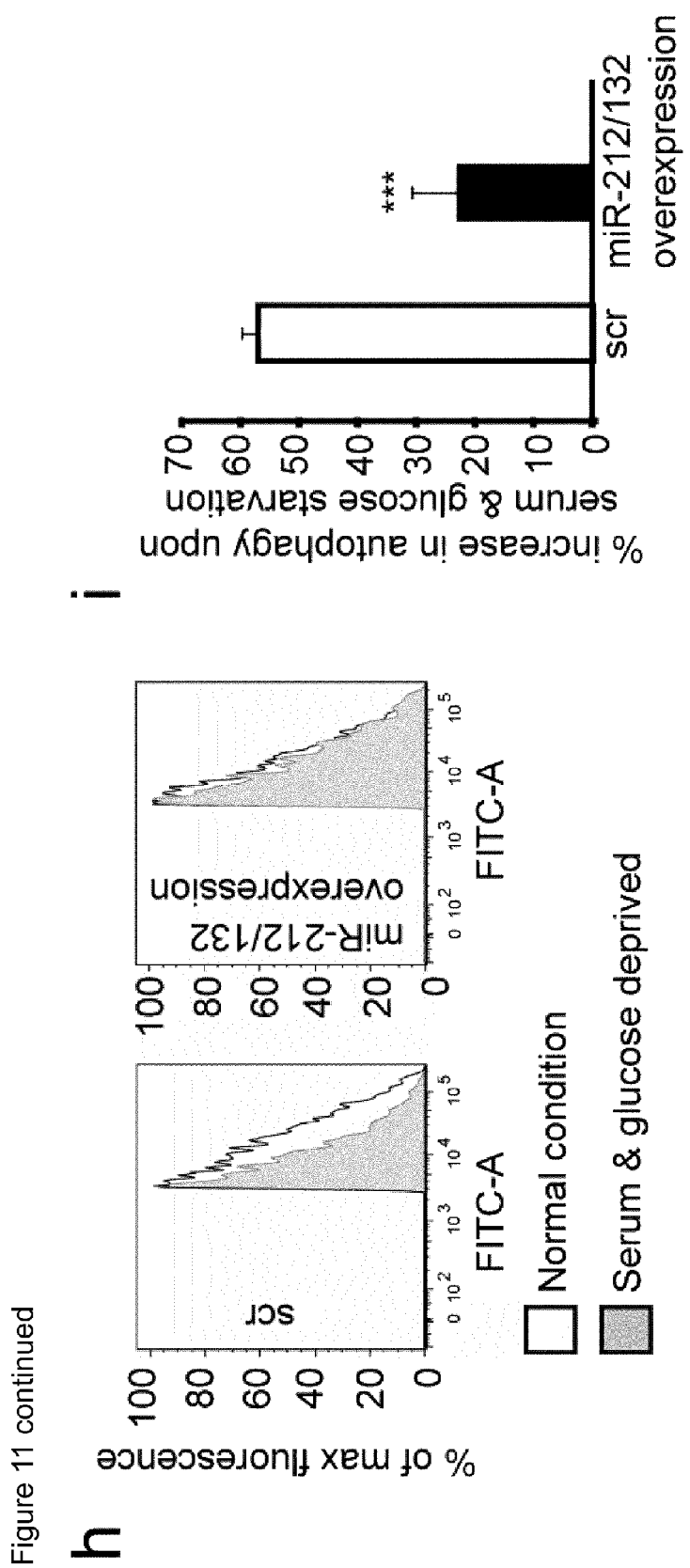

FIG. 11. MiR-212/132 is an anti-autophagic factor in cardiomyocytes.

(a) mRNA expression levels of autophagic marker genes in hearts of wild-type (WT) and alpha-MHC-miR-212/-132 transgenic mice (TG). (n=9-10).

(b, c) Ratio of LC3II to LC3I (b) and p62 protein levels (c) in wild-type, miR-212/132 null (KO) and alpha-MHC miR-212/132 transgenic (TG) mice. (n=4-12).

(d, e) Representative images (d) and quantification (e) of LC3:mCherry puncta in control and miR-212/132-overexpressing transgenic H9c2 cells under normal and serum/glucose-deprivation conditions. (n=30).

(f, g) Representative electron microscopy images (f) and quantification (g) of autophagic vacuoles in control and miR-212/132-overexpressing transgenic H9c2 cells under normal and serum/glucose-deprivation conditions. (n=20).

(h, i) Representative FACS plots (h) and quantification (i) of percent increase of autophagic flux in control and miR-212/132-overexpressing transgenic H9c2 cells under normal and serum/glucose-deprivation conditions. (n=3-4 experiments).

All values represent mean±SEM. *p<0.05; **p<0.005. Scale bars represent 50 μm in d and 500 nm in f.

Figure 12:
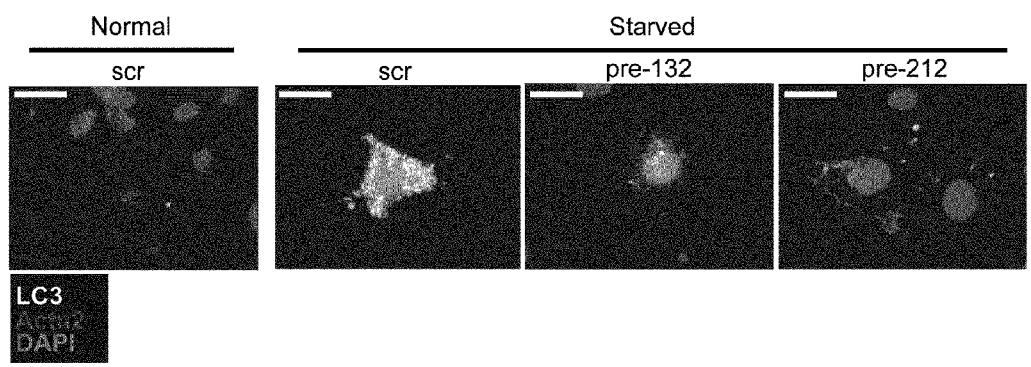
Figure 12:
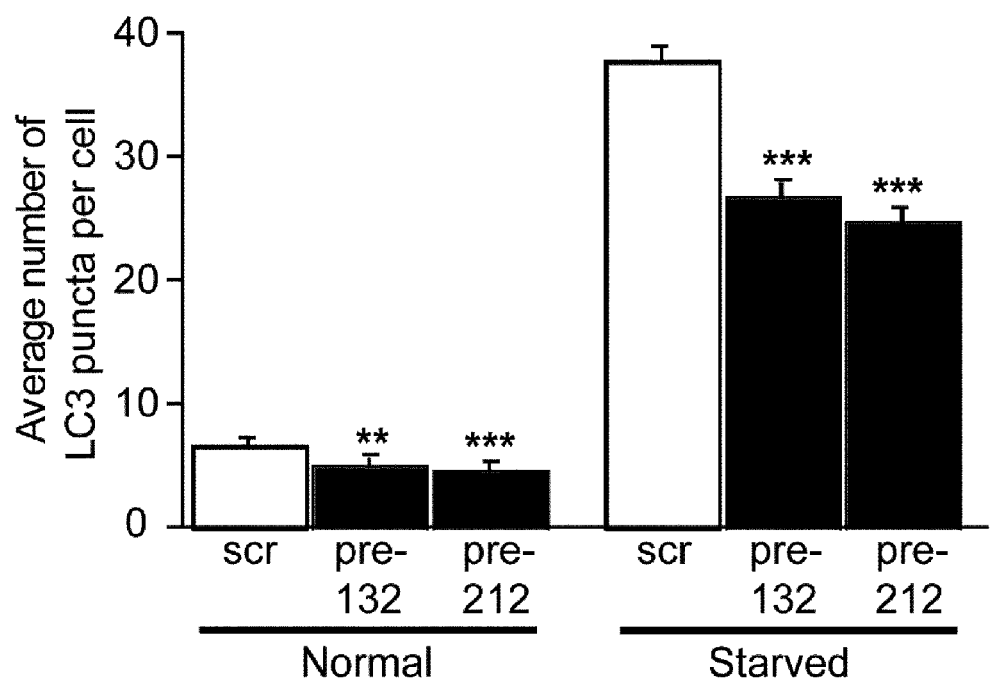

FIG. 12. miR-212/132 overexpression abrogates starvation-induced autophagy in primary cardiomyocytes.

Average numbers of LC3-GFP puncta per cardiomyocytes were quantified in normal (DMEM+10% FCS) media or starvation (glucose- and FCS-free) media after co-transfection with LC3-GFP expression construct together with scrambled control (Scr), pre-miR-212 or pre-miR-132. n=40-170 cardiomyocytes. All values represent mean±SEM. **p<0.01;

***p<0.005. Representative images are shown above the graph. Scale bars represent 10 µm.

Figure 13:
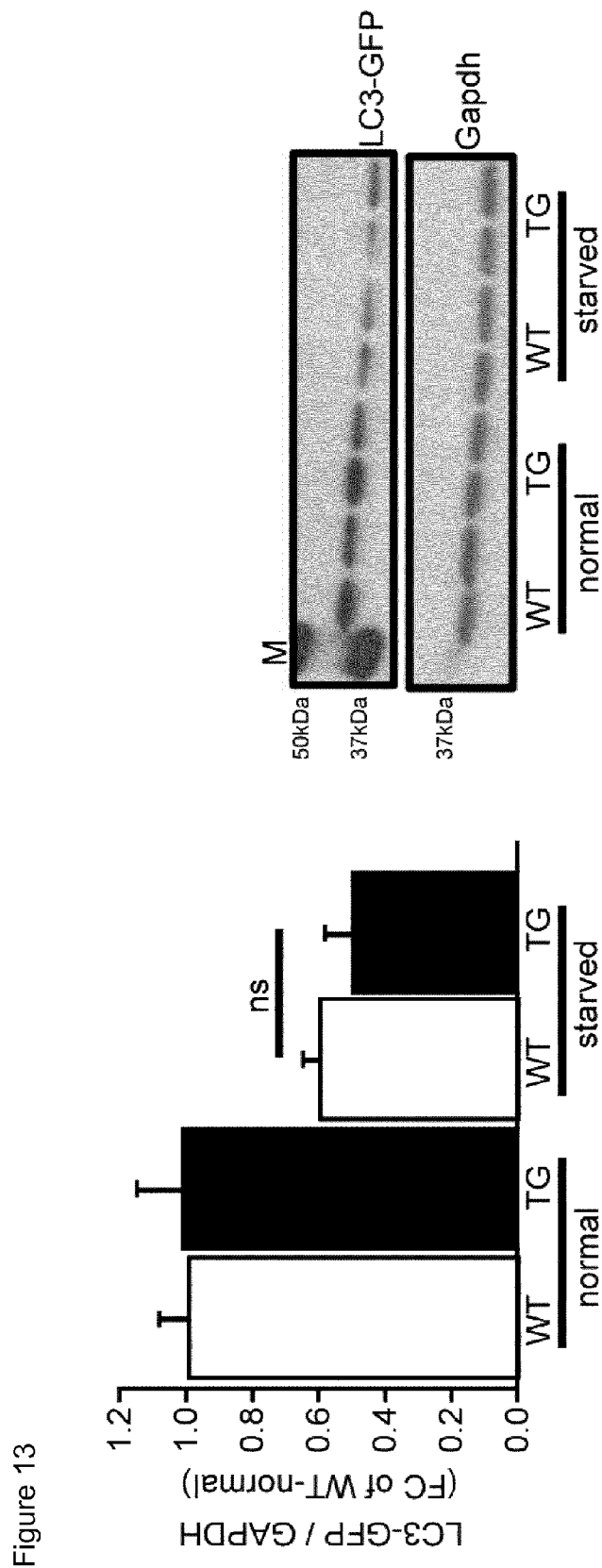

FIG. 13. Expression levels of the LC3-GFP fusion protein.

Expression of the LC3-GFP fusion protein in wild-type (WT) and miR-212/132 transgenic (TG) H9c2 cells transfected with LC3-GFP expression construct 24 h after normal and starving (glucose and serum-free medium) cell culture conditions. Values represent mean±SEM. (n=4).

Figure 14:
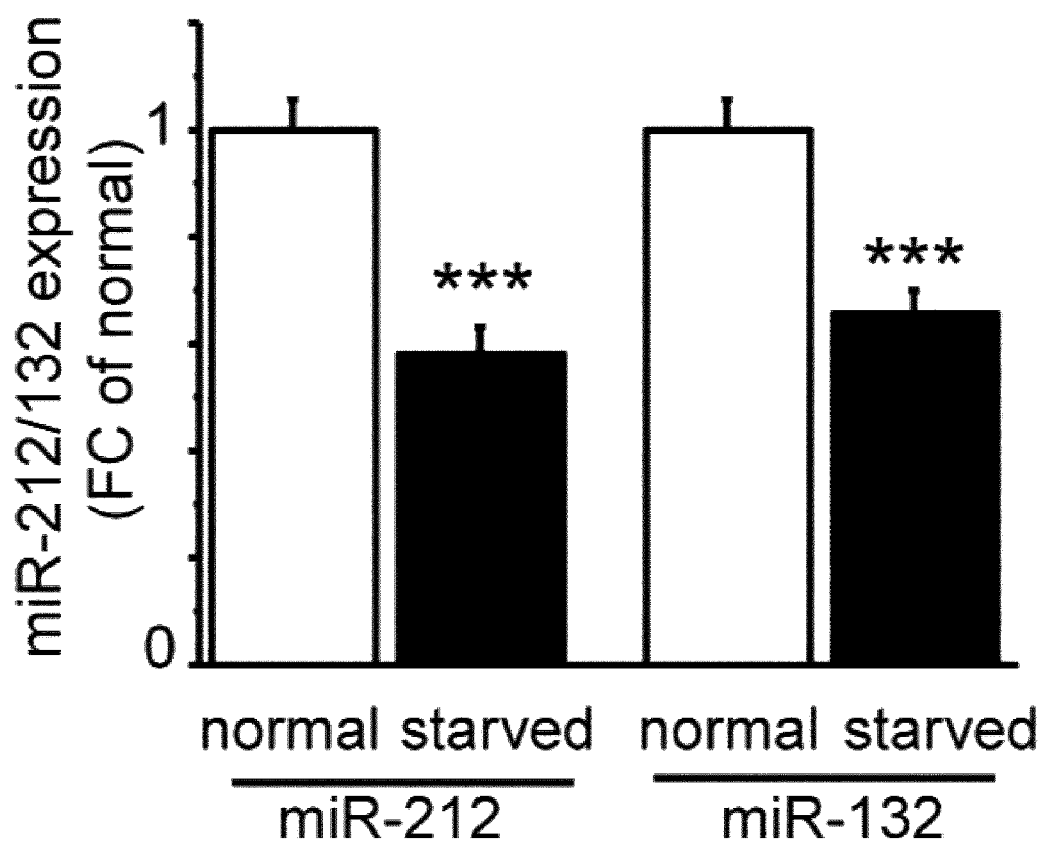

FIG. 14. Starvation leads to the downregulation of miR-212/132 expression in H9c2 cells.

Expression of miR-212 and miR-132 in H9c2 cells 24 h after normal conditions or serum/glucose deprivation. Values represent mean±SEM. ***p<0.005; (n=9).

Figure 15:
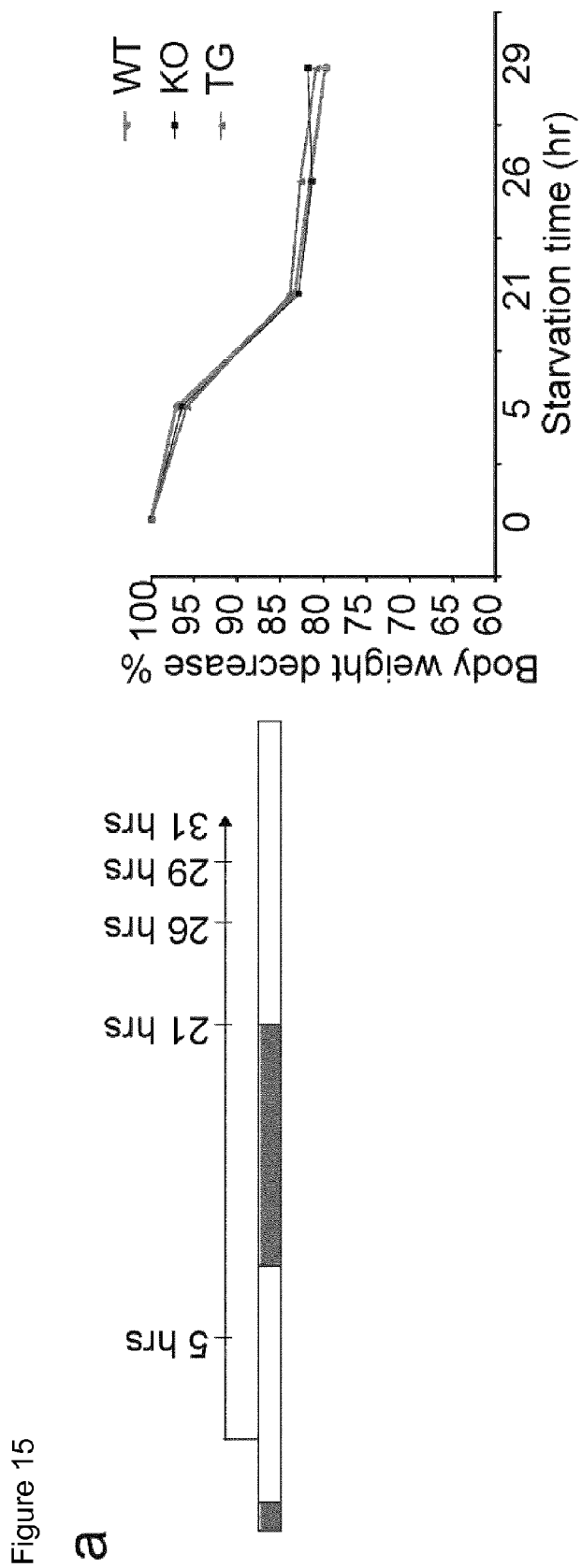
Figure 15:
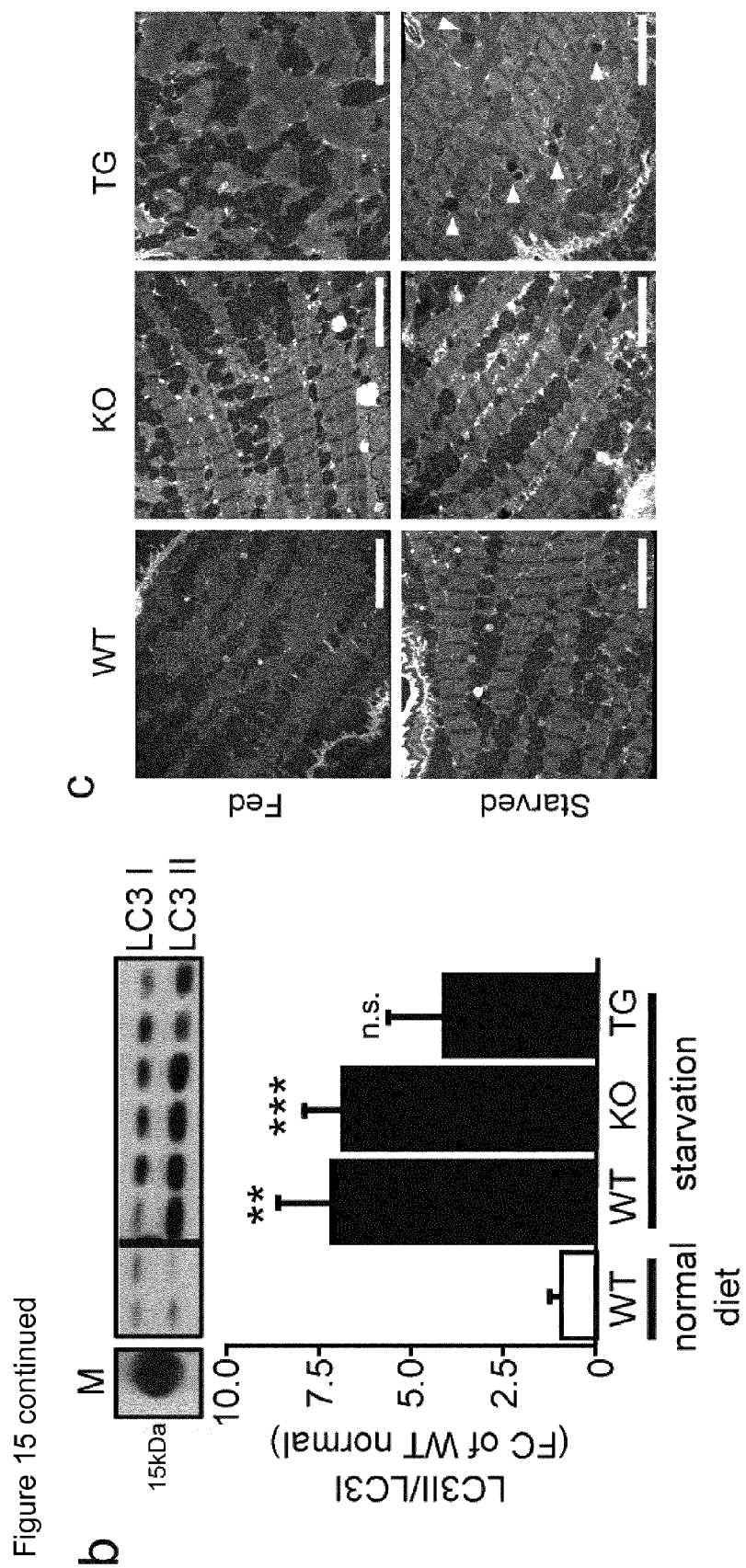
Figure 15:
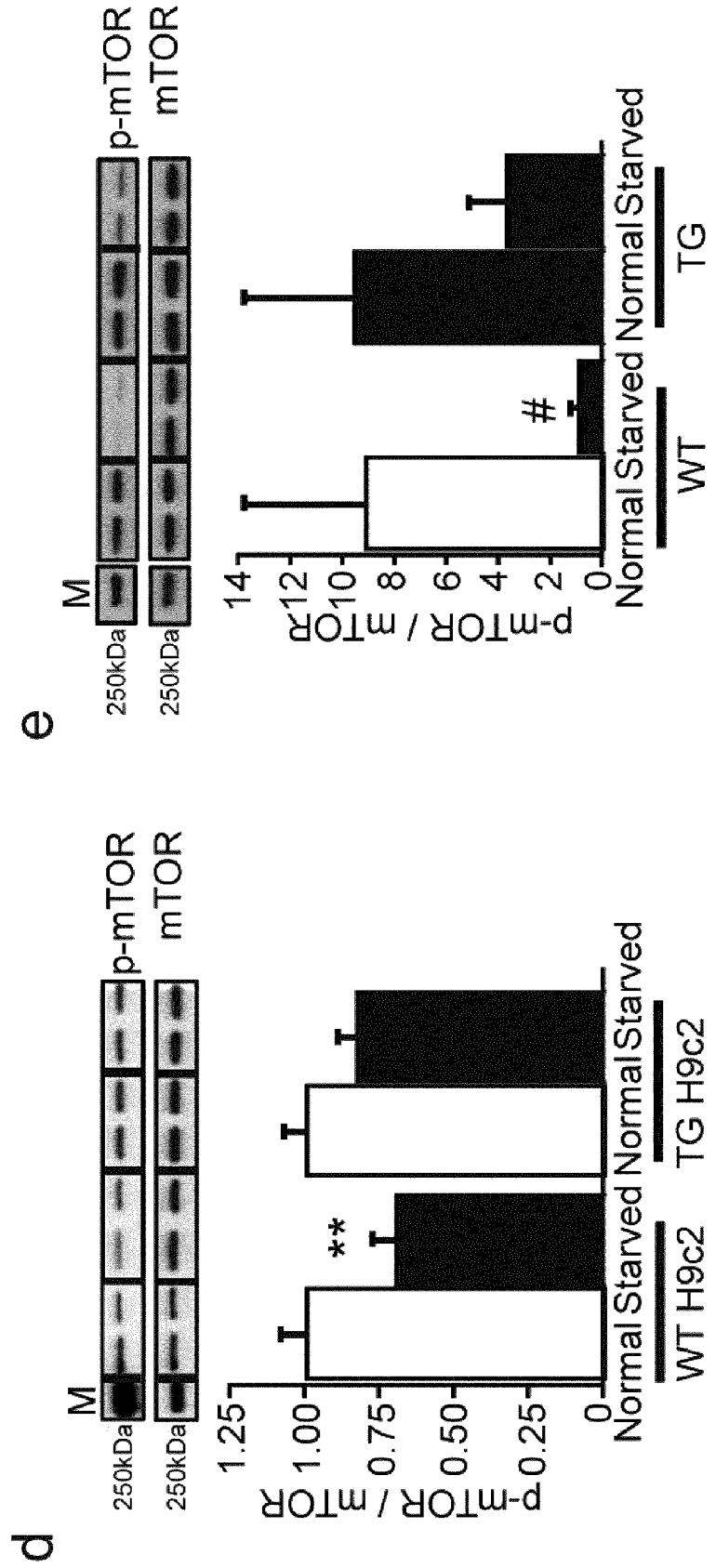

FIG. 15. MiR-212/132 inhibits starvation-induced autophagy in vivo.

(a) Schematic representation of starvation experiment in mice. The white and grey parts on the time line represent the day and night phases. The arrow shows the start and duration of the starvation and the indicated time points of starvation are when animals are scored for body conditioning index.

(b) LC3II to LC3I ratios in wild-type mice fed with normal diet and wild-type, miR-212/132−/− null and alpha-MHC miR-212/132 transgenic mice under starvation for 31 hours (n=4).

(c) Electron micrographs from ultrathin sections of resin-embedded heart biopsies of fed and starved wild-type (WT), miR-212/132 null (KO) and cardiomyocyte-specific miR-212/132 overexpressing (TG) mice. White spots around the mitochondria (dark gray structures) are autophagic vacuoles. The electron-dense black spots shown with white arrows are autophagosomes. Scale bars represent 4 µm.

(d) p-mTOR/mTOR ratios in wild-type and miR-212/132 transgenic H9c2 cells 24 h after normal and starvation (serum/glucose-deprived) conditions (n=6).

(e) p-mTOR/mTOR ratios in wild-type (WT) and alpha-MHC miR-212/132 transgenic mice (TG) fed with normal diet or 31 h after starvation (n=4).

All values represent mean±SEM. p<0.01; *p<0.005. #p=0.11.

Figure 16:
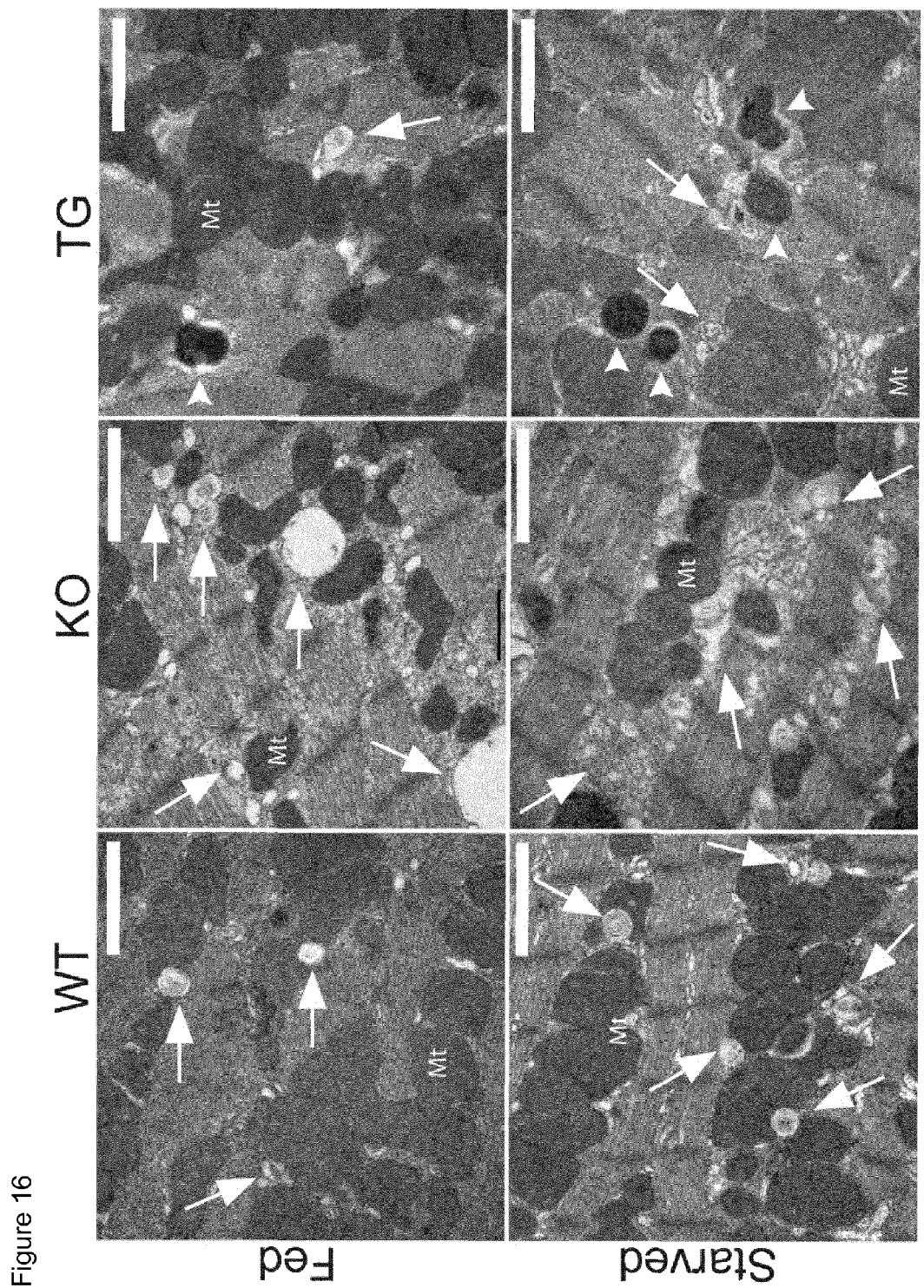

FIG. 16. Starvation-induced autophagy in the hearts of wild-type, miR-212/132 null and miR-212/132-overexpressing mice.

Higher magnification pictures of electron micrograph corresponding to FIG. 15c for the confirmation of autophagic vacuoles and autophagosomes within the cardiomyocytes. Dark grey structures are mitochondria (Mt). The translucent structures (shown with arrows) contain either convoluted membrane structures or double layers of membranes indicative of autophagic vacuoles. The electron-dense black structures (shown with arrowheads) in cardiomyocytes of TG mice are autophagosomes/autolysosomes.

Scale bars represent 1 µm.

Figure 17:
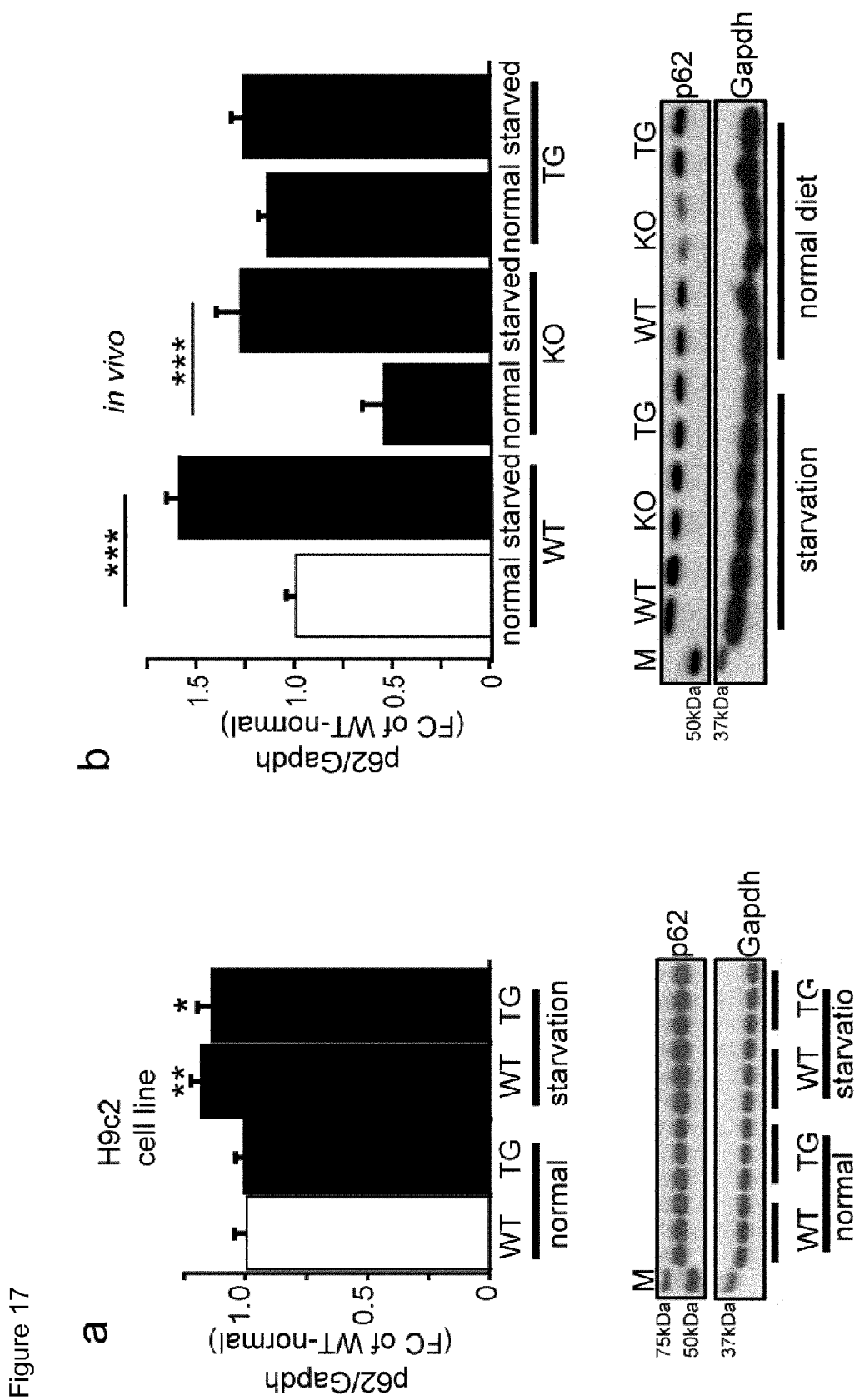

FIG. 17. Starvation leads to increased cardiac p62 levels in vitro and in vivo.

(a) Expression of p62 protein in wild-type (WT) and miR-212/132 transgenic (TG) H9c2 cells 24 h after normal and starving (glucose and serum-free medium) cell culture conditions (n=9).

(b) Cardiac expression of p62 protein in wild-type (WT), miR-212/132 null (KO) and miR-212/132-overexpressing transgenic (TG) mice after normal diet or 31 h of starvation (n=4).

Values represent mean±SEM.

*p<0.05; p<0.01; *p<0.05.

Figure 18:
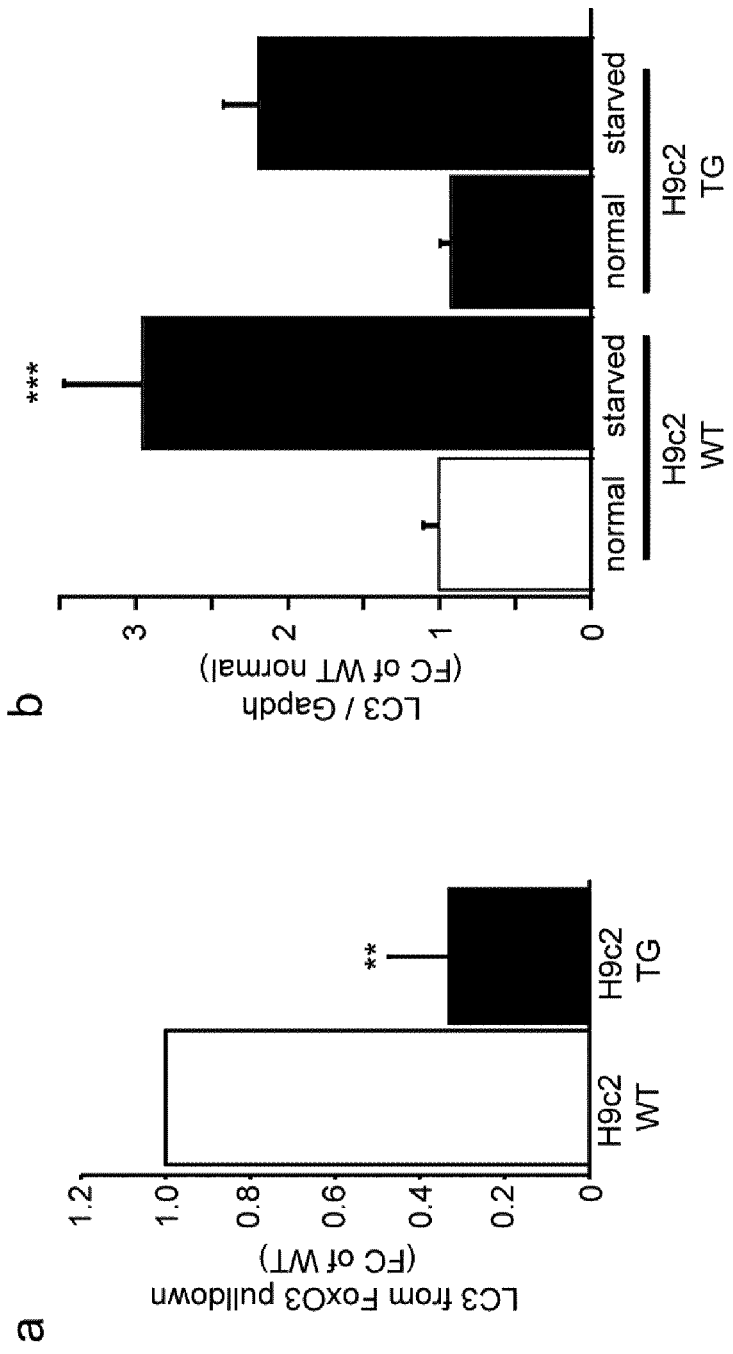

FIG. 18. Reduced FoxO3 binding to LC3 promoter in H9c2 cells overexpressing miR-212/132.

(a) LC3 promoter genomic sequence levels after chromatin-immunoprecipitation by FoxO3 from wild-type (WT) and miR-212/132 overexpressing (TG) H9c2 cells.

(b) LC3 expression levels in wild-type (WT) and miR-212/132 transgenic (TG) H9c2 cells 24 h after normal and starving (glucose and serum-free medium) cell culture conditions.

Values represent mean±SEM. p<0.01; *p<0.005; (n=3-6).

Figure 19:
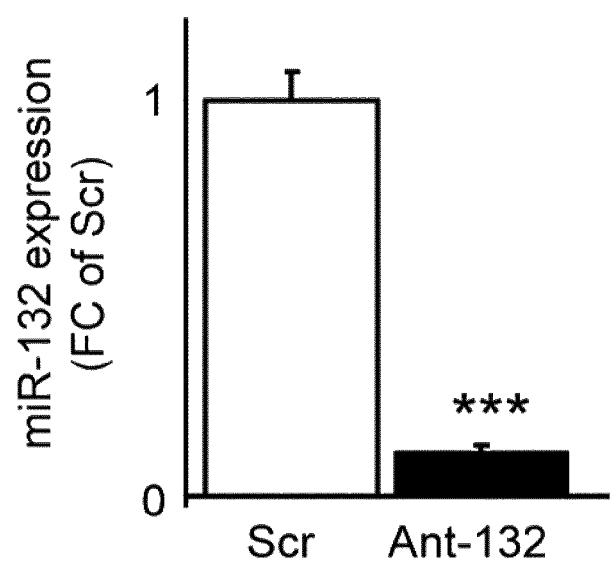

FIG. 19. Cardiac expression levels of miR-132 after antagomir treatment of left ventricular pressure-overloaded mice.

Cardiac miR-132 expression in mice three weeks after transaortic constriction and therapeutic injection of a scrambled antagomir (Scr) or an antagomir directed against miR-132 (Ant-132). Values represent mean±SEM. ***p<0.005; (n=5-14).

Figure 20:
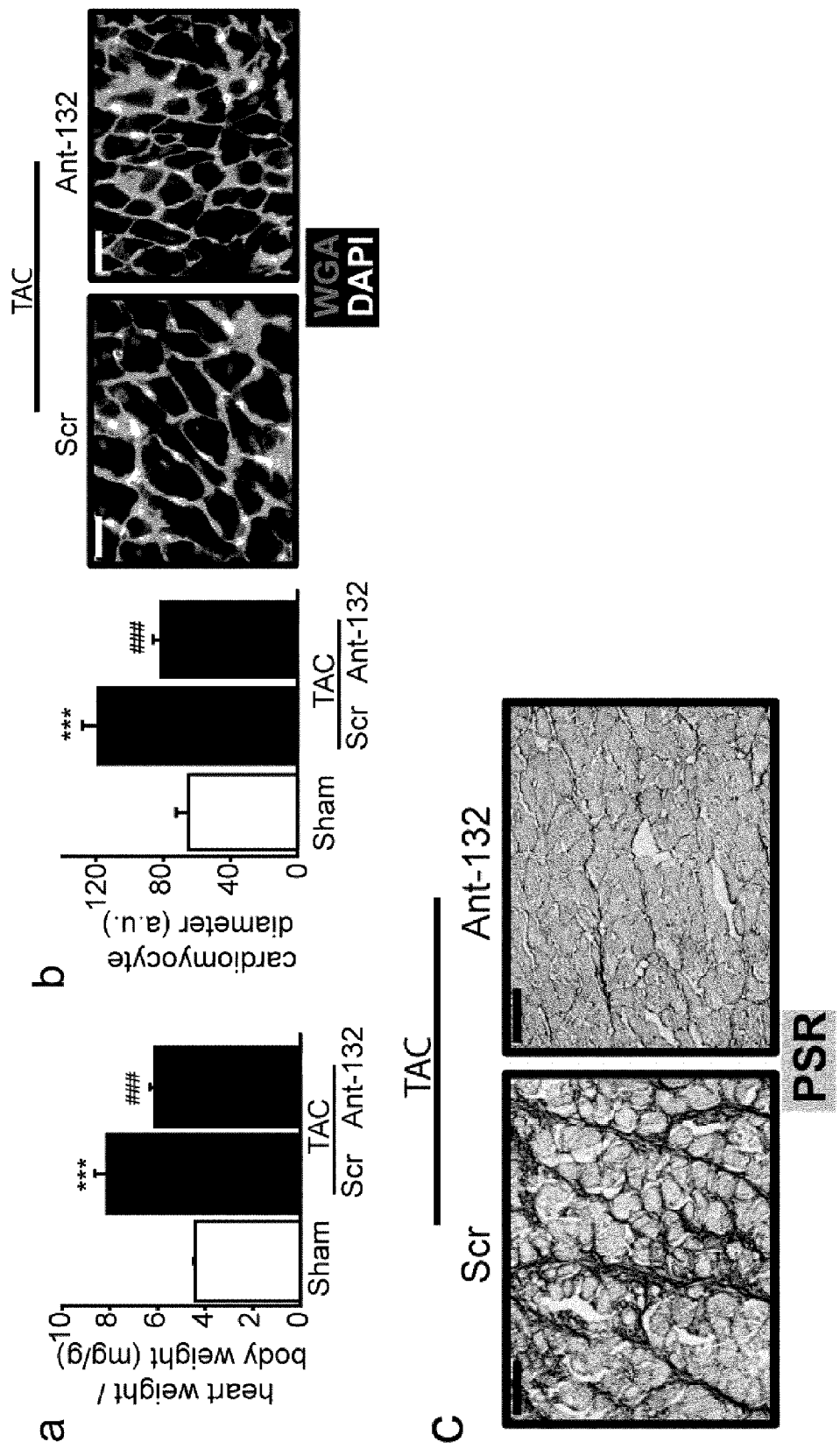
Figure 20:
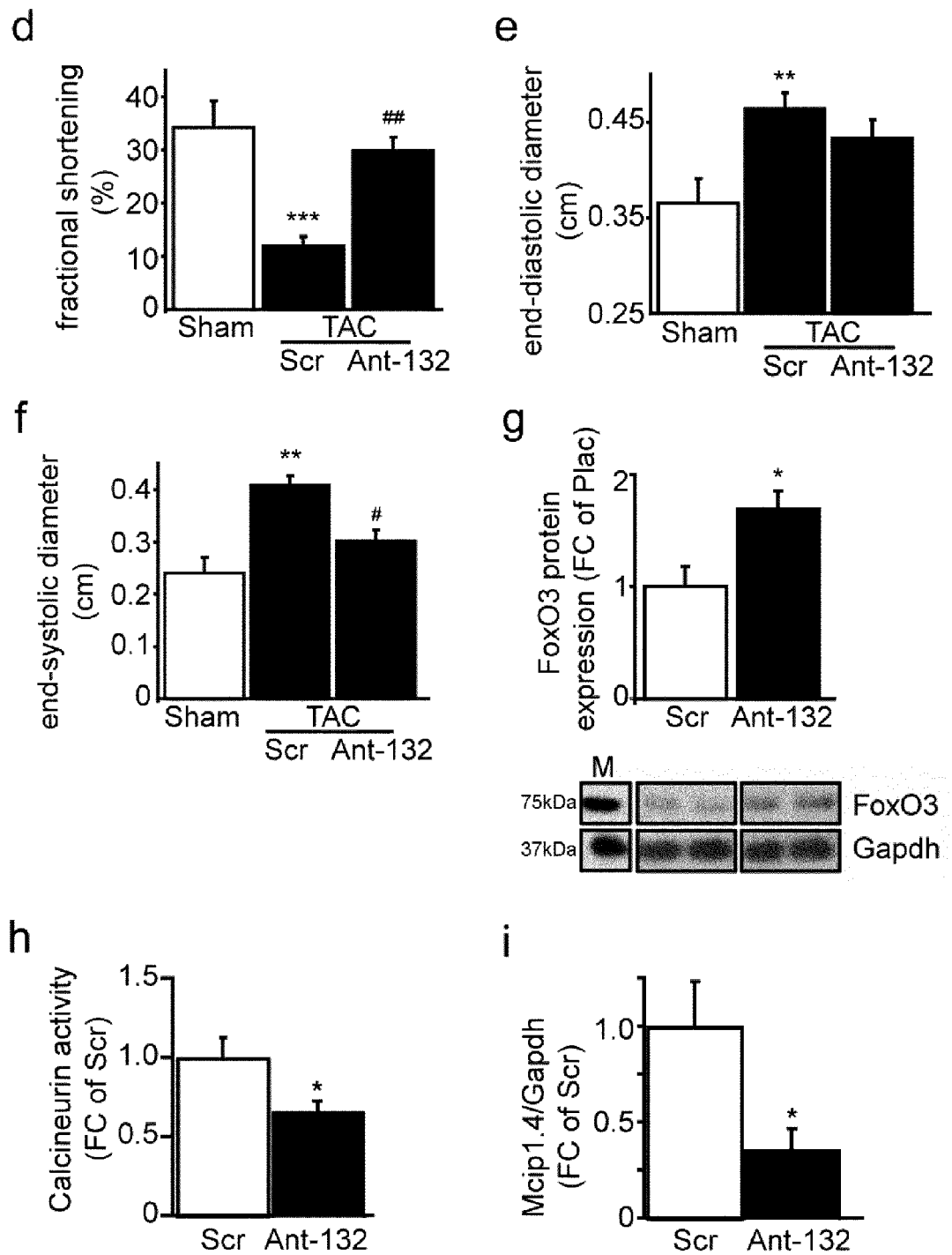

FIG. 20. Anti-miR-132 therapy prevents pressure-overload induced heart failure.

(a-c) Heart to body weight ratios (a), cardiomyocyte diameters (b), and cardiac fibrosis (c) in Sham-operated mice and mice treated with intravenous injection of either scrambled control (Scr) or miR-132 inhibitors (Ant-132) after TAC. These mice were analyzed three weeks after TAC. (n=4-11).

(d-f) Echocardiographic analysis of cardiac dimensions and function in Sham-operated mice and mice treated with intravenous injection of either control (Scr) or miR-132 inhibitors (Ant-132) after TAC. These mice were analyzed three weeks after TAC ((d) fractional shortening, (e) end-diastolic area, (f) endsystolic area). (n=4-9).

(g-i) Cardiac FoxO3 protein levels (g), calcineurin activity (h) and Mcip1.4 mRNA levels (i) in mice treated with intravenous injection of either control (Scr) or miR-132 inhibitors (Ant-132) three weeks after TAC and treatment (n=4-8).

All values represent mean±SEM. *p<0.05; p<0.01; *p<0.005; #p<0.05 against TAC-control; ##p<0.01 against TAC-control; ###p<0.005 against TAC-control. Scale bars represent 50 µm.

Figure 21:
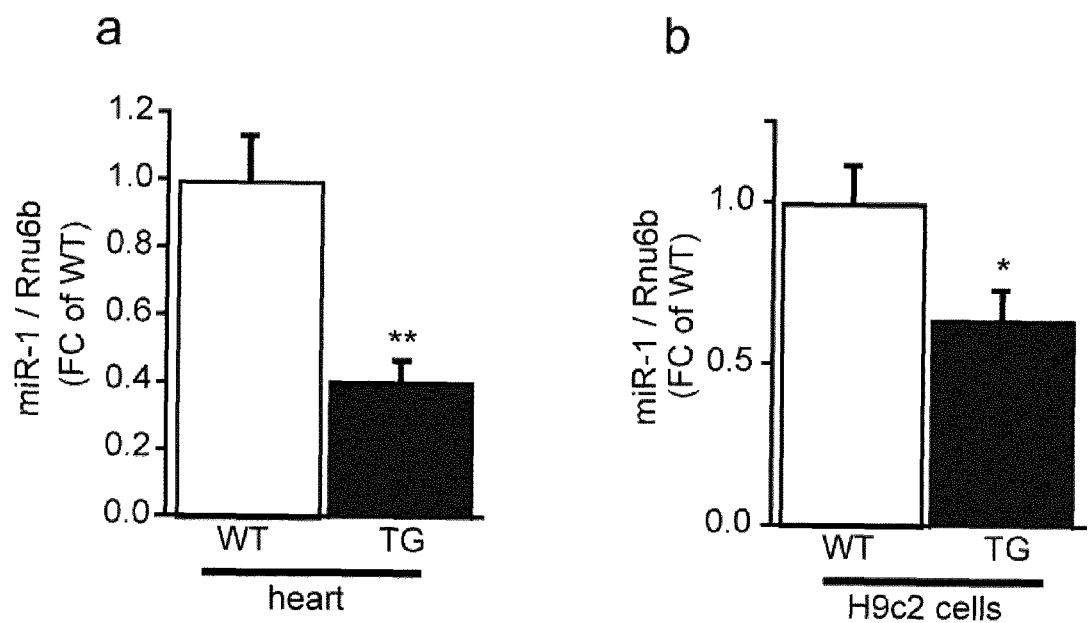

FIG. 21. miR-1 expression is regulated by the miR-212/132 family.

(a) miR-1 expression levels in hearts of wild-type (WT) and miR-212/132-overexpressing transgenic (TG) mice (n=5 per group).

(b) miR-1 expression levels in wild-type (WT) and miR-212/132-overexpressing transgenic (TG) H9c2 cell lines (n=8 per group).

Values represent mean±SEM. *p<0.05; **p<0.01.

EXAMPLES

1. Methods 1.1 Cell Culture Studies

Primary cardiomyocytes were prepared from neonatal mice or rats using standard protocols. Cardiomyocyte cell line H9c2 and the primary cardiomyocytes were maintained in DMEM+10% FCS. Cardiomyocyte cell line HL1 was maintained in Claycomb medium+10% FCS. For both stable and transient transfection of these cells, Lipofectamine 2000 reagent (Invitrogen) was used according to the manufacturer's protocol. For the screen of prohypertropic microRNAs, miRNA precursor library (Pre-miR™ miRNA Precursor Library-Mouse V3; Ambion; each 50 nM) was used. For measurement of cell size, cells were fixed with 4% PFA and surface area of cardiomyocytes was calculated using the AxioVison Rel 4.4 package (Carl Zeiss GmbH). The percentage of cells undergoing apoptosis in primary cardiomyocyte or cell line cultures was determined by staining with annexin V and propidium iodide followed by FACS analysis (annexin- V-FLUOS kit, Roche). To measure proliferative capacity in miRNA-modulated cells, a WST-1 proliferation assay (Roche, Germany) was performed according to the manufacturer's protocol.

To generate stably-transfected miR-212/132 overexpressing transgenic H9c2 cell lines, an expression construct was prepared by cloning the whole miR-212/132 genomic locus (3.4 kb) downstream of a CMV promoter within the pTARGET vector (Promega). The expression construct used contained a neomycin gene under the control of a PGK promoter. The prepared construct or the original pTARGET vector (as control) were used in transfection experiments of the H9c2 cell line using Lipofectamine 2000 reagent (Invitrogen) according to the manufacturer's protocol. After transfection, cells were cultured in DMEM with 10% FCS and 1 mg/ml G418 (Roche) for 8 days. 2 independent transfections for both miR-212/132 overexpression construct and the control construct were prepared. After the initial G418-mediated selection, the stably-transfected cells were cultured during maintenance and the experiments with 0.5 mg/ml of G418.

1.2 Animal Studies

All animal studies were performed in accordance with the relevant guidelines and regulations and with the approval of the responsible local and national authorities. MiR-212/132 loss-of-function mutant mouse line was generated previously (Ucar et al., 2010). The mouse line was backcrossed into C57BL/6N background for at least 7 generations. For the generation of the transgenic mouse lines with the cardiomyocyte-specific overexpression of miR-212/132, a 486 bp genomic region of the miR-212/132 genomic locus, containing the sequences encoding the hairpin-stem loop sequences of both miR-212 and miR-132, was cloned downstream of the third exonic sequence of α-MHC gene and upstream of the hGH polyA signal sequence as shown in FIG. 4A. The linearized construct was microinjected into the pronuclei of fertilized eggs. Two independent founder lines were obtained with the heart-specific overexpression of miR-212/132. Afterwards, both lines were backcrossed into C57BL/6N background for at least 6 generations.

1.3 Transaortic Constriction (TAC) Model and Antagomir Application

Transaortic constriction (TAC) was performed on male C57BL/6 mice (10-12 weeks old) from Charles River Laboratories or alpha-MHC-miR-212/132 transgenic mice or their littermate controls essentially as described (Rockman et al., 1991). Antagomirs were synthesized as described (Krützfeldt et al., 2005) and were directed against miR-132 (5' CGAC-CAUGGCUGUAGACUGUUA-chol-3', wherein in "chol" is cholesterol) or a scrambled sequence (placebo control). Treatment started during the TAC operation and animals received control or antagomir-132 injections by retroorbital injection (day 0 and day 1, 0.1 ml volume containing antagomir-132 or control (each 80 mg per kg body weight)).

1.4 In vivo Starvation Experiments

We performed in vivo starvation experiments as described earlier (Kanamori et al., 2009) with some modifications. For animals to be starved, we placed them in single cages with no access to food, but ad libitum access to water 3 hours after the start of the light-phase. Together with the animal ethics department, we established an ethically acceptable protocol for starvation using the published 'body condition scoring' criteria (Ullman-Cullere & Foltz, 1999), which showed a period of 31 hours of starvation as maximally tolerable.

Accordingly, we monitored all the starving mice during the experiment and evaluated their health status based on the change in following parameters: body weight, body condition, hydration condition, alertness and reaction to provocation, and body posture, locomotion and hair coat. After 31 hours of starvation, mice were sacrificed by cervical dislocation and heart tissues were isolated and processed as described for corresponding experiments.

1.5 Cardiac Functional Analysis

Cardiac dimensions and function were analysed by pulse-wave Doppler echocardiography essentially as described (Merkle et al., 2007).

1.6 Retina Angiogenesis Model

Retina preparation and immunofluorescence were performed as previously described (Napp et al., 2012). In brief, whole eyes were fixed in 4% paraformaldehyde (PFA). Retinas were dissected, postfixed with PFA and blocked for 24 hours with PBS/BSA 1%/0.5% Triton X-100. After incubation with antibodies diluted in PBS/0.5%/0.25% Triton X-100 retinas were rinsed in PBS and mounted on a glass slide with coverslips using polyvinyl alcohol mounting medium (DAKO). The following reagents were used: Isolectin-B4-FITC (Vector, 1:100), anti-SMA-Cy3 (Sigma-Aldrich, 1:100). Stained retinas were analyzed with a fluorescence microscope (Zeiss Axiovert) using Axiovision software (Zeiss, Goettingen).

1.7 Assays for Collagen Deposition, Capillary Counting and Cardiomyocyte Diameters For analysis of collagen deposition, paraffin sections of the left ventricular myocardium were stained with Sirius red and picric acid. Collagen content was calculated as the percentage of the area in each section that was stained with Sirius red.

For capillary counting sections were stained for Pecam1 (CD31), Dapi and wheat germ agglutinin (WGA) and counting was done by NIKON-NIS Element Software. For each animal 4-7 regions were counted and a mean value was obtained. Cardiomyocyte surface area was determined from sections of the left ventricular myocardium stained with haematoxylin and eosin or wheat germ agglutinin coupled to Alexa488. Images were analyzed using the AxioVision (Zeiss) software packages.

1.8 Cardiac Cell Fractionation

Intact hearts were perfused with collagenase-based enzymatic solution (collagenase type II) through the aorta. Thereafter heart tissue was minced and gently passed through 1 mL syringe for 3 min to produce cell suspensions. Cell fractionation of cardiomyocytes and cardiac fibroblasts were done as described before (Thum et al., 2008).

1.9 Zebrafish Stocks and Embryos and miRNA Injections

Wildtype (strain AB) were grown and mated at 28.5° C. and embryos were kept and handled in standard E3 solution (5 mM NaCl, 0.17 mM KCl, 0.33 mM CaCl2, 0.33 mM MgSO4, $10^{-5}$% methylene blue) buffered with 2 mM HEPES (Sigma-Aldrich, St. Louis, Mo.) as previously described (Hentshel et al., 2007).

Using the Nanoject II injection device (Drummond Scientific, Broomall, Pa.), miR-132, miR-212 and scrambled controls were injected into one- to four-cell stage fertilized embryos at 5 μM final concentration in 4.6 nl injection buffer (20 mM Hepes, 200 mM KCl and 0.01% phenol red). Photographs were taken on a SMZ-U dissecting microscope (Nikon) and processed using Photoshop 3.0 (Adobe).

1.10 miRNA Target Prediction

The miRNA databases and target prediction tools Miranda (http://wwvv.microrna.org/microrna/home.do), PicTar (http://pictar.mdc-berlin.de/) and TargetScan (http://www.target-scan.org) were screened to identify potential miRNA targets.

1.11 Quantitative RT-PCR Analyses

RNA was isolated using Trizol reagent (Invitrogen) from tissues or cultured cells. For quantitative detection of microRNA, TaqMan miRNA assays (Applied Biosystems), iScript Select cDNA synthesis kit (BIO-RAD) and iQSupermix (BIORAD) kits were used according to the manufacturer's instructions. Rnu6b was used as control for normalization. For quantitative detection of mRNA levels, cDNAs were synthesized by using oligo-dT primers and iScript Select cDNA synthesis kit (BIO-RAD). Real-time PCR analyses were performed using specific set of primers and iQSYBR Green mix (BIO-RAD). Gapdh levels were used for normalization of the gene-specific expression levels. MiRNA-1 levels were determined by a specific Taqman-RT-PCR kit for miR-1 (Applied Biosystems). Other used oligonucleotide primer sequences are depicted in Table 3.

1.12 Protein Expression Analyses

Tissue or cells were lysed with 1× Cell lysis buffer (Cell signaling) and protein isolation was done according to manufacturer's instruction. 20-40 µg of protein were loaded on SDS-PAGE gel for separation, which was followed by blotting of protein on polyvinylidene fluoride membrane in Mini Trans-Blot electrophoretic transfer cell (Bio-Rad). Afterwards, different antigens were detected using the following primary antibodies: FoxO3 (Cell Signaling #2497), pAKT (Cell Signaling #9271), Akt (Cell Signaling #9272), LC3 (Abcam ab48394), p62 (Abcam ab56416), p-mTOR (Cell Signaling #5536), mTOR (Cell Signaling #2983), GFP (Abcam ab1218) and Gapdh (Abcam ab8245). HRP-conjugated secondary antibodies and luminol/paracumaric acid/$H_2O_2$ were used for detection of the specific bands. Intensities of the obtained bands were quantified using ScionImage software.

1.13 Calcineurin and NFAT Assays

Calcineurin assay was performed using Calcineurin Cellular Activity Assay Kit (Enzo Life Sciences) according to manufacturer's instructions. End product quantification was done by measuring absorbance at 620 nm on a microplate reader (Synergy HT). For determination of NFAT activity neonatal rat cardiomyocytes were seeded into 48 well plates and transfected after 24 h with a scrambled miR control, miR-132 and miR-212 (final concentration 50 nM; Applied Biosystems, New Jersey, USA) using Lipofectamine™ 2000 (Invitrogen, Karlsruhe, Germany) according to the manufacturer's protocol. Cells were cultured for 24 h and NFAT luciferase reporter construct containing repetitive NFAT recognition sites (gift from J. Molkentin, University of Cincinnatti) was transfected as described above (final concentration: 0.75 ng/µl). 48 h later the respective groups were stimulated with phenylephrine (50 µM) for 24 h. Luciferase activity was determined using Luciferase Assay System (Promega, Mannheim, Germany) and protein concentration was measured using the Pierce BCA Protein Assay Kit (Thermo Scientific, Bonn, Germany), both according to the manufacturer's protocol.

1.14 Luciferase Reporter Assays

The 3'UTR sequence bearing seed region for miR-132/212 was cloned into SpeI and HindIII cloning site of a pMIR-REPORT vector (Ambion). We also generated clones with mutated miR-212 and miR-132 binding sites within the same 3'UTR sequence using a site-directed mutagenesis kit (Agilent Technologies). The cloned constructs were cotransfected with miRNAs of interest (Ambion) and β-galactosidase control plasmid (Promega) into HEK293 reporter cells seeded in 48-well plates using Lipofectamine-2000 (Invitrogen). In each case, 10 ng plasmid DNA and 100 nM miRNA were used. Cells were incubated for 24 h before luciferase and β-galactosidase activity were measured using the Luciferase Assay System (Promega) and Beta-Galactosidase Assay system (Promega) kits on a multi-plate reader (Biotek, Synergy HT) according to the manufacturers' instructions.

1.15 Statistical Analysis

StatView and GraphPad prism software were used to perform unpaired Student's t-test in case of two treatment groups (data sets) or one-way ANOVA following Fisher's post-test analysis for more than two groups (data sets). For the Kaplan-Meier survival assay, the log-rank (Mantel-Cox) test was used.

1.16 LC3:mCherry Transfection and Quantitation of Autophagosomes

The expression construct for the LC3:mCherry fusion protein was kindly provided by Dr. Nathan Brady (Hamacher-Brady et al., 2006). Transgenic H9c2 cell lines were seeded on coverslips and after 80% confluence they were transfected with LC3:mCherry expression construct using Lipofectamine 2000 (Invitrogen) according to manufacturer's protocol. The transfection efficiency was kept between 10-20% in order to visualize single transfected cells afterwards. For the starvation groups, 12 hours after transfection, the medium (DMEM+10% FCS) was replaced with DMEM only. After 24 hours of culturing in DMEM, the medium was replaced with DMEM without glucose (GIBCO) and kept for additional 24 hours before fixation. For the 'full medium' groups, the medium changes were done exactly at the same times as above but always with DMEM+10% FCS. After treatment, the cells were fixed with 4% PFA, counterstained with Hoechst and mounted. The images of transfected cells were taken using a confocal laser scanning microscope (FluoView 1000; Olympus) with a 60× oil objective using the sequential scanning mode. Collected images were analyzed using ImageJ software with a special macro designed for the quantification of LC3 puncta in fluorescent images.

1.17 Transmission Electron Microscopy

Transgenic H9c2 cell lines were seeded on 10-cm plates and first grown in DMEM+10% FCS till 90% confluency. Afterwards, for the 'starvation' groups, they were further cultured in DMEM only for 24 hours and then in DMEM without glucose for an additional 24 hours. For the 'full medium' groups, the medium changes are done exactly at the same times but always with DMEM+10% FCS with glucose. At the end of these treatments, the cells were fixed with 2% glutaraldehyde (EM-grade, Polysciences Germany) buffered in 150 mM Na-cacodylate pH 7.2. The culture medium was directly replaced by the fixative, followed by two changes for fresh fixative and fixation over night at 4° C. After wash in buffer, the fixed cells were scraped off, centrifuged, the pellets post-fixed in buffered 1% Osmiumtetroxide (1 h/4° C.) and embedded in low-melting agarose. Osmium-fixation was stopped with 67% ethanol and followed by en-bloc fixation with 1% uranyl-acetate. After total dehydration through graded steps of ethanol and propylen oxide, samples were embedded in epoxy-resin. Ultrathin sections were prepared at nominal thickness of 60 nm, contrasted by uranyl and lead and observed with an EM 912 (Carl Zeiss NTS, Germany). Micrographs were recorded on image plates and scanned at 17.5 µm resolution (Ditabis, Germany). The quantifications of autophagic vacuoles were done independently by two different individuals with the criteria of observing the double-membrane and vacuole space or convoluted membrane structures inside the autophagic vacuoles.

For the ultra-structural analyses of heart samples of fed and starved mice, small biopsies were prepared using fresh scalpels. Tissue pieces smaller than 1 mm³ were prepared and immediately submerged in phosphate-buffered aldehyde containing 2% formaldehyde and 2% glutaraldehyde (both EM-grade, Polysciences Germany) and stored for several days at 4° C. until proceeding for resin embedding, including postfixation with osmium and uranyl en bloc. Ultrathin sections were prepared from the cured resin-blocks at nominal thickness of 60 nm (Ultracut UCT, Leica, Germany) contrasted by uranylacetate and Reynold's leadcitrate and observed with an EM 912 (Carl Zeiss NTS, Germany). Micrographs were recorded on image plates to be scanned at 17.5 µm resolution (Micron IP-scanner, Ditabis, Germany).

1.18 FACS-based Method of Autophagic Quantitation

The expression construct for the LC3:GFP fusion protein was kindly provided by Dr. Nathan Brady (Hamacher-Brady et al., 2006). Stably-transfected H9c2 cells were seeded in 12 well plates one day prior to transfection, which is done by using LC3:GFP construct and Lipofectamine 2000 (Invitrogen) according to the manufacturer's protocol. 6 hours post transfection, the medium was changed with DMEM+10% FCS (full medium) and incubated for 24 hours. Afterwards, for control groups the full medium was given and for starvation groups the medium was changed with DMEM (no glucose+no FCS) to induce autophagy. 24 hours later the cells were harvested and captured on Canto BD for FACS analysis. FACS data was analyzed using FlowJo software.

1.19 FoxO3-chromatin-immunoprecipitation (ChIP) Assay

Chromatin immunoprecipitation for FoxO3 in H9c2 cells was performed with the MAGnify™ Chromatin Immunoprecipitation System (Invitrogen). In brief, 200.000 cells were used for formaldehyde crosslinking. Immunoprecipation was carried out with 5 µg FoxO3 antibody (sc-9813x, Santa Cruz) or control antibody (sc-2028, Santa Cruz). Subsequent RT-PCR analysis of immunoprecipitated chromatin was performed applying primers as depicted in Table 3.

2. Results

The functional significance of re-expression of certain miRNAs in heart disease is not well understood. In order to determine individual miRNAs that induce hypertrophy in cardiomyocytes, we transfected neonatal rat cardiomyocytes with a precursor miRNA library and studied in parallel changes in cardiomyocyte size and secretion of brain natriuretic peptide (BNP), which is a marker of cardiomyocyte hypertrophy. By using a threshold of more than 20% of cardiomyocyte size induction, we identified 26 cardiomyocyte-expressed pro-hypertrophic miRNAs, of which ten miRNAs (miR-19a, miR-19b, miR-22, miR-26, miR-132, miR-194, miR-195, miR-212, miR-365, miR-668) also induced a strong secretion of the cardiac stress marker BNP (above the mean). Interestingly, the strongest effect on cardiomyocyte hypertrophy was seen after overexpression of miR-212, which together with miR-132 comprises the evolutionary conserved miR-212/132 family of miRNAs (FIG. 1a).

2.1 Hypertrophy Induced miRNAs, miR-212 and miR-132, Are Both Sufficient and Required for the Induction of Cardiomyocyte Hypertrophy in vitro.

Based on our initial miRNA library screen, we then focused on the cardiac function of the miR-212/132 family. Validation experiments confirmed that the overexpression of either pre-miR-212 or pre-miR-132 leads to a cell size enlargement in both primary neonatal cardiomyocytes and cardiomyocyte cell lines (H9c2, HL-1) (FIGS. 1b, 1c and FIGS. 2a, 2d), indicating that both miR-212 and miR-132 are independently sufficient to induce hypertrophy. Moreover, co-transfection of both pre-miR-212 and pre-miR-132 demonstrated additive effects on cardiomyocyte size. Knockdown of these miRNAs with specific miRNA inhibitors in both primary cardiomyocytes and cardiomyocyte cell lines decreased the cell size (FIGS. 1b, 1c and FIGS. 2b, 2e) indicating that they are not only sufficient, but also required for the physiological enlargement of the cardiomyocytes.

Expression levels of both miR-212 and miR-132 were upregulated in primary cardiomyocytes upon treatment with different hypertrophic stimuli, such as angiotensin 2 (Ang2), insulin-like growth factor-1 (IGF-1), phenylephrine/isoprenaline (P/I) and fetal calf serum (FCS), suggesting that the miR-212/132 family is functionally involved in hypertrophic processes induced by different pro-hypertrophic pathways in vitro (FIG. 1d). To determine if the miR-212/132 family would be also upregulated in hypertrophic conditions in vivo, we induced cardiac stress in wild type mice via transaortic constriction (TAC) and showed that cardiac expression levels of both miR-212 and miR-132 are increased during cardiac hypertrophy (FIG. 1e). Of note, this upregulation paralleled the development of cardiac hypertrophy after pressure overload, which is evident by the increase of cardiomyocyte diameter in these hearts (FIG. 1f). To determine which cell types of the heart mainly contribute to this hypertrophy induced upregulation of miR-212 and miR-132 in vivo, we employed cell fractionation experiments using hearts of Sham- and TAC-operated mice (5 weeks post-TAC). Our results indicated a significant increase in miR-212 and miR-132 expression levels in isolated cardiomyocytes, but not in cardiac fibroblasts. (FIG. 1g, h).

Taken together, these results demonstrate that the expression of the miR-212/132 family is induced in cardiomyocytes during hypertrophy both in vitro and in vivo. Both miR-212 and miR-132 are shown to be necessary and sufficient for the induction of hypertrophy of cardiomyocytes in vitro.

To further elucidate the functional roles of miR-212/132 family in cardiomyocytes, we generated stable H9c2 transgenic cell lines over-expressing miR-212/132 (about 10-fold increase; FIG. 3a) under a constitutively active CMV promoter. Additional transgenic H9c2 cell lines were generated as controls by using the similar construct but excluding the miR-212/132 encoding sequence. In the transgenic cell lines, over-expression of miR-212/132 increased average cell size (FIG. 2c) as well as the growth rate in culture (FIG. 3b). To investigate the cause of higher cell growth rates in miR-212/132-overexpressing H9c2 cells, we further analyzed the proliferation and apoptotic indices. Compared to controls, the over-expression of miR-212/132 lead to a decrease in the number of apoptotic cells (FIG. 3c) both under low and high FCS conditions. However, cell proliferation was not affected by miR-212/132 overexpression (FIG. 3d), indicating that higher cell growth rates observed in miR-212/132-overexpressing H9c2 cells are due to decreased apoptotic events rather than an increase in proliferation. These results demonstrate that miR-212/132 family regulates both apoptosis and hypertrophic growth of cardiomyocytes in vitro.

2.3 Cardiomyocyte-specific Overexpression of the miR-212/132 Family Induces Cardiac Hypertrophy and Heart Failure in vivo.

In order to elucidate whether miR-212/132 overexpression is sufficient to induce cardiac hypertrophy also in vivo, we generated a transgenic mouse line with cardiomyocyte-specific overexpression of miR-212/132 under the control of an α-MHC promoter (FIG. 4a). We obtained and analyzed two different transgenic families (Fam23 and Fam43) originating from two independent founder lines. The cardiomyocyte-specific overexpression of both miR-212 and miR-132 was verified by RT-PCR analyses on the heart, kidney and brain samples obtained from mice of both transgenic families compared to their wild type littermates (FIG. 4b and data not shown). The transgenic mice were born according to the expected Mendelian ratio and did not exhibit obvious defects upon birth. However, the life expectancy of these transgenic mice was reduced to an average of 84 and 119 days for Fam23 and Fam43, respectively (FIG. 4c). All transgenic mice from Fam23 and Fam43 died with clinical signs of severe heart failure within 4 or 6 months after birth, respectively. Interestingly, miR-212 and miR-132 levels in Fam 23 were 2- and 4-fold higher compared to Fam43, respectively. Thus higher cardiac miR-212/132 expression levels correlated with decreased survival.

Explanted hearts from transgenic mice were significantly enlarged (FIG. 4d). We quantified the heart to body weight ratios from different age groups of both transgenic families compared to their wild type littermates and showed progressive increase of heart mass during adolescence of transgenic mice (FIGS. 4e and 5a). The expression levels of cardiac stress markers atrial natriuretic peptide (ANP) and BNP were dramatically increased in transgenic hearts (FIGS. 5b and 5c), indicating development of heart failure. Although the expression level of α-MHC was not altered in transgenic hearts (FIG. 5d), the level of β-MHC were also strongly increased in transgenic hearts (FIG. 5e), indicating the reactivation of the 'fetal' gene program and thereby confirming the existence of pathological cardiac remodeling in these mice. β-MHC is the isoform of MHC, which is normally expressed highly in fetal hearts and gets reactivated in failing hearts (Hill and Olson, 2008; Barry and Townsend, 2010). In addition, we also observed an increase in the phospho-Akt levels in miR-212/132-overexpressing transgenic hearts (FIG. 5f). However, this is likely to be an indirect effect of the developing cardiac hypertrophy in these mice rather than being the direct consequence of miR-212/132 overexpression, since phospho-Akt levels were unchanged in miR-212/132 overexpressing H9c2 cells in vitro (FIG. 5g).

Morphologically, cardiomyocyte diameter as determined in histological sections of transgenic hearts versus controls was significantly increased (FIG. 4f). Cardiac function in transgenic mice was evaluated in comparison to their wild type littermates by small-animal echocardiography (FIGS. 4g-i). We observed significant end-systolic and end-diastolic left ventricular dilatation in transgenic animals (FIGS. 4g and 4h). Fractional shortening, a parameter of cardiac function, was strongly reduced in the hearts of transgenic mice compared to their wild type littermates (FIG. 4i). Basic hemodynamic evaluations confirmed impaired heart function of transgenic animals (Table 1).

Taken together, these results demonstrate that the cardiomyocyte-specific overexpression of the miR-212/132 family in mice is sufficient to induce pathological cardiac hypertrophy resulting in the development of heart failure.

To analyze the potentially conserved in vivo roles of miR-212/132 family in another species, we injected miR-212 and miR-132 precursors into zebrafish embryos. 48 hours post fertilization (hpf), the embryos showed massive cardiac oedema indicating cardiac dysfunction (FIG. 5h). These results point to an evolutionary conserved functional role of the miR-212/132 family in the regulation of cardiac function.

2.4 The miR-212/132 Family is Required for Both Physiological Heart Growth and Pathological Cardiac Hypertrophy in Mice We previously generated a loss-of-function mutant mouse line for miR-212/132 and showed that miR-212/132$^{-/-}$ mice are born with the expected Mendelian ratio and have a healthy lifespan, although female miR-212/132$^{-/-}$ mice showed an impaired mammary gland development during puberty (Ucar et al., 2010, Ucar et al. 2011). Obviously, miR-212/132$^{-/-}$ mice also lack cardiac expression of miR-212/132 (Ucar et al., 2010). We now further analyzed the miR-212/132$^{-/-}$ mouse line in order to determine whether miR-212/132 is also 'necessary' for either the physiological heart growth or pathological cardiac hypertrophy in mice. The heart versus body weight ratio of adult miR-212/132$^{-/-}$ mice was 12.3% smaller than that of their wild type littermates (FIG. 6a), indicating the requirement of miR-212/132 for proper physiological heart growth. Indeed, isolated primary cardiomyocytes from neonatal miR-212/132' mice had smaller cell sizes compared to those from wild type littermate controls (FIG. 6b). However, functionally there were no significant differences in cardiac parameters of wild-type and miR-212/132 null mice (Table 2).

To determine whether miR-212/132 is required for pathological cardiac hypertrophy, we applied left ventricular pressure-overload by TAC operation to miR-212/132$^{-/-}$ mice and their wild type littermates. TAC led to a significant increase in cardiac weight and cross-sectional cardiomyocyte diameters in wild type animals (FIGS. 6c and 6d). In contrast, mutant mice lacking miR-212/132 were strongly protected from TAC-induced hypertrophy (FIGS. 6c and 6d). TAC-induced cardiac fibrosis was also less present in mutant hearts (FIG. 6e). Lung weight increased significantly in wild type animals upon TAC, but to a much lower extent in miR-212/132$^{-/-}$ mice, indicating prevention of heart failure (FIG. 6f). Three weeks after TAC, wild type mice developed left ventricular dilatation and impaired cardiac function as shown by increased end-diastolic and end-systolic diameter and decreased fractional shortening (FIGS. 6g-i). In contrast, miR-212/132$^{-/-}$ mice were protected from development of cardiac dilatation and impaired left ventricular function (FIGS. 6g-i).

These results demonstrate that the function of the miR-212/132 family is not only 'sufficient' for inducing pathological hypertrophy of the heart, but also 'necessary' for both physiological and pathological hypertrophy in vivo.

Since miR-212/132 null mice bear constitutive deletion of the miR-212/132 gene in all cell types, it is necessary to investigate if the loss-of-function of miR-212/132 in cardiomyocytes or non-cardiomyocyte cells of the heart is responsible for the observed cardio-protective phenotype. By using specific miRNA inhibitors, we have already shown that the knock-down of either miR-212 or miR-132 leads to a cell size decrease of the primary cardiomyocytes (FIG. 1b, c) as well as the cardiomyocyte cell lines (FIG. 2b, e). To study potential functions of miR-212/132 family in cardiac fibroblasts, which represent the major cell fraction of cardiac non-myocytes, we knocked-down miR-132 and/or miR-212 in vitro and checked for possible effects on the proliferation, apoptosis or migratory behaviour of these fibroblasts. Our results demonstrated no significant effect on either of these processes upon loss-of-function of the miR-212/132 family (FIG. 7). Next, we employed a retinal angiogenesis assay using wild-type and miR-212/132 null mice in order to identify potential implications of miR-212/132 loss-of-function for general angiogenesis in vivo.

No differences were observed between wild-type and miR-212/132 null mice in retina size, number of retinal arteries, central artery size or number of branches per artery (FIG. 8a-c). Furthermore, we also analysed the capillary densities in the hearts of wild-type and miR-212/132 null mice but also did not find significant differences (FIG. 8d).

Taken together, the observed cardio-protective phenotype in miR-212/132 null mice is likely due to the loss-of-function of miR-212/132 family in cardiomyocytes rather than in other non-cardiomyocyte cells of the heart.

2.5 MiR-212 and miR-132 Induce Cardiac Hypertrophy Via Down-regulation of the Anti-hypertrophic Transcription Factor FoxO3

In order to elucidate the molecular functions of the miR-212/132 family in the regulation of cardiac hypertrophy, we investigated miR-212/132 downstream targets that might be involved in the phenotypic changes observed after genetic modulation of this miRNA family. We first screened predicted target genes for both miR-212 and miR-132 by using various bioinformatic tools, such as Miranda, Targetscan, and PicTar, to identify hypertrophy-associated genes. We identified the anti-hypertrophic transcription factor FoxO3 to be a predicted target of both miR-212 and miR-132. To validate this bioinformatical prediction, we cloned the 3'UTR of FoxO3 downstream of the firefly luciferase gene and found that the normalized luciferase activity was substantially reduced upon co-transfection of this construct with either miR-212 or miR-132 but not with unrelated control (scrambled) miRNAs (FIG. 9a). Mutation of the miR-212/132 binding site within the FoxO3 3'UTR abolished the repressing effects of miR-212 and miR-132 (FIG. 9a). These results validate FoxO3 as a direct in vivo target of both miR-212 and miR-132.

We then analyzed FoxO3 expression levels in hearts of transgenic mice with cardiomyocyte-specific miR-212/132 overexpression and found a reduced expression both at mRNA and protein levels when compared to hearts of their wild type littermates (FIGS. 9b and 9c). MiR-212/132 overexpression also resulted in lower FoxO3 levels in H9c2 and primary cardiomyocytes (FIG. 10 a,b). Prohypertrophic phenylephrine treatment of cardiomyocytes led to downregulation of FoxO3 expression, which could be rescued by inhibition of miR-212 or miR-132 (FIG. 9d), indicating that hypertrophy induced downregulation of FoxO3 expression is indeed mediated by the miR-212/132 family. Interestingly, we have also previously shown an association between a decrease in FoxO3 mRNA levels and human heart failure (Thum et al., 2007) indicating a significant resemblance of the observed phenotype to human heart failure also on a molecular level.

FoxO transcription factors exert their anti-hypertrophic functions largely via the suppression of the calcineurin signaling pathway (Ni et al., 2006; Ronnebaum and Patterson, 2010). FoxO3 can activate the expression of atrogin-1, which induces the ubiquitination and thus degradation of calcineurin A in cardiomyocytes (Sandri et al., 2004; Li et al., 2004). Therefore, we analyzed expression levels of atrogin-1 in hearts of miR-212/132-overexpressing transgenic mice and found a significant reduction compared to wild type hearts (FIG. 9e). Because of the miR-212/132-dependent downregulation of FoxO3 and subsequently that of atrogin-1 expression, we hypothesized that the activity of the calcineurin signaling pathway would be increased in the hearts of miR-212/132-overexpressing transgenic mice. We thus determined MCIP.1 (also known as Mcip1.4, RCAN1) mRNA expression, whose transcription is regulated directly by the calcineurin signaling pathway (Rothermel et al., 2003). We found MCIP.1 mRNA levels to be significantly increased in transgenic hearts compared to wild type controls (FIG. 9f) as well as in the transgenic H9c2 cell lines overexpressing miR-212/132 (FIG. 10c). Moreover, calcineurin dephosphatase activity was increased in cardiac lysates of miR-212/132 transgenic mice, thus confirming the hyperactivity of this pro-hypertrophic signaling pathway (FIG. 9g). The pro-hypertrophic effect of the calcineurin signaling pathway is mainly mediated by the activation of NFAT transcription factors via de-phosphorylation, which leads to their activation and nuclear transport (Okamura et al., 2000; Barry and Townsend, 2010). Therefore, we also checked the level of NFAT transcriptional activity in cardiomyocytes after transfection with pre-miR-212, pre-miR-132, or scrambled control miRNAs. Overexpression of either miR-212 or miR-132, but not the control miRNA, led to a dramatic increase in NFAT activity in both basal and in phenylephrine (PE)-induced pro-hypertrophic conditions (FIG. 9h).

In contrast, Mcip1.4 upregulation after pressure overload was blunted in miR-212/132 null mice (FIG. 9i), indicating that the activation of the pro-hypertrophic calcineurin/NFAT signalling was suppressed in the absence of miR-212/132 function. In addition, atrogin-1 levels were decreased during pressure-overload induced cardiac hypertrophy in wild-type hearts, but increased in miR-212/132 null hearts (FIG. 9k), indicating the lack of FoxO3 function and thereby explaining the suppression of the calcineurin signalling in mutant hearts.

Taken together, these results indicate that the miR-212/132 family regulates the balance between the pro- and anti-hypertrophic pathways in cardiomyocytes via its direct regulation of FoxO3 expression. In the absence of FoxO3 mediated inhibition, the hyperactivation of the pro-hypertrophic calcineurin signaling pathway and consequently the increased NFAT transcriptional activity probably leads to the observed pathological hypertrophy and the associated heart failure in the transgenic mice with cardiomyocyte-specific overexpression of miR-212/132. On the other hand, in the absence of miR-212/132 function, the unsuppressed FoxO3 activity leads to the upregulation of atrogin-1 and thereby prevents the activation of the prohypertrophic calcineurin signalling and thus the development of cardiac hypertrophy.

2.6 The miR-212/132 Family Functions as an Anti-autophagic Factor in Cardiomyocytes Besides negatively regulating hypertrophic processes, FoxO3 also induces autophagy in cardiomyocytes (Sengupta et al., 2009; Ferdous et al., 2010). To determine whether overexpression of miR-212/132 in cardiomyocytes might interfere with autophagic processes in vivo, we investigated the mRNA levels of several autophagic marker genes like LC3b, Ulk2, ATG12, Plk3c3, Beclin1, Bnip3, and ATG5b and found a dramatic decrease in the expression of all these genes in transgenic hearts compared to the levels in wild type hearts (FIG. 11a). Likewise, the LC3 lipidation levels (LC3II/LC3I ratios) were lower (FIG. 11b), whereas levels of the autophagy substrate p62 were increased in hearts of miR-212/132-overexpressing transgenic mice (FIG. 11c).

These results suggest that cardiomyocyte-specific miR-212/132 overexpression attenuates cardiac autophagic processes. Conversely, miR-212/132 null mice hearts had higher cardiac LC3 lipidation (LC3II/LC3I ratios) and lower p62 levels when compared to wild type hearts (FIGS. 11b and c), indicating higher rates of autophagy in the heart.

In order to determine whether the reduced expression of autophagy markers observed in the hearts of transgenic mice is a direct effect of miR-212/132 overexpression, we further analyzed autophagic processes in stably-transfected transgenic H9c2 cell lines. To visualize autophagosome formation and to quantify the amount of autophagic structures in individual cardiomyocytes, we transfected these cells with an expression construct for LC3:mCherry fusion protein. LC3 protein gets lipidated and then accumulates on the membrane structures of autophagosomes and therefore it is possible to visualize autophagic structures as fluorescent puncta (Hamacher-Brady et al., 2006). Under normal conditions, the average number of LC3-puncta was slightly less in the miR-212/132-overexpressing H9c2 cells compared to the controls (FIGS. 11d and 11e). Serum and glucose deprivation induce a high level of autophagy in this cell line (Aki et al., 2003). Therefore, we also induced autophagic conditions by starving the cells in serum- and glucose-free media and quantified the number of LC3 puncta in individual cells. Although the average number of LC3-puncta increased 3-fold upon starvation in control cells, it was almost unchanged in miR-212/132 overexpressing transgenic H9c2 cells, indicating that the miR-212/132 family of miRNAs negatively regulates the autophagic induction in response to nutrient limitation (FIGS. 11d and 11e).

Similar findings were also observed in primary neonatal cardiomyocytes upon starvation and miR-212 or miR-132 overexpression (FIG. 12). These results demonstrate that miR-212/132 family negatively regulates the autophagic response of cardiomyocytes to nutrient limitation.

In order to visualize autophagic structures in more detail, we used transmission electron microscopy to analyze the same transgenic cell lines in the same conditions as above and counted the number of autophagic vacuoles with double membranes. Similar to our LC3-puncta data, the autophagic response to nutrient limitation was blunted in miR-212/132-overexpressing H9c2 cells compared to the almost 2-fold increase of the number of autophagic vacuoles in control cells (FIGS. 11f and 11g). Finally, we also employed an FACS-based method for the quantitative detection of autophagic flux taken as the activity of autophagic machinery (Shvets and Elazar, 2009). The transgenic H9c2 cells were transfected with GFP:LC3 expression constructs and analyzed under either full medium condition or serum/glucose deprived conditions. The decrease in GFP fluorescence correlated with the activity levels of autophagic machinery, since the GFP fluorescence intensity reduces within the acidic environment of autolysosomes after the fusion of lysosomes with autophagosomes. We have detected a significant decrease of GFP intensity for the control H9c2 cell line after starvation compared to full medium conditions, indicating increased autophagic activity as a response to nutrient limitation. In contrary, for the miR-212/132-overexpressing H9c2 cell line, this decrease in GFP intensity was significantly reduced (FIGS. 11h and 11i), which also confirms our previous findings observed in fluorescence and electron microscopy analyses. Of note, total GFP:LC3 fusion protein levels were similar between control and miR-212/132-overexpressing H9c2 cells under the similar experimental conditions, although there was a reduction upon starvation in the same level for both groups as expected due to autophagic elimination of LC3 proteins (FIG. 13). Therefore, the difference in GFP fluorescence between the control and miR-212/132-overexpressing H9c2 cells is likely due to the reduction of the GFP fluorescence within the autolysosomes as explained above.

Taken together, we have shown, using three independent methods, that the miR-212/132 family functions as an anti-autophagic factor in cardiomyocytes, which can blunt the autophagic mechanisms under nutrient limitation conditions upon their overexpression.

In order to determine whether our findings demonstrate a biologically significant mechanism in cardiomyocytes rather than the bare consequence of high level overexpression of the two microRNAs, we checked the expression levels of both miR-212 and miR-132 in wild type H9c2 cells upon normal and serum/glucose deprived conditions. Quantitative RT-PCR results showed that the mature miRNA levels of both miR-212 and miR-132 are significantly reduced during starvation conditions compared to normal conditions (FIG. 14). This result indicates that during nutrient limitation, the cardiomyocytes downregulate the expression of miR-212 and miR-132, which are anti-autophagic, which might represent a mechanism facilitated by these cells to increase the level of autophagy to survive during the starvation conditions.

To study the potential impact of the miR-212/132 family on autophagic response to starvation in vivo, we performed further starvation experiments using both miR-212/132 loss-of- and gain-of function mutant mouse lines (FIG. 15a). As assessed by LC3 lipidation levels, starvation led to a dramatic increase in cardiac autophagy in wild-type mice, which was significantly attenuated in cardiomyocyte specific miR-212/132-overexpressing transgenic animals (FIG. 15b). Interestingly, upon starvation the levels of autophagy increased to comparable levels in wild-type and miR-212/132 null mice ($^{-/-}$) hearts (FIG. 15b). To evaluate the autophagic structures on ultrastructural level, we analysed these heart samples also by transmission electron microscopy (FIG. 15c and FIG. 16). Under normal 'fed' conditions, we observed higher numbers of autophagic vacuoles within the cardiomyocytes of miR-212/132 null mice than of the wild-type mice, indicating increased basal levels of autophagy in the absence of miR-212/132 family. Starvation induced a dramatic increase in the numbers of autophagic vacuoles in wild-type cardiomyocytes, which reached to a similar level of slightly increased autophagic vacuole numbers in cardiomyocytes of starved miR-212/132 null mice.

On the other hand, in cardiomyocytes of miR-212/132 overexpressing transgenic mice we observed very few numbers of autophagic vacuoles and the electron-dense autophagosomes under normal conditions, which only slightly increased upon starvation conditions. This result also confirms that levels of both basal and starvation-induced autophagy are blunted in cardiomyocytes with miR-212/132 overexpression.

Next, we analysed the levels of the autophagy substrate p62 under starvation conditions both in vitro and in vivo. Surprisingly, the nutrient-limitation induced an upregulation of p62 levels in both wild-type and miR-212/132 overexpressing H9c2 cells although the upregulation levels were lower in miR-212/132-overexpressing cells (FIG. 17a). Likewise, upon starvation p62 levels were also increased in hearts of wild-type and miR-212/132 null mice (FIG. 17b). On the other hand, p62 levels remained unchanged in the hearts of miR-212/132 overexpressing transgenic mice upon starvation. p62 is a LC3-binding protein, which regulates the formation of protein aggregates and is removed by autophagy (Komatsu et al., 2007). Therefore, in general p62 levels are inversely correlated with the autophagic activity. However, it is possible that under nutrient limitation conditions, p62 protein levels might increase. Indeed, it has been shown earlier that during myocardial infarction, the p62 levels increase in parallel to the increase of autophagic activity (Kanamori et al., 2011). Autophagic response to nutrient limitation is also controlled by mTOR activity (Jung et al., 2010). In the conditions of excess nutrients in the environment, AMPK activates mTOR, which in turn suppresses autophagy and increases protein levels in the cell.

In contrary, mTOR activity, revealed by phospho-mTOR levels, decreases under starvation conditions which allows the upregulation of the autophagy and suppression of protein levels in the cell. To assess the potential impact of the miR-212/132 family function on the mTOR activity levels, we analysed the phospho-mTOR levels in our transgenic H9c2 cells in vitro and the hearts of the starved cardiomyocyte specific miR-212/132-overexpressing mice. In wild-type H9c2 cells, starvation leads to a reduction of phospho-mTOR/mTOR levels (FIG. 15d), which is in agreement with the increased autophagy in these cells. In contrary, we observed only a slight but not significant decrease in starved miR-212/132 overexpressing H9c2 cells (FIG. 15d), which also supports our previous finding of blunted autophagic response in these cells.

Likewise, in the hearts of starved mice phospho-mTOR/mTOR levels dramatically decreased, although the level of downregulation was lower in miR-212/132-overexpressing transgenic hearts, demonstrating further support for the attenuated autophagic response phenotype in vivo due to the overexpression of miR-212/132 family (FIG. 15e).

The IGF-1/PI3K pathway and FoxO3 were previously shown to be main regulators of autophagy in cardiomyocytes upon starvation (Aki et al., 2003; Sengupta et al., 2009). Here, our results demonstrate that the miR-212/132 family of miR-NAs, which can be upregulated by the IGF-1 pathway (FIG. 1d) and suppresses FoxO3 expression (FIG. 9a-c), leads to impaired autophagy in cardiomyocytes and hypertrophic growth.

We performed FoxO3-ChIP assays to validate if the anti-autophagic function of miR-212/132 family is related to miR-212/132-mediated suppression of FoxO3. Indeed, upon FoxO3 ChIP significantly less LC3b promoter region could be amplified from the DNA of miR-212/132-overexpressing cells when compared to wild-type H9c2 cells (FIG. 18a). This was paralleled by lower LC3b expression in the miR-212/132-overexpressing transgenic cell line during starvation when compared to controls (FIG. 18b). These results demonstrate that the anti-autophagic function of miR-212/132 family is mediated at least in part by its regulation of FoxO3 expression.

Taken together, our results demonstrate that miR-212/132 acts as an antiautophagic factor in cardiomyocytes via regulating the expression of FoxO3. Overexpression of miR-212/132 attenuates the starvation induced autophagic response in cardiomyocytes both in vitro and in vivo. On the other hand, loss-of-function of miR-212/132 increases the basal levels of autophagy in the heart.

2.7 Pharmacological Inhibition of miR-132 in vivo with Specific Antagomirs Offers a Therapeutical Approach for Pressure Overload Induced Heart Failure Since gain-of-function of the miR-212/132 family induced hypertrophy and blunted autophagic response in cardiomyocytes and the loss-of-function rescued the pressure-overload induced cardiac hypertrophy in mice, we hypothesized that inhibition of either miR-212 or miR-132 using specific antagomirs might prevent development of pressure overload induced heart failure. To test this hypothesis, we first induced cardiac hypertrophy in wild type mice by TAC and intravenously injected specific antagomirs against miR-132. As shown by quantitative RT-PCR, endogenous cardiac miR-132 levels were successfully knocked down in mice treated with antagomir against miR-132 but not with an antagomir against a scrambled sequence (FIG. 19). Heart to body weight ratios as well as the cardiomyocyte diameters were significantly increased in control-treated animals after pressure-overload, but less affected in antagomir-132 treated mice (FIGS. 20a and 20b). In addition, antagomir-132 treated mice showed less increase in cardiac fibrosis (FIG. 20c). Moreover, cardiac function and dilatation were preserved better in antagomir-132 treated mice compared to the control-treated group (FIGS. 20d-f). In the hearts of these mice, FoxO3 expression was significantly induced upon antagomir-132 treatment compared to control-treatment (FIG. 20g). In addition, the TAC-induced increase in calcineurin activity and Mcip1.4 expression was attenuated after antagomir treatment (FIGS. 20h, i).

Taken together, these results suggest that at least in mice, the antagomir-mediated knock-down of miR-132 alone can be used to prevent the development of cardiac hypertrophy and heart failure.

3. Discussion

We here demonstrate that the miR-212/132 family plays a key role in cardiac hypertrophy and heart failure development. Both miRNAs of the miR-212/132 family are upregulated by cardiac stress in vivo and upon hypertrophic conditions in vitro. Our results showed miR-212 and miR-132 to be both necessary and sufficient for pathological hypertrophy of cardiomyocytes in vitro and cardiac hypertrophy in vivo. MiR-212/132-overexpressing transgenic mouse lines developed cardiac hypertrophy and subsequently heart failure. A similar phenotype was also observed in zebrafish, indicating an evolutionary conserved function of the miR-212/132 family in cardiomyocytes. On the other hand, miR-212/132$^{-/-}$ mice were protected from pathological cardiac hypertrophy induced by pressure-overload. Similarly, pharmacologic inhibition of miR-132 by antagomir injection blocked cardiac hypertrophy and development of heart failure.

Our results show that both miR-212 and miR-132 target and negatively regulate the expression of the FoxO3 transcription factor, a powerful anti-hypertrophic and pro-autophagic factor in cardiomyocytes (Sengupta et al., 2009; Ni et al., 2006). The down-regulation of FoxO3 expression upon overexpression of miR-212/132 results in the hyperactivation of the calcineurin signaling pathway and NFAT transcriptional activity, which subsequently leads to the hypertrophy of cardiomyocytes both in vitro and in vivo. The downregulation of FoxO3 expression might also blunt the autophagic response of cardiomyocytes in order to cope with the starvation conditions. On the other hand, the genetic loss-of-function of miR-212/132 family or the antagomir-mediated knock-down of miR-132 suppresses the pressure-overload induced hypertrophic calcineurin/NFAT signalling and thereby attenuates the development of cardiac hypertrophy.

Indeed, we provide evidence for the miR-212/132 family to regulate cardiac autophagy, a process to be tightly linked to cardiac homeostasis. The overexpression of the miR-212/132 target FoxO3 has been shown to reduce cardiomyocyte cell size and to induce cardiac autophagy (Sengupta et al., 2009). Conditions with reduced cardiac autophagy lead to the accumulation of partly degraded and sometimes toxic breakdown products, which finally lead to heart failure (Taneike et al., 2010). Reduced cardiac autophagy has been associated with age-related cardiomyopathy (Taneike et al., 2010).

Since cardiomyocyte-specific overexpression of miR-212/132 impaired autophagy both in vitro and in vivo and led to severe heart failure development in mice, it is possible that the dysfunction of the autophagic response mechanisms might contribute to the observed cardiac death in this transgenic mouse line.

Pharmacological inhibition of miR-132 upregulation increased cardiac FoxO3 levels and rescued pressure-overload induced cardiac hypertrophy and failure, thus providing a valuable therapeutic target to interfere with disease-associated autophagy processes.

However, our results do not provide a mechanistic link between autophagy and cardiac hypertrophy, but rather demonstrate two different functions of miR-212/132 family in the heart. Cardiomyocytes are extremely sensitive to nutrient limitation conditions and cope with starvation by activating their autophagic response mechanism. In this study, we have shown both in vitro and in vivo that miR-212/132 family has anti-autophagic function in cardiomyocytes, which can attenuate this starvation-induced autophagic response upon their overexpression. On the other hand, miR-212/132 loss-of-function mice also showed higher levels of basal autophagy under normal conditions.

MiRNAs can regulate several gene targets simultaneously in a cell. In this study, we showed that both miR-212 and miR-132 can directly regulate the expression of FoxO3 which allowed us to demonstrate the molecular mechanisms underlying the observed loss-of- and gain-of-function phenotypes. However, we cannot rule out the possibility of miR-212 and/or miR-132 regulating other targets, which may also contribute to the observed phenotypes in both approaches. MiR-212/132 is expressed also in non-myocyte cells of the heart, although at lower levels compared to cardiomyocytes.

Importantly, the hypertrophy-induced upregulation of miR-212 and miR-132 was observed exclusively in the cardiomyocytes but not in cardiac fibroblasts. Furthermore, in vitro modulation of miR-212/132 expression did not lead to any obvious phenotypical changes in proliferation, apoptosis or migratory behaviours of cardiac fibroblasts. We were also not able to show either a defect in general angiogenesis or the capillary densities in the heart due to the loss-of-function of miR-212/132 family. Finally, since the cardiomyocyte-specific overexpression of miR-212/132 shows the opposite phenotype of the miR-212/132 loss-of-function phenotype in mice, it is highly likely that the cardioprotective effect of miR-212/132 loss-of-function is due to its function in the cardiomyocytes rather than in non-myocyte cells of the heart. Nevertheless, we can not completely rule out any minor contribution of the loss-of-function of miR-212/132 in non-myocyte cells partially leading to the observed cardioprotective phenotype in these mice. We recently demonstrated FoxO3 to partly regulate cardiomyocyte-specific miR-1 levels (Kumarswamy et al., 2012). Here, we observed significantly reduced cardiac miR-1 expression in miR-212/132-overexpressing transgenic mice and H9c2 cell lines (FIGS. 21a and b), which may also contribute to the observed heart failure phenotype.

Specifically, intravenous injection of specific antagomirs against miR-132 rescued cardiac hypertrophy and subsequent heart failure in mice after left ventricular pressure overload. The currently used therapeutic pharmacologic options for heart failure include angiotensin modulating agents, β-blockers, diuretics, aldosterone antagonists, vasodilators or ionotrophic agents (Barry and Townsend, 2010). Although several clinical studies have shown significant decreases in heart failure-induced mortality rates for all these agents, the 5-year mortality rate remains unacceptably at almost 50% (Barry and Townsend, 2010). Thus, there is a great urge to develop novel and more efficient therapeutic approaches for heart failure. In this respect, our findings by using intravenous injection of antagomirs against miR-132 after the induction of pressure overload in mice, which showed a beneficial outcome and prevented the development of the heart failure, offer a promising novel therapeutic approach for pressure overload induced heart failure.

By using both gain-of- and loss-of-function approaches, this study demonstrates that the evolutionary conserved miR-212/132 family has conserved pro-hypertrophic functions in the heart and also demonstrates that their tightly regulated appropriate expression levels are necessary for normal physiological growth and function of the heart. Although the regulation of autophagy by an miRNA was shown previously for miR-30 in cancer cell lines (Zhu et al., 2009), our findings represent the first example of miRNA-regulated autophagy in an in vivo setting and in a non-tumor pathological model. Thus, the miR-212/132 family provides new mechanistic insight and offers a therapeutically relevant target for the treatment of cardiac hypertrophy and heart failure development.

TABLE 1

Basic hemodynamic analysis of wild-type (WT) and cardiomyocyte-specific miR-212/132-overexpressing transgenic (TG) mice using pressure-volume catheter system

| Hemodynamic parameters | WT (n = 3) | TG (n = 3) |
|---|---|---|
| HR (bpm) | 506.05 ± 36.03 | 487.00 ± 54.35 |
| Ped (mmHg) | 2.05 ± 5.42 | 6.00 ± 3.30 |
| EF (%) | 70.43 ± 9.71 | 38.36 ± 3.65 |

HR: heart rate; Ped: left ventricular end diastolic pressure; EF: ejection fraction. All values represent mean ± S.E.M.; P values are only significant (<0.05) for EF between WT and TG.

TABLE 2

Hemodynamic analysis of wild-type (WT) and miR-212/132 null (KO) mice using pressure-volume catheter system.

| Hemodynamic parameters | WT(n = 8) | KO(n = 6) |
|---|---|---|
| HR (bpm) | 510.06 ± 10.05 | 527.05 ± 11.88 |
| SV (μL) | 16.43 ± 0.68 | 16.38 ± 0.54 |
| Ves (μL) | 16.45 ± 1.47 | 14.26 ± 1.59 |
| Ved (μL) | 31.26 ± 1.98 | 27.58 ± 2.60 |
| Pes (mmHg) | 87.38 ± 2.66 | 86.73 ± 3.05 |
| Ped (mmHg) | 3.83 ± 0.39 | 2.62 ± 1.06 |
| dP/dt max (mmHg/s) | 8689.95 ± 424.21 | 9022.13 ± 645.49 |
| dP/dt min (mmHg/s) | −8753.19 ± 451.06 | −9063.34 ± 416.60 |
| SW (mmHgμL) | 1232.15 ± 54.49 | 1210.39 ± 58.67 |
| CO (μL/min) | 8337.05 ± 247.40 | 8622.58 ± 270.95 |
| EF (%) | 54.65 ± 1.91 | 61.86 ± 4.57 |
| Ea (mmHg/μL) | 5.36 ± 0.35 | 5.37 ± 0.35 |
| Tau (ms) | 6.24 ± 0.35 | 5.75 ± 0.50 |

HR: heart rate; SV: stroke volume; Ves/Pes: left ventricular end systolic volume/pressure; Ved/Ped: left ventricular end diastolic volume/pressure; dP/dt: rate of rise of left ventricular pressure; SW: stroke work; CO: cardiac output; EF: ejection fraction; Ea: aortic elastance. Statistics: P all not significant between WT and KO.

TABLE 3

Used oligonucleotide primer sequences for mRNA analyses

| Gene | Species | Forward Reverse | SEQ ID NO.: |
|---|---|---|---|
| Anp | Mouse | 5'-CCTGTGTACAGTGCGGTGTC-3' | 10 |
|  |  | 5'-CCTAGAAGCACTGCCGTCTC-3' | 11 |
| Bnp | Mouse | 5'-CTGAAGGTGCTGTCCCAGAT-3' | 12 |
|  |  | 5'-GTTCTTTTGTGAGGCCTTGG-3' | 13 |
| α-MHC | Mouse | 5'-GGTCCACATTCTTCAGGATTCTC-3' | 14 |
|  |  | 5'-GCGTTCCTTCTCTGACTTTCG-3' | 15 |
| β-MHC | Mouse | 5'-TCTCCTGCTGTTTCCTTACTTGCT-3' | 16 |
|  |  | 5'-CAGGCCTGTAGAAGAGCTGTACTC-3' | 17 |
| Gapdh | Mouse | 5'-TTCACCACCATGGAGAAGGC-3' | 18 |
|  |  | 5'-GGCATGGACTGTGGTCATGA-3' | 19 |

TABLE 3-continued

Used oligonucleotide primer sequences for mRNA analyses

| Gene | Species | Forward Reverse | SEQ ID NO.: |
|---|---|---|---|
| FoxO3 | Mouse | 5'-CAAAGCTGGGTACCAGGCTG-3' | 20 |
| | | 5'-TTCCACGGGTAAGGGCTTCA-3' | 21 |
| FoxO3 | Rat | 5'-GATGGTGCGCTGTGTGCCCTAC-3' | 22 |
| | | 5'-CCAAGAGCTCTTGCCAGTCCCTT-3' | 23 |
| LC3-promoter region (ChIP) | Rat | 5'-GGCTGGACTTGAATTCAGAAA-3' | 24 |
| | | 5'-ACTTGCTGTTCCAGGTGGTC- 3' | 25 |
| Atrogin1 | Mouse | 5'-GCAAACACTGCCACATTCTCTC-3' | 26 |
| | | 5'-CTTGAGGGGAAAGTGAGACG-3' | 27 |
| Atrogin1 | Rat | 5'-CCATCAGGAGAAGTGGATCTATGTT-3' | 28 |
| | | 5'-GTTCATGAAGTTCTTTTGGGCGATGC-3' | 29 |
| Mcip1 | Mouse | 5'-CTGCACAAGACCGAGTT-3' | 30 |
| | | 5'-TGTTTGTCGGGATTGG-3' | 31 |
| Mcip1 | Rat | 5'-AGCTCCCTGATTGCCTGTGT-3' | 32 |
| | | 5'-TTTGGCCCTGGTCTCACTTT-3' | 33 |
| Lc3b | Mouse | 5'-CGTCCTGGACAAGACCAAGT-3' | 34 |
| | | 5'-ATTGCTGTCCCGAATGCTC-3' | 35 |
| Ulk2 | Mouse | 5'-CAGCCCTGGATGAGATGTTT-3' | 36 |
| | | 5'-GGATGGGTGACAGAACCAAG-3' | 37 |
| Atg12 | Mouse | 5'-GGCCTCGGAACAGTTGTTTA-3' | 38 |
| | | 5'-CAGCACCGAAATGTCTCTGA-3' | 39 |
| Beclin1 | Mouse | 5'-GGCCAATAAGATGGGTCTGA-3' | 40 |
| | | 5'-CACTGCCTCCAGTGTCTTCA-3' | 41 |
| Plk3c3 | Mouse | 5'-TGTCAGATGAGGAGGCTGTG-3' | 42 |
| | | 5'-CCAGGCACGACGTAACTTCT-3' | 43 |
| Bnip3 | Mouse | 5'-GAACTGCACTTCAGCAATGG-3' | 44 |
| | | 5'-ATTTCAGCTCTGTTGGTATC-3' | 45 |
| Atg5 | Mouse | 5'-GACAAAGATGTGCTTCGAGATGTG-3' | 46 |
| | | 5'-ATAATGCCATTTCAGGGGTGTGC-3' | 47 |

REFERENCES

1. Aki, T.; Yamaguchi, K.; Fujimiya, T.; Mizukami, Y. (2003). Phosphoinositide 3-kinase accelerates autophagic cell death during glucose deprivation in the rat cardiomyocyte-derived cell line H9c2. Oncogene. 22, 8529-8535.
2. Alvarez-Saavedra, M.; Antoun, G.; Yanagiya, A.; Oliva-Hernandez, R.; Cornejo-Palma, D.; Perez-Iratxeta, C.; Sonenberg, N.; Cheng, H. Y. (2011). MiRNA-132 orchestrates chromatin remodeling and translational control of circadian clock. Hum Mol. Genet. 20, 731-751.
3. Barry, S. P.; Townsend, P. A. (2010). What causes a broken heart-Molecular insights into heart failure. Int Rev Cell Mol Biol 284, 113-179.
4. Bartel, D. P. (2009). MicroRNAs: target recognition and regulatory functions. Cell. 136, 215-233.
5. Bauersachs, J.; Thum, T. (2007) MicroRNAs in the broken heart. Eur Clin Invest. 37, 829-833.
6. Callis, T. E.; Pandya, K.; Seok, H. Y.; Tang, R. H.; Tatsuguchi, M.; Huang, Z. P.; Chen, J. F.; Deng, Z.; Gunn, B.; Shumate, J. et al. (2009) MicroRNA-208a is a regulator of cardiac hypertrophy and conduction in mice. J Clin Invest. 119, 2772-2786.
7. Cao, D. J.; Wang, Z. V.; Battiprolu, P. K.; Jiang, N.; Morales, C. R.; Kong, Y.; Rothermel, B. A.; Gillette, T. G.; Hill, J. A. (2011) Histone deacetylase (HDAC) inhibitors attenuate cardiac hypertrophy by suppressing autophagy. Proc Natl Acad Sci U.S.A. 108, 4123-4128.
8. Chen, J. F.; Murchison, E. P.; Tang, R.; Callis, T. E.; Tatsuguchi, M.; Deng, Z.; Rojas, M.; Hammond, S. M.; Schneider, M. D.; Selzman, C. H. et al. (2008). Targeted deletion of Dicer in the heart leads to dilated cardiomyopathy and heart failure. Proc Natl Acad Sci U.S.A. 105, 2111-2116.
9. da Costa Martins, P. A.; Bourajjaj, M.; Gladka, M.; Kortland, M.; van Oort, R. J.; Pinto, Y. M.; Molkentin, J. D.; De Windt, L. J. (2008). Conditional dicer gene deletion in the postnatal myocardium provokes spontaneous cardiac remodeling. Circulation. 118, 1567-1576.
10. Datta, S. R.; Brunet, A.; Greenberg, M. E. (1999). Cellular survival: a play in three Akts. Genes Dev. 13, 2905-2927.
11. DeBosch, B. J.; Muslin, A. J. (2008). Insulin signaling pathways and cardiac growth. J Mol Cell Cardiol. 44, 855-864.
12. Ferdous, A.; Battiprolu, P. K.; Ni, Y. G.; Rothermel, B. A.; Hill, J. A. (2010) FoxO, autophagy, and cardiac remodeling. J Cardiovasc Transl Res. 3, 355-364.
13. Frescas, D.; Valenti, L.; Accili, D. (2005). Nuclear trapping of the forkhead transcription factor FoxO1 via Sirt1-dependent deacetylation promotes expression of glucogenetic genes. J Biol. Chem. 280, 20589-20595.
14. Glas, D. J. (2010). PI3 kinase regulation of skeletal muscle hypertrophy and atrophy. Curr Top Microbiol Immunol. 346, 267-278.
15. Gottlieb, R. A.; Mentzer, R. M. (2010). Autophagy during cardiac stress: joys and frustrations of autophagy. Annu Rev Physiol. 72, 45-59.
16. Gottlieb, R. A.; Gustafsson, A. B. (2011). Mitochondrial turnover in the heart. Biochim Biophys Acta. 1813, 1295-1301.
17. Hamacher-Brady, A.; Brady, N. R.; Gottlieb, R. A. (2006). Enhancing macroautophagy protects against ischemia/reperfusion injury in cardiac myocytes. J Biol. Chem. 281, 29776-29787.
18. Hansen, K. F.; Sakamato, K.; Wayman, G. A.; Impey, S.; Obrietan, K. (2010). Transgenic miR-132 alters neuronal spine density and impairs novel object recognition memory. PloS One. 5, e15497.
19. Hentschel, D. M.; Mengel, M.; Boehme, L.; Liebsch, F.; Albertin, C.; Bonventre, J. V.; Haller, H.; Schiffer, M. (2007). Rapid screening of glomerular slit diaphragm integrity in larval zebrafish. Am J Physiol Renal Physiol. 293, F1746-F1750.
20. Hill, J. A.; Olson, E. N. (2008). Cardiac plasticity. N Engl J. Med. 358, 1370-1380.
21. Jentzsch, C.; Leierseder, S.; Loyer, X.; Flohrschutz, I.; Sassi, Y.; Hartmann, D.; Thum, T.; Laggerbauer, B.; Engelhardt, S. (2011). A phenotypic screen to identify hypertrophy-modulating microRNAs in primary cardiomyocytes. J Mol Cell Cardiol, doi:10.1016/j.yjmcc.2011.07.010 (2011).
22. Li, H. H.; Kedar, V.; Zhang, C.; McDonough, H.; Arya, R.; Wang, D. Z.; Patterson, C. (2004). Atrogin-1/muscle atrophy F-box inhibits calcineurin-dependent cardiac hypertrophy by participating in an SCF ubiquitin ligase complex. J Clin Invest. 114, 1058-1071.
23. Liu, N.; Bezprozvannaya, S.; Williams, A. H.; Qi, X.; Richardson, J. A.; Bassel-Duby, R.; Olson, E. N. (2008). MicroRNA-133 regulates cardiomyocyte proliferation and suppresses smooth muscle gene expression in the heart. Genes Dev. 22, 3242-3254.
24. Magill, S. T.; Cambronne, X. A.; Luikart, B. W.; Lioy, D. T.; Leighton, B. H.; Westbrook, G. L.; Mandel, G.; Goodman, R. H. (2010). microRNA-132 regulates dendritic growth and arborization of newborn neurons in the adult hippocampus. Proc Natl Acad Sci U.S.A. 107, 20382-20387.
25. McMullen, J. R.; Shioi, T.; Huang, W. Y.; Zhang, L.; Tarnayski, O.; Bisping, E.; Schinke, M.; Kong, S.; Sherwood, M. C.; Brown, J. et al. (2004). The insulin-like growth factor 1 receptor induces physiological heart growth via the phosphoinositide 3-kinase (p110alpha) pathway. J Biol. Chem. 279, 4782-4793.
26. Ni, Y. G.; Berenji, K.; Wang, N.; Oh, M.; Sachan, N.; Dey, A.; Cheng, J.; Lu, G.; Morris, D. J.; Castrillon, D. H. et al. (2006). Foxo transcription factors blunt cardiac hypertrophy by inhibiting calcineurin signaling. Circulation. 114, 1159-1168.
27. Okamura, H.; Aramburu, J.; Garcia-Rodriguez, C.; Viola, J. P.; Raghavan, A.; Tahiliani, M.; Zhang, X.; Qin, J., Hogan, P. G.; Rao, A. (2000). Concerted dephosphorylation of the transcription factor NFAT1 induces a conformational switch that regulates transcriptional activity. Mol. Cell. 6, 539-550.
28. Rao, P. K.; Toyama, Y.; Chiang, H. R.; Gupta, S.; Bauer, M.; Medvid, R.; Reinhardt, F.; Liao, R.; Krieger, M.; Jaenisch, R. et al. (2009). Loss of cardiac microRNA-mediated regulation leads to dilated cardiomyopathy and heart failure. Circ Res. 105, 585-594.
29. Ronnebaum, S. M.; Patterson, C. (2010). The foxO family in cardiac function and dysfunction. Annu Rev Physiol. 72, 81-94.
30. Rothermel, B. A.; Vega, R. B.; Williams, R. S. (2003). The role of modulatory calcineurin-interacting proteins in calcineurin signaling. Trends Cardiovasc Med. 13, 15-21.
31. Sandri, M.; Sandri, C.; Gilbert, A.; Skurk, C.; Calabria, E.; Picard, A.; Walsh, K.; Schiaffino, S.; Lecker, S. H.; Goldberg, A. L. (2004). Foxo transcription factors induce the atrophy related ubiquitin ligase atrogin-1 and cause skeletal muscle atrophy. Cell. 117, 399-412.
32. Sayed, D.; He, M.; Hong, C.; Gao, S.; Rane, S.; Yang, Z.; Abdellatif, M. (2010). MicroRNA-21 is a downstream effector of Akt that mediates its antiapoptotic effects via suppression of Fas ligand. J Biol. Chem. 285, 20281-20290.
33. Sengupta, A.; Molkentin, J. D.; Yutzey, K. E. (2009). FoxO transcription factors promote autophagy in cardiomyocytes. J Biol. Chem. 284, 28319-28331.
34. Shvets, E.; Elazar, Z. (2009). Flow cytometric analysis of autophagy in living mammalian cells. Methods Enzymol. 452, 131-141.
35. Skurk, C.; Izumiya, Y.; Maatz, H.; Razeghi, P.; Shiojima, I.; Sandri, M.; Sato, K.; Zeng, L.; Schiekofer, S.; Pimentel, D. et al. (2005). The FOXO3a transcription factor regulates cardiac myocyte size downstream of AKT signaling. J Biol. Chem. 280, 20814-23.
36. Taegtmeyer, H.; Sen, S.; Vela, D. (2010). Return to fetal gene program: a suggested metabolic link to gene expression in the heart. Ann N Y Acad. Sci. 1188, 191-198.
37. Taneike, M.; Yamaguchi, O.; Nakai, A.; Hikoso, S.; Takeda, T.; Mizote, I.; Oka, T.; Tamai, T.; Oyabu, J.; Murakawa, T. et al. (2010). Inhibition of autophagy in the heart induces age-related cardiomyopathy. Autophagy. 6, 600-606.
38. Thum, T.; Galuppo, P.; Wolf, C.; Fiedler, J.; Kneitz, S.; van Laake, L. W.; Doevendans, P. A.; Mummery, C. L.; Borlak, J.; Haverich, A. et al. (2007). MicroRNAs in the human heart: a clue to fetal gene reprogramming in heart failure. Circulation. 116, 258-267.
39. Thum, T.; Catalucci, D.; Bauersachs, J. (2008). MicroRNAs: novel regulators in cardiac development and disease. Cardiovasc Res. 79, 562-570.
40. Ucar, A.; Vafaizadeh, V.; Jarry, H.; Fiedler, J.; Klemmt, P. A.; Thum, T.; Groner, B.; Chowdhury, K. (2010). mir-212 and miR-132 are required for epithelial stromal interactions necessary for mouse mammary gland development. Nat. Genet. 42, 1101-1008.
41. Ucar, A.; Vafaizadeh, V.; Chowdhury, K.; Groner, B. (2011). MicroRNA-dependent regulation of the microenvironment and the epithelial stromal cell interactions in the mouse mammary gland. Cell Cycle. 10, 563-565.
42. Valencia-Sanchez, M. A.; Liu, J.; Hannon, G. J.; Parker, G. (2006). Control of translation and mRNA degradation by miRNAs and siRNAs. Genes Dev. 20, 515-524.
43. van Rooij, E.; Sutherland, L. B.; Qi, X.; Richardson, J. A.; Hill, J.; Olson, E. N. (2007). Control of stress-dependent cardiac growth and gene expression by a microRNA. Science. 316, 575-579.
44. van Rooij, E.; Quiat, D.; Johnson, B. A.; Sutherland, L. B.; Qi, X.; Richardson, J. A.; Kelm, R. J. Jr.; Olson, E. N. (2009). A family of microRNAs encoded by myosin genes governs myosin expression and muscle performance. Dev Cell. 17, 662-673.
45. Ventura, A.; Young, A. G.; Winslow, M. M.; Lintault, L.; Meissner, A.; Erkeland, S. J.; Newman, J.; Bronson, R. T.; Crowley, D.; Stone, J. R. et al. (2008). Targeted deletion reveals essential and overlapping functions of the miR-17 through 92 family of miRNA clusters. Cell. 132, 875-886.
46. Wang, K.; Li, P. F. (2002). Foxo3a regulates apoptosis by negatively targeting miR-21. J Biol. Chem. 285, 16958-16966.
47. Zhao, Y.; Ransom, J. F.; Li, A.; Vedantham, V.; von Drehle, M.; Muth, A. N.; Tsuchihashi, T.; McManus, M. T.; Schwartz, R. J.; Srivastava, D. (2007). Cell. 129, 303-317.
48. Zhu, H.; Wu, H.; Liu, X.; Li, B.; Chen, Y.; Ren, X. Liu, C. G.; Yang, J. M. (2009). Regulation of autophagy by a beclin 1-targeted microRNA, miR-30a, in cancer cells. Autophagy. 5, 816-823.
49. Krützfeldt, J.; Rajewsky, N.; Braich, R.; Rajeev, K. G.; Tuschl, T.; Manoharan, M.; Stoffel, M. (2005). Silencing of microRNAs in vivo with 'antagomirs'. Nature. 438, 685-689.
50. Merkle, S.; Frantz, S.; Schon, M. P.; Bauersachs, J.; Buitrago, M.; Frost, R. J.; Schmitteckert, E. M.; Lohse, M. J.; Engelhardt, S. (2007). A role for caspase-1 in heart failure. Circ Res. 100, 645-653.
51. Rockman, H. A.; Ross, R. S.; Harris, A. N.; Knowlton, K. U.; Steinhelper, M. E.; Field, L. J.; Ross, J. Jr.; Chien, K. R. (1991) Segregation of atrial-specific and inducible expression of an atrial natriuretic factor transgene in an in vivo murine model of cardiac hypertrophy. Proc Natl Acad Sci U.S.A. 88, 8277-8281.

52. Czech, M. P. (2006). MicroRNAs as Therapeutic Targets. New England J. Med. 354, 1194-1195.
53. Fiedler J.; Jazbutyle V.; Kirchmaier B. C.; Gupta S. K.; Lorenzen J.; Hartmann D.; Galuppo P.; Kneitz S.; Pena J T.; Sohn-Lee C.; Loyer X.; Soutschek J.; Brand T.; Tuschl T.; Heineke J.; Martin U.; Schulte-Merker S.; Ertl G.; Engelhardt S.; Bauersachs J.; Thum T. (2011) MicroRNA-24 Regulates Vascularity After Myocardial Infarction. Circulation. 124(6), 720-30.
54. Anker S. D. and Coats A. J. (1999) Cardiac cachexia: a syndrome with impaired survival and immune and neuroendocrine activation. Chest. 115(3):836-47.
55. Anker S. D., Ponikowski P., Varney S., Chua T. P., Clark A. L., Webb-Peploe K. M., Harrington D., Kox W. J., Poole-Wilson P. A., Coats A. J. (1997) Wasting as independent risk factor for mortality in chronic heart failure. Lancet. 349(9058):1050-1053.
56. Nakai, A. et al. The role of autophagy in cardiomyocytes in the basal state and in response to hemodynamic stress. Nat. Med. 13, 619-624 (2007).
57. Chen, J. F. et al. Targeted deletion of Dicer in the heart leads to dilated cardiomyopathy and heart failure. Proc Natl Acad Sci U.S.A. 105, 2111-2116 (2008).
58. da Costa Martins, P. A. et al. MicroRNA-199b targets the nuclear kinase Dyrk1a in an auto-amplification loop promoting calcineurin/NFAT signalling. Nat. Cell Biol. 12, 1220-1227 (2010).
59. Bauersachs, J. & Thum, T. Biogenesis and regulation of cardiovascular MicroRNAs. Circ Res. 109, 334-347 (2011).
60. Thum, T. et al. MicroRNA-21 contributes to myocardial disease by stimulating MAP kinase signaling in fibroblasts. Nature 456, 980-984 (2008).
61. Komatsu, M. et al. Homeostatic levels of p62 control cytoplasmic inclusion body formation in autophagy-deficient mice. Cell. 131, 1149-1163 (2007).
62. Kanamori, H. et al. The role of autophagy emerging in postinfarction cardiac remodelling. Cardiovasc Res. 91, 330-339 (2011).
63. Jung, C. H., Ro, S. H., Cao, J., Otto N. M., Kim, D. H. mTOR regulation of autophagy. FEBS Lett. 584, 1287-1295 (2010).
64. Kumarswamy, R., et al., SERCA2a gene therapy restores microRNA-1 expression in heart failure via an Akt/FoxO3A-dependent pathway. Eur Heart J. 33, 1067-1075 (2012).
65. Kanamori, H. et al. Functional significance and morphological characterization of starvation-induced autophagy in the adult heart. Am J. Pathol. 174, 1705-1714 (2009).
66. Ullman-Cullere, M. H., Foltz, C. J. Body condition scoring: a rapid and accurate method for assessing health status in mice. Lab Anim Sci. 49, 319-323 (1999).
67. Napp L C et al. Extrinsic Notch Ligand Delta-Like 1 Regulates Tip Cell Selection and Vascular Branching Morphogenesis. Circ Res. 110, 530-535 (2012).

The invention claimed is:

1. A pharmaceutical composition comprising
   a) an inhibitor of miR-132 wherein the inhibitor is an isolated nucleic acid molecule comprising at least one modified building block, and
   b) a further medicament selected from the group consisting of angiotensin-modulating agents, β-blockers, diuretics, aldosterone antagonists, vasodilators, ionotrophic agents and combinations thereof.

2. The composition according to claim 1, wherein the inhibitor has sufficient complementarity to miR-132 to form a hybrid under physiological conditions.

3. The composition according to claim 1, wherein the inhibitor is a single-stranded or double-stranded nucleic acid molecule.

4. The composition according to claim 1, wherein the inhibitor is an RNA molecule comprising at least one modified building block.

5. The composition according to claim 4, wherein the modified building block is selected from the group consisting of nucleobase-modified building blocks, sugar-modified building blocks, backbone-modified building blocks and combinations thereof.

6. The composition according to claim 1, wherein the inhibitor is an siRNA molecule or an antagomir.

7. The composition according to claim 1, wherein said further medicament is suitable for the treatment of cardiac hypertrophy-associated or autophagic disorders.

8. The composition according to claim 1, wherein said further medicament is suitable for the treatment or prevention of contractile dysfunction, cardiac decompensation or heart failure.

9. The composition according to claim 7, wherein said further medicament is suitable for the treatment of autophagic disorder.

10. The composition according to claim 1, wherein said further medicament is suitable for the treatment of patients selected from the group consisting of:
    (i) patients having an increased risk of heart failure,
    (ii) patients suffering from (congestive) heart failure,
    (iii) post-myocardial infarction patients, and
    (iv) patients with congenital heart diseases associated with cardiac hypertrophy, selected from the group consisting of pulmonal vein stenosis, and atrial or ventricular septum defects.

11. An isolated nucleic acid molecule comprising
    (a) a nucleotide sequence as shown in SEQ ID NO.: 1, SEQ ID NO.: 2, SEQ ID NO.: 3 and/or SEQ ID NO: 4, or a precursor of SEQ ID NO.: 1, SEQ ID NO.: 2, SEQ ID NO.: 3 and/or SEQ ID NO: 4, and/or
    (b) a nucleotide sequence which is the complement of (a), and/or
    (c) a nucleotide sequence which has an identity of at least 80% to a sequence of (a) or (b), and/or
    (d) a nucleotide sequence which hybridizes under stringent conditions to a sequence of (a), (b) and/or (c)
    wherein said isolated nucleic acid molecule comprises at least one modified building block, wherein the modified building block is selected from the group consisting of nucleobase-modified building blocks, sugar-modified building blocks, backbone-modified building blocks and combinations thereof.

12. The isolated nucleic acid molecule according to claim 11, wherein the identity of sequence (c) is at least 90%.

13. The isolated nucleic acid molecule according to claim 11, wherein said isolated nucleic acid molecule is a single-stranded or double-stranded nucleic acid molecule.

14. The isolated nucleic acid molecule according to claim 11, wherein said isolated nucleic acid molecule is a miRNA molecule or an analog thereof having a length of from 18-25 nucleotides, or a miRNA precursor molecule having a length of 50-120 nucleotides or a DNA molecule coding therefor.

15. The miRNA molecule according to claim 14, which has a length of 21 or 22 nucleotides.

16. The isolated nucleic acid molecule according to claim 11, wherein said isolated nucleic acid molecule is an RNA molecule.

17. The isolated nucleic acid molecule according to claim 11, wherein said isolated nucleic acid molecule is suitable for the diagnosis, treatment or prevention of disorders involving cardiac atrophy and/or dysfunctional autophagy.

18. The isolated nucleic acid molecule according to claim 17, wherein said isolated nucleic acid molecule is suitable for the diagnosis, treatment or prevention of disorders involving cardiac atrophy and/or exaggerated autophagy selected from the group consisting of cancer, anorexia, bulimia, and body wasting associated with cancer.

19. The isolated nucleic acid molecule according to claim 11, wherein said isolated nucleic acid molecule is suitable for the diagnosis, treatment or prevention of cardiac cachexia.

20. The isolated nucleic acid molecule according to claim 11, wherein said isolated nucleic acid molecule is suitable for administration to patients selected from the group consisting of:
    (i) patients having an increased risk for or suffering from autophagic disorders,
    (ii) patients having an increased risk for or suffering from cardiac cachexia, and
    (iii) patients having an increased risk for or suffering from cardiac atrophy.

21. A method for the diagnosis, prevention or treatment of a cardiac disorder comprising administering to a subject in need thereof a therapeutically effective amount of at least one isolated nucleic acid molecule according to claim 11.

22. The composition according to claim 9, wherein said further medicament is suitable for the treatment of an autophagic disorder associated with reduced or absent autophagy, selected from the group consisting of neurodegenerative diseases, liver diseases, muscle diseases, cancer, autoimmune disorders, infectious diseases and aging.

23. The isolated nucleic acid molecule according to claim 12, wherein the identity of sequence (c) is at least 95%.

* * * * *